(12) United States Patent
Houtz et al.

(10) Patent No.: US 7,445,923 B2
(45) Date of Patent: Nov. 4, 2008

(54) CRYSTALLIZATION AND STRUCTURE OF A PLANT PEPTIDE DEFORMYLASE

(75) Inventors: Robert L. Houtz, Lexington, KY (US); David W. Rodgers, Versailles, KY (US); Lynette M. A. Dirk, Lexington, KY (US); Mark A. Williams, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 11/542,989

(22) Filed: Oct. 3, 2006

(65) Prior Publication Data

US 2008/0124808 A1  May 29, 2008

Related U.S. Application Data

(60) Provisional application No. 60/835,823, filed on Aug. 4, 2006.

(51) Int. Cl.
*C12N 9/78* (2006.01)
*G01N 31/00* (2006.01)

(52) U.S. Cl. .......................................... 435/227; 436/4
(58) Field of Classification Search ........................ None
See application file for complete search history.

(56) References Cited

U.S. PATENT DOCUMENTS

| | | | |
|---|---|---|---|
| 5,985,273 | A | 11/1999 | Reed et al. |
| 6,730,634 | B1 | 5/2004 | Houtz et al. |
| 6,864,080 | B2 | 3/2005 | Baldwin et al. |
| 2004/0088755 | A1 | 5/2004 | Houtz et al. |

OTHER PUBLICATIONS

A Hypertext Book of Crystallographic Space Group Diagrams and Tables, Birkbeck College, University of London, 1997-1999, Retrieved from the Internet <URL: http://img.chem.ucl.ac.uk/sgp/mainmenu.htm>.*

McPherson et al., Eur. J. Biochem. 189:1-23, 1990.*
Kierzek et al., Biophys Chem 91:1-20, 2001.*
Branden et al., "Introduction to Protein Structure Second Edition", Garland Publishing Inc., New York, 1999.*
Drenth, "Principles of X-ray Crystallography," Springer, New York, 1995.*
Fieulaine et al., The crystal structure of mitochondrial (Type 1A) peptide deformylase provides clear guidelines for the design of inhibitors specific for the bacterial forms, Journal of Biological Chemistry, published Sep. 28, 2005, vol. 280, No. 51, p. 42315-42624.*
Dardel et al., Solution structure of nickel-peptide deformylase, J. Mol. Biol. (1998) 280, 501-513.*
Chan et al., Crystal Structure of the *Escherichia coli* Peptide Deformylase, Biochemistry, 1997, 36, 13904-13909.*
Definition of "ligand" Retrieved from the Internet <URL:http://stedmans.com/> on Oct. 29, 2007.*
Akers, Alan, "Molecular Biology as Virtual Biology: Limitations of Molecular Biology in Pesticide Discovery", 1996, pp. 85-91, vol. 46, Pesticide Science, Great Britain.
Braun, et al. Purification and sequencing of cytochrome b from potato reveals methionine cleavage of mitochondrially encoded protein, FEBS Letters 316: 128-132, 1993.
Chen, et a., "Actinonin, a Naturally Occurring Antibacterial Agent, Is a Potent Deformylase Inhibitor", Biochemistry 2000, vol. 39, pp. 1256-1262, American Cancer Society, Washington, D.C.
Giglione et al., "Identification of eukaryotic peptide deformylases reveals universality of N-terminal protein processing mechanisms", The EMBO Journal, Sep. 13, 2000, pp. 5916-5929, vol. 19, No. 21, European Molecular Biology Organization, France.
Giglione, et al. "Peptide deformylase as a target for new generation, broad spectrum antimicrobial agents", Microreview, Molecular Microbiology, 2000, 36(6):1197-1205, Blackwell Science, Ltd., Oxford, England.
Meinnel, T., "Peptide deformylasae of Eukaryotic Protists: A Target for New Antiparasitic Agents?" Parasitology Today 200, pp. 156-168, vol. 16, No. 4 Elsevier Science, Ltd., Oxford, England.

* cited by examiner

*Primary Examiner*—David J. Steadman
*Assistant Examiner*—Jae W Lee
(74) *Attorney, Agent, or Firm*—Crowell & Moring, LLP

(57) ABSTRACT

This invention relates to the crystal structure of a plant peptide deformylase polypeptide and methods of using the structure to design compounds that modulate the activity of the polypeptide.

4 Claims, 15 Drawing Sheets

```
         70          80          90         100         110         120
      KDDKVA SATDVQFETP LKIVEYPDPI LRAKNKRIDI FDENLKNLVD AMFDVMYKTD 130         140         150         160         170         180
  GIGLSAPQVG LNVQLMVFNP AGEPGEGKEI VLVNPKIKKY SDKLVPFDEG CLSFPGIYAE 190         200         210         220         230         240
  VVRPQSVKID ARDITGERFS ISLSRLPARI FQHEYDHLEG VLFFDRMTDQ VLDSIREELE 250         257
  ALEKKYEEKT GLPSPER
```

Motif I

| | | | | | | | | | | | | | | | | | |
|---|---|---|---|---|---|---|---|---|---|---|---|---|---|---|---|---|---|
| AtDEF1 sequence | | | | | | | | | | | | | | | | | |
| 44 sequence alignment | | | | | | | | | | | | | | | | | |
| residue numbering of the sequence is difficult because of different translational start sites, however going with the METLFR as start, numbering is as follows: | | | | | | | | | | | | | | | | | |
| #: | 112 | 113 | 114 | 115 | 116 | 117 | 118 | 119 | 120 | 121 | 122 | 123 | 124 | 125 | 126 | | |
| 1ZXZ RESIDUE # | 45 | 46 | 47 | 48 | 49 | 50 | 51 | 52 | 53 | 54 | 55 | 56 | 57 | 58 | 59 | | |
| Number of sequences aligned at this residue: | | | | | | | | | | | | | | | | | |
| | 34 | 34 | 34 | 34 | 34 | 31 | 31 | 31 | 31 | 31 | 31 | 31 | 32 | 33 | 34 | | |
| | A | P | G | V | G | L | A | A | P | Q | I | G | V | P | L | | R |

| | A | P | G | V | G | L | A | A | P | Q | I | G | V | P | L | | R |
|---|---|---|---|---|---|---|---|---|---|---|---|---|---|---|---|---|---|
| A | 31 | | | | | | 31 | 31 | | | | | | | | | |
| C | | 1 | | | | | | | | | | | | | | | |
| D | | | | | | | | | | | | | | | | | |
| E | | | | | | | | | | | | | | 1 | | | 2 |
| F | | | | | | | | | | | | | 1 | | | | |
| G | | | 32 | | 31 | | | | | | 28 | 31 | | | | | |
| H | | | | | | | | | | | | | 16 | | | | |
| I | | | | | | | | | | | 3 | | | | | | 30 |
| K | | | | | | | | | | 31 | | | 1 | | | | |
| L | | | | 1 | | 31 | | | | | | | | 30 | | | 1 |
| M | | | | | | | | | | | | | | | | | |
| N | | | | | | | | | | | | | | | | | |
| P | | 33 | | | | | | | 31 | | | | 13 | | 2 | | 1 |
| Q | | | | 1 | | | | | | | | | | 1 | | | |
| R | | | | | | | | | | | | | | | | | |
| S | | 1 | | | | | | | | | | | | | | | |
| T | | | | | | | | | | | | | | | | | |
| V | | 1 | | 27 | | | | | | | | | | | | | |
| W | | | | | | | | | | | | | | | | | |
| Y | | | | | | | | | | | | | | | | | |
| SUM CHECK | 34 | 34 | 34 | 34 | 34 | 31 | 31 | 31 | 31 | 31 | 31 | 31 | 32 | 33 | 34 | | |

FIG. 6, PANEL A

Motif II

| | AtDEF1 sequence |
|---|---|
| | 44 sequence alignment | residue numbering of the sequence is difficult because of different translational start sites, however going with the METLFR as start, numbering is as follows:

| #: | 172 | 173 | 174 | 175 | 176 | 177 | 178 | 179 | 180 | 181 | 182 | 183 | 184 | 185 | 186 | |
|---|---|---|---|---|---|---|---|---|---|---|---|---|---|---|---|---|
| 1ZXZ RESIDUE# | 105 | 106 | 107 | 108 | 109 | 110 | 111 | 112 | 113 | 114 | 115 | 116 | 117 | 118 | 119 | |
| Number of sequences aligned at this residue: | 41 | 42 | 42 | 42 | 43 | 43 | 43 | 43 | 43 | 41 | 41 | 40 | 40 | 40 | 39 | 39 |
| | A | L | F | F | E | G | C | L | S | V | D | G | F | R | A | A |
| A | 41 | | | | | | | | | | | | | | | |
| C | | 2 | | | | | | | | | | | | | | |
| D | | | | | | | | | | 1 | 31 | | 1 | | | |
| E | | | | | 42 | 1 | | | | | | | | | | |
| F | | 7 | 41 | 33 | | | | 1 | 1 | | | 39 | 24 | | | |
| G | | | | | 1 | 41 | | | | | | | | | | |
| H | | | | | | | | | | | | | | | | |
| I | | | | | | | 1 | | | | | | | | | |
| K | | 3 | | | | | | | | | | | | | | |
| L | | 21 | 1 | | | | 42 | 41 | | | | | 1 | | | |
| M | | | | | | | | | 1 | | | | | | | |
| N | | | | | | | | | | | 6 | | | | | |
| P | | | | | | | | | | | 2 | 1 | | | | |
| Q | | 2 | | | | | | | | | | | | | | |
| R | | 6 | | | | | | | | | | | | 1 | 36 | |
| S | | | | | | | | 1 | 39 | | | | | | 2 | |
| T | | | | | | | | | | | | | | | | |
| V | | | | | | | | | | 39 | | | | 1 | | |
| W | | | 1 | | | | | | | 1 | | | | | | |
| Y | | | | 8 | | | | | | | | | 14 | | | |
| SUM CHECK | 41 | 42 | 42 | 42 | 43 | 43 | 43 | 43 | 43 | 41 | 41 | 40 | 40 | 40 | 39 | 0 |

*FIG. 6, PANEL B*

Motif III

| | AtDEF1 sequence | | | | | | | | | | | | | | | |
|---|---|---|---|---|---|---|---|---|---|---|---|---|---|---|---|---|
| | 44 sequence alignment | | | | | | | | | | | | | | | |
| | residue numbering of the sequence is difficult because of different translational start sites, however going with the METLFR as start, numbering is as follows: | | | | | | | | | | | | | | | |
| #: | 212 | 213 | 214 | 215 | 216 | 217 | 218 | 219 | 220 | 221 | 222 | 223 | 224 | 225 | 226 | |
| 1ZXZ RESIDUE# | 145 | 146 | 147 | 148 | 149 | 150 | 151 | 152 | 153 | 154 | 155 | 156 | 157 | 158 | 159 | |
| Number of sequences aligned at this residue: | 35 | 35 | 35 | 34 | 34 | 34 | 33 | 33 | 33 | 32 | 31 | 30 | 30 | 29 | 29 | |
| | G | W | Q | A | R | I | L | Q | H | E | C | D | H | L | D | G |
| A | | | | 33 | | | | | | | | | | | | 4 |
| C | | | | | | | | | | | 3 | | | | | |
| D | 33 | | | | | | | | | | | 29 | | | | 12 |
| E | | | | | | | | | | 31 | | | | | 28 | 13 |
| F | | | | | | | | | 1 | | | | | | | |
| G | 33 | | | | | | | | | | | | | | | |
| H | | | | | | | | 32 | 32 | 1 | | | 29 | | | |
| I | | 1 | | | 1 | 33 | | | | | | | 1 | | | |
| K | | | | | | | | | | | | | | | | |
| L | | | 5 | | | | 33 | | | | | | | | | |
| M | | 1 | | | | | | | | | | | | | | |
| N | | 1 | | | | | | 1 | | | | | | | | |
| P | | | | | | | | | | | | | | | | |
| Q | | | 29 | | 33 | | | | | | | 1 | | | | |
| R | | | | | | | | | | | | | | | | |
| S | | | | | | | | | | | | | | | | |
| T | | | | | | | | | | | 1 | | | | 1 | |
| V | | | | | | | | | | | 27 | | | | | |
| W | | 34 | | | | | | | | | | | | | | |
| Y | | | 1 | | | 1 | | | | | | | | 1 | | |
| SUM CHECK | 35 | 35 | 35 | 34 | 34 | 34 | 33 | 33 | 33 | 32 | 31 | 30 | 30 | 29 | 29 | 29 |

FIG. 6, PANEL C

Motif I

| | AtDEF2 sequence | | | | | | | | | | | | | | | |
|---|---|---|---|---|---|---|---|---|---|---|---|---|---|---|---|---|
| | 52 sequence alignment | | | | | | | | | | | | | | | |
| RESIDUE# | 119 | 120 | 121 | 122 | 123 | 124 | 125 | 126 | 127 | 128 | 129 | 130 | 131 | 132 | 133 | 134 |
| Number of sequences aligned at this residue: | | | | | | | | | | | | | | | | |
| | 42 | 42 | 42 | 42 | 42 | 42 | 43 | 43 | 43 | 44 | 44 | 44 | 44 | 44 | 44 | 1 |
| | T | Q | G | I | G | L | S | A | P | Q | V | G | L | N | V | L |
| A | | | | | | | | 1 | | | | | | | | |
| C | | | | | | | | | | | | | | | | |
| D | | | | | | | | 1 | | | | | | | | |
| E | | 1 | | | | | | | | | | | | | | |
| F | | | | | | | | | | | | | | | | |
| G | | | 42 | | 42 | | | | | | | 44 | | | | |
| H | | | | | | | | | | | | | | | | |
| I | | | | 37 | | | | | | | | | 17 | | | |
| K | 1 | | | | | | | | | | | | | | | |
| L | | | | | 42 | | | | | 3 | | | | |
| M | | | | | | | | | | | 5 | | | | | |
| N | | | | | | | | | | | | | 8 | | | |
| P | | | | | | | | | 43 | | | | | | | |
| Q | | 41 | | | | | | | | 43 | | | | | | |
| R | | | | | | | | | | | | | | | | |
| S | | | | | | | 42 | | | | | | | 1 | | |
| T | 40 | | | | | | | 1 | | | | | | | | |
| V | | | | | | | | | | | 39 | | 16 | 43 | 44 | |
| W | | | | | | 5 | | | | | | | | | | |
| Y | | | | | | | | | | | | | | | | |
| SUM CHECK | 42 | 42 | 42 | 42 | 42 | 42 | 43 | 43 | 43 | 44 | 44 | 44 | 44 | 44 | 44 | 0 |

*FIG. 7, PANEL A*

Motif II

| | | | | | | | | | | | | | | | | | |
|---|---|---|---|---|---|---|---|---|---|---|---|---|---|---|---|---|---|
| | AtDEF2 sequence | | | | | | | | | | | | | | | | |
| | 52 sequence alignment | | | | | | | | | | | | | | | | |
| RESIDUE# | 165 | 166 | 167 | 168 | 169 | 170 | 171 | 172 | 173 | 174 | 175 | 176 | 177 | 178 | 179 | 180 | |
| | Number of sequences aligned at this residue: | | | | | | | | | | | | | | | | |
| | 43 | 43 | 42 | 43 | 43 | 43 | 43 | 43 | 43 | 42 | 41 | 41 | 40 | 40 | 0 | 0 | |
| | L | P | F | D | E | G | C | L | S | F | P | G | I | V | A | E | V |
| A | | | | | | | | | | | | | | | | | |
| C | | | | | | | 43 | | | | | | | | | | |
| D | | | | 4 | | | | | | | | | | | | | |
| E | | | | 18 | 42 | | | | | | | | | | | | |
| F | 4 | | 28 | | | | | | | 42 | | | | | | | |
| G | | | 1 | | | 42 | | | | | | 33 | | | | | |
| H | | | | | | | | | | | | | | | | | |
| I | 6 | | | | | | | | | | | 2 | 39 | | | | |
| K | | | | | | 1 | | | | | | | | | | | |
| L | | | | | | | | 43 | | | | | 1 | | | | |
| M | | | | | | | | | | | | 3 | | | | | |
| N | | | | 17 | | | | | | | | | | | | | |
| P | | 15 | | | | | | | | | 41 | | | | | | |
| Q | | | | | | | | | | | | | | | | | |
| R | 4 | | | 1 | | 1 | | | | | | 1 | | 2 | | | |
| S | 3 | | | 3 | | | | | 43 | | | | | | | | |
| T | 7 | | | | | | | | | | | | | | | | |
| V | 13 | 12 | | | | | | | | | | | | | | | |
| W | | | | | | | | | | | | | | | | | |
| Y | | | 13 | | | | | | | | | | | 29 | | | |
| | 43 | 43 | 42 | 43 | 43 | 43 | 43 | 43 | 43 | 42 | 41 | 41 | 40 | 40 | 0 | 0 | |
| SUM CHECK | 0 | | | | | | | | | | | | | | | | |

FIG. 7, PANEL B

Motif III

FIG. 7, PANEL C

| | | | | | | | | | | | | | | | | |
|---|---|---|---|---|---|---|---|---|---|---|---|---|---|---|---|---|
| AtDEF2 sequence | | | | | | | | | | | | | | | | |
| 52 sequence alignment | | | | | | | | | | | | | | | | |
| RESIDUE# | 205 | 206 | 207 | 208 | 209 | 210 | 211 | 212 | 213 | 214 | 215 | 216 | 217 | 218 | 219 | 220 |
| Number of sequences aligned at this residue: | 36 | 36 | 36 | 36 | 36 | 36 | 36 | 36 | 36 | 36 | 35 | 35 | 35 | 35 | 32 | 2 |
| | S | L | P | A | R | I | F | Q | H | E | Y | D | H | L | E | G | V |
| A | 3 | | | 34 | | | | | | | | | | | | |
| C | | | | | | | | | | | | | | | | |
| D | 7 | | | | | | | | | | | 35 | | | | |
| E | 4 | | | | | | | | 36 | | 26 | | | | 6 | |
| F | | | 3 | | | | 36 | | | | | | | | | |
| G | 15 | | | | | | | | | | | | | | | |
| H | | | | | | | | | | | | | 34 | | | |
| I | 1 | | | | | 4 | | | | | | | | | | |
| K | | 1 | | | | | | | | | | | | | | |
| L | | 31 | | | | | | | | | | | | 35 | 3 | |
| M | | | | | | | | | | | | | 1 | | | |
| N | | | 2 | | | | | | | | | | | | | |
| P | | | 24 | 1 | | | | | | | | | | | | |
| Q | | | 1 | | | | | 36 | | | | | | | 21 | |
| R | | | | 1 | 36 | | | | | | | | | | 2 | |
| S | 5 | | 6 | | | 1 | | | | | | | | | | |
| T | 1 | | 1 | | | | | | | | | | | | | |
| V | | | | | | 21 | | | | | 9 | | | | | |
| W | | | | | | | | | | | | | | | | |
| Y | | 1 | | | | | | | | 36 | | | | | | |
| SUM CHECK | 0 | 0 | 0 | 0 | 0 | 0 | 0 | 0 | 0 | 0 | 35 | 35 | 35 | 35 | 32 | 0 |

Motif I

| | Q2VP16_ECOLI | (Also #age for the most part because mostly 100 sequences in the determination) | | | | | | | | | | | | | | | |
|---|---|---|---|---|---|---|---|---|---|---|---|---|---|---|---|---|---|
| | 100 sequence alignment: Blasted E coli and then from the list returned, removed all below the first non-DEF protein, removed all DEFs with number other than 1 and with precuror assignment | | | | | | | | | | | | | | | | |
| | Q2VP16 RESIDUE# | 41 | 42 | 43 | 44 | 45 | 46 | 47 | 48 | 49 | 50 | 51 | 52 | 53 | 54 | 55 | 56 |
| | Number of sequences aligned at this residue: | | | | | | | | | | | | | | | | |
| | 97 | 98 | 99 | 99 | 100 | 100 | 100 | 100 | 100 | 100 | 100 | 100 | 100 | 100 | 100 | 100 | 100 |
| | Y | A | E | K | G | I | G | L | A | A | T | Q | V | D | I | H | Q | R |
| A | | 43 | | | 4 | 8 | 3 | | 92 | 97 | 1 | | | | | 1 | |
| C | | | | | 2 | | | | 2 | | | | | | | | |
| D | | | | 16 | | | | | | | | | 6 | 3 | | | |
| E | | | 7 | 10 | | | | | | | | | | 14 | 5 | 5 | 4 |
| F | | | 2 | | | | | | | | | | | | | 3 | |
| G | | | | | 94 | | 97 | | 1 | | | | | 70 | | | |
| H | | | 3 | 1 | | | | | | 2 | | | | | 2 | 8 | 6 |
| I | | | 5 | 2 | | 33 | | 14 | | | 10 | 41 | | | 30 | | 41 |
| K | | | 2 | 9 | | | | | | | | | | | 1 | 2 | 29 |
| L | | | 18 | | | | | 85 | | | | 13 | | 14 | 15 | |
| M | | | 1 | | | | | | | | 16 | 2 | | 10 | 1 | 6 | |
| N | | | 4 | 9 | | | | | | | 57 | | | | 1 | 21 | |
| P | | | | 20 | | | | | | | | 94 | | | 4 | 1 | 10 |
| Q | | | 2 | 1 | | | | | | | 1 | | | | 3 | | 4 |
| R | | | | 26 | | | | | | | | | | | 1 | 27 | |
| S | | | 7 | | | | | | 1 | | 10 | | | | | | |
| T | | | 2 | 1 | | | | | 4 | 1 | 5 | | 45 | 31 | 4 | |
| V | | | | | | 59 | | | | | | | | 1 | | 2 | 6 |
| W | | | | | | | | | | | | | | | | | |
| Y | | | 3 | | | | | | | | | | | | | | |
| SUM CHECK | 0 | 0 | 99 | 99 | 100 | 100 | 100 | 100 | 100 | 100 | 100 | 100 | 100 | 100 | 100 | 100 | 100 |

FIG. 8, PANEL A

FIG. 8, PANEL B

Motif II

| Q2VP16_ECOLI | (A so #age for the most part because mostly 100 sequences in the determination) | | | | | | | | | | | | | | | | |
|---|---|---|---|---|---|---|---|---|---|---|---|---|---|---|---|---|---|
| 100 sequence alignment: Blasted E coli and then from the list returned, removed all below the first non-DEF protein, removed all DEFs with number other than 1 and with precuror assignment | | | | | | | | | | | | | | | | | |
| Q2VP16 RESIDUE# | 84 | 85 | 86 | 87 | 88 | 89 | 90 | 91 | 92 | 93 | 94 | 95 | 96 | 97 | 98 | 99 | 100 |
| Number of sequences aligned at this residue: | | | | | | | | | | | | | | | | | |
|  | 0 | 99 | 99 | 99 | 100 | 100 | 100 | 100 | 100 | 100 | 100 | 100 | 100 | 100 | 100 | 99 | 10 |
|  | E | T | G | I | E | E | G | C | L | S | I | P | E | Q | R | A | L |
| A |  | 5 | 3 | 6 |  |  |  |  |  |  |  |  | 1 | 2 | 4 |  |  |
| C |  | 4 |  | 2 |  |  |  |  |  |  |  |  |  |  |  |  |  |
| D |  | 8 | 2 | 15 | 3 |  |  |  |  |  |  | 20 | 17 | 3 | 1 |  |  |
| E |  | 9 | 7 | 7 | 22 | 100 |  |  |  |  | 9 |  | 14 | 9 | 7 |  |  |
| F |  |  |  | 9 | 2 |  |  |  |  |  |  |  |  |  | 4 |  |  |
| G |  | 2 | 6 | 19 | 23 |  | 99 |  |  |  |  | 1 | 43 | 3 | 2 |  |  |
| H |  | 1 |  | 4 |  |  |  |  |  |  |  |  | 2 | 11 | 4 |  |  |
| I |  | 11 | 4 | 3 | 2 |  |  |  |  |  | 30 |  | 2 | 2 |  |  |  |
| K |  | 2 | 3 |  | 5 |  |  |  |  |  |  | 2 | 2 | 10 | 2 |  |  |
| L |  | 21 | 1 |  | 3 |  |  | 92 | 90 |  | 10 |  |  | 2 |  |  | 0 |
| M |  | 2 | 4 | 2 |  |  |  |  | 1 |  | 4 |  |  |  | 1 |  |  |
| N |  | 1 | 3 | 1 | 7 |  |  |  |  |  |  |  | 10 |  |  |  |  |
| P |  |  | 5 | 1 | 3 |  |  |  |  |  |  | 76 | 1 |  | 9 |  |  |
| Q |  | 11 | 3 | 1 | 12 |  |  | 8 |  |  |  |  | 1 | 4 | 11 |  |  |
| R |  |  | 2 |  | 6 |  |  |  |  |  |  |  |  | 4 | 13 |  |  |
| S |  | 9 | 18 | 4 |  |  |  |  |  | 98 |  |  |  |  | 8 |  |  |
| T |  | 2 | 22 | 4 | 3 |  |  |  | 4 | 2 | 47 |  | 1 |  | 2 |  |  |
| V |  | 9 | 13 | 2 | 5 |  |  |  |  |  |  |  | 3 | 32 | 1 |  |  |
| W |  |  | 1 |  | 2 |  |  |  |  |  |  |  |  | 1 |  |  |  |
| Y |  | 2 | 2 | 17 | 2 |  |  |  |  |  |  |  |  | 16 | 31 |  |  |
| SUM CHECK | 0 | 99 | 99 | 99 | 100 | 100 | 100 | 100 | 100 | 100 | 100 | 100 | 100 | 100 | 100 | 0 | 0 |

Motif III

| Q2VP16_ECOLI | (A so #age for the most part because mostly 100 sequences in the determination) | | | | | | | | | | | | | | | |
|---|---|---|---|---|---|---|---|---|---|---|---|---|---|---|---|---|
| 100 sequence alignment: Blasted E coli and then from the list returned, removed all below the first non-DEF protein, removed all DEFs with number other than 1 and with precuror assignment | | | | | | | | | | | | | | | | |
| Q2VP16 RESIDUE# | 124 | 125 | 126 | 127 | 128 | 129 | 130 | 131 | 132 | 133 | 134 | 135 | 136 | 137 | 138 | 139 |
| Number of sequences aligned at this residue: | | | | | | | | | | | | | | | | |
|  | 100 | 100 | 100 | 100 | 100 | 100 | 100 | 100 | 100 | 100 | 100 | 100 | 100 | 100 | 100 | 100 |
|  | D | G | L | L | A | I | C | I | Q | H | E | M | D | H | L | V |
| A |  |  |  | 2 | 90 | 1 | 13 |  |  |  |  |  |  |  |  |  |
| C |  |  | 3 |  |  |  | 33 | 1 | 3 |  |  |  |  |  |  |  |
| D |  | 11 |  | 1 |  |  |  |  |  |  |  | 4 | 95 |  |  | 22 |
| E |  | 7 | 26 | 8 | 3 |  |  | 14 |  |  | 97 | 7 | 1 |  | 1 | 7 |
| F |  | 75 |  |  |  |  |  |  |  |  |  |  |  |  |  |  |
| G |  |  |  |  |  |  |  | 2 |  |  |  | 46 | 4 | 92 |  | 6 |
| H |  |  | 3 |  |  | 26 | 11 | 43 |  | 100 | 2 |  |  |  | 8 | 2 |
| I |  |  |  | 1 |  | 2 |  |  |  |  |  |  |  |  |  | 2 |
| K |  |  |  |  |  |  |  |  |  |  |  |  |  |  |  |  |
| L |  |  | 36 | 44 |  | 3 | 6 | 17 | 3 |  |  | 3 |  | 6 | 86 | 5 |
| M |  |  | 1 | 8 |  |  |  | 2 | 4 |  |  | 15 |  |  | 2 |  |
| N |  | 3 |  | 5 |  |  |  |  |  |  |  | 3 |  |  | 1 | 48 |
| P |  |  |  | 15 |  |  |  |  |  |  |  |  |  |  |  |  |
| Q |  |  |  | 1 |  | 1 |  |  | 90 |  |  |  |  | 6 |  | 5 |
| R |  |  |  | 1 |  | 46 |  |  |  |  |  |  |  |  |  |  |
| S |  |  |  |  | 7 | 2 |  |  |  |  |  |  |  |  |  | 2 |
| T |  |  | 1 | 3 |  |  | 37 | 20 |  |  |  | 13 |  |  |  | 1 |
| V |  |  |  | 3 |  |  |  | 1 |  |  |  | 2 |  |  | 2 | 3 |
| W |  |  | 7 |  |  |  |  |  |  |  |  |  |  |  |  |  |
| Y |  |  | 23 | 2 |  |  |  |  |  |  |  |  |  | 1 |  | 1 |
| SUM CHECK | 0 | 100 | 100 | 100 | 100 | 100 | 100 | 100 | 100 | 100 | 100 | 100 | 100 | 100 | 100 | 100 |

FIG. 8, PANEL C

SEQUENCE LISTING

<160> NUMBER OF SEQ ID NOS: 16

<210> SEQ ID NO 1
<211> LENGTH: 193
<212> TYPE: PRT
<213> ORGANISM: Arabidopsis thaliana

<400> SEQUENCE: 1

Lys Asp Asp Lys Val Ala Ser Ala Thr Asp Val Gln Phe Glu Thr Pro
 1               5                  10                  15

Leu Lys Ile Val Glu Tyr Pro Asp Pro Ile Leu Arg Ala Lys Asn Lys
            20                  25                  30

Arg Ile Asp Ile Phe Asp Glu Asn Leu Lys Asn Leu Val Asp Ala Met
        35                  40                  45

Phe Asp Val Met Tyr Lys Thr Asp Gly Ile Gly Leu Ser Ala Pro Gln
    50                  55                  60

Val Gly Leu Asn Val Gln Leu Met Val Phe Asn Pro Ala Gly Glu Pro
65                  70                  75                  80

Gly Glu Gly Lys Glu Ile Val Leu Val Asn Pro Lys Ile Lys Lys Tyr
                85                  90                  95

Ser Asp Lys Leu Val Pro Phe Asp Glu Gly Cys Leu Ser Phe Pro Gly
            100                 105                 110

Ile Tyr Ala Glu Val Val Arg Pro Gln Ser Val Lys Ile Asp Ala Arg
        115                 120                 125

Asp Ile Thr Gly Glu Arg Phe Ser Ile Ser Leu Ser Arg Leu Pro Ala
    130                 135                 140

Arg Ile Phe Gln His Glu Tyr Asp His Leu Glu Gly Val Leu Phe Phe
145                 150                 155                 160

Asp Arg Met Thr Asp Gln Val Leu Asp Ser Ile Arg Glu Glu Leu Glu
                165                 170                 175

Ala Leu Glu Lys Lys Tyr Glu Gly Lys Thr Gly Leu Pro Ser Pro Glu
            180                 185                 190

Arg

<210> SEQ ID NO 2
<211> LENGTH: 14
<212> TYPE: PRT
<213> ORGANISM: Arabidopsis thaliana
<220> FEATURE:
<221> NAME/KEY: MOD_RES
<222> LOCATION: (2)

-continued

```
<223> OTHER INFORMATION: variable residue
<220> FEATURE:
<221> NAME/KEY: MOD_RES
<222> LOCATION: (4)
<223> OTHER INFORMATION: variable residue
<220> FEATURE:
<221> NAME/KEY: MOD_RES
<222> LOCATION: (9)..(14)
<223> OTHER INFORMATION: variable residue

<400> SEQUENCE: 2

Ala Xaa Phe Xaa Glu Gly Cys Leu Xaa Xaa Xaa Xaa Xaa Xaa
 1               5                  10

<210> SEQ ID NO 3
<211> LENGTH: 15
<212> TYPE: PRT
<213> ORGANISM: Arabidopsis thaliana
<220> FEATURE:
<221> NAME/KEY: MOD_RES
<222> LOCATION: (1)..(2)
<223> OTHER INFORMATION: variable residue
<220> FEATURE:
<221> NAME/KEY: MOD_RES
<222> LOCATION: (4)
<223> OTHER INFORMATION: variable residue
<220> FEATURE:
<221> NAME/KEY: MOD_RES
<222> LOCATION: (7)..(8)
<223> OTHER INFORMATION: variable residue
<220> FEATURE:
<221> NAME/KEY: MOD_RES
<222> LOCATION: (10)..(11)
<223> OTHER INFORMATION: variable residue
<220> FEATURE:
<221> NAME/KEY: MOD_RES
<222> LOCATION: (13)..(14)
<223> OTHER INFORMATION: variable residue

<400> SEQUENCE: 3

Xaa Xaa Gly Xaa Gly Leu Xaa Xaa Pro Xaa Xaa Gly Xaa Xaa Val
 1               5                  10                  15

<210> SEQ ID NO 4
<211> LENGTH: 14
<212> TYPE: PRT
<213> ORGANISM: Arabidopsis thaliana
<220> FEATURE:
<221> NAME/KEY: MOD_RES
<222> LOCATION: (1)..(4)
<223> OTHER INFORMATION: variable residue
<220> FEATURE:
<221> NAME/KEY: MOD_RES
<222> LOCATION: (6)
<223> OTHER INFORMATION: variable residue
<220> FEATURE:
<221> NAME/KEY: MOD_RES
<222> LOCATION: (12)..(14)
<223> OTHER INFORMATION: variable residue

<400> SEQUENCE: 4

Xaa Xaa Xaa Xaa Glu Xaa Cys Leu Ser Phe Pro Xaa Xaa Xaa
 1               5                  10

<210> SEQ ID NO 5
<211> LENGTH: 15
<212> TYPE: PRT
<213> ORGANISM: Arabidopsis thaliana
<220> FEATURE:
<221> NAME/KEY: MOD_RES
<222> LOCATION: (1)..(4)
<223> OTHER INFORMATION: variable residue
<220> FEATURE:
```

```
<221> NAME/KEY: MOD_RES
<222> LOCATION: (6)
<223> OTHER INFORMATION: variable residue
<220> FEATURE:
<221> NAME/KEY: MOD_RES
<222> LOCATION: (11)
<223> OTHER INFORMATION: variable residue
<220> FEATURE:
<221> NAME/KEY: MOD_RES
<222> LOCATION: (13)
<223> OTHER INFORMATION: variable residue

<400> SEQUENCE: 5

Xaa Xaa Xaa Xaa Arg Xaa Phe Gln His Glu Xaa Asp Xaa Leu Gln
 1               5                  10                  15

<210> SEQ ID NO 6
<211> LENGTH: 18
<212> TYPE: PRT
<213> ORGANISM: Arabidopsis thaliana

<400> SEQUENCE: 6

Arg Leu Ala Pro Gly Val Gly Leu Ala Ala Pro Gln Ile Gly Val Pro
 1               5                  10                  15

Leu Arg

<210> SEQ ID NO 7
<211> LENGTH: 18
<212> TYPE: PRT
<213> ORGANISM: Arabidopsis thaliana

<400> SEQUENCE: 7

Lys Lys Ala Leu Phe Phe Glu Gly Cys Leu Ser Val Asp Gly Phe Arg
 1               5                  10                  15

Ala Ala

<210> SEQ ID NO 8
<211> LENGTH: 18
<212> TYPE: PRT
<213> ORGANISM: Arabidopsis thaliana

<400> SEQUENCE: 8

Ala Ser Gly Trp Gln Ala Arg Ile Leu Gln His Glu Cys Asp His Leu
 1               5                  10                  15

Asp Gly

<210> SEQ ID NO 9
<211> LENGTH: 18
<212> TYPE: PRT
<213> ORGANISM: Arabidopsis thaliana

<400> SEQUENCE: 9

Lys Thr Asp Gly Ile Gly Leu Ser Ala Pro Gln Val Gly Leu Asn Val
 1               5                  10                  15

Gln Leu

<210> SEQ ID NO 10
<211> LENGTH: 18
<212> TYPE: PRT
<213> ORGANISM: Arabidopsis thaliana

<400> SEQUENCE: 10

Leu Val Pro Phe Asp Glu Gly Cys Leu Ser Phe Pro Gly Ile Tyr Ala
 1               5                  10                  15
```

Glu Val

<210> SEQ ID NO 11
<211> LENGTH: 18
<212> TYPE: PRT
<213> ORGANISM: Arabidopsis thaliana

<400> SEQUENCE: 11

Ser Ser Leu Pro Ala Arg Ile Phe Gln His Glu Tyr Asp His Leu Glu
 1               5                  10                  15

Gly Val

<210> SEQ ID NO 12
<211> LENGTH: 18
<212> TYPE: PRT
<213> ORGANISM: Escherichia coli

<400> SEQUENCE: 12

Tyr Ala Glu Lys Gly Ile Gly Leu Ala Ala Thr Gln Val Asp Ile His
 1               5                  10                  15

Gln Arg

<210> SEQ ID NO 13
<211> LENGTH: 18
<212> TYPE: PRT
<213> ORGANISM: Escherichia coli

<400> SEQUENCE: 13

Gly Glu Thr Gly Ile Glu Glu Gly Cys Leu Ser Ile Pro Glu Gln Arg
 1               5                  10                  15

Ala Leu

<210> SEQ ID NO 14
<211> LENGTH: 18
<212> TYPE: PRT
<213> ORGANISM: Escherichia coli

<400> SEQUENCE: 14

Ala Asp Gly Leu Leu Ala Ile Cys Ile Gln His Glu Met Asp His Leu
 1               5                  10                  15

Val Gly

<210> SEQ ID NO 15
<211> LENGTH: 5
<212> TYPE: PRT
<213> ORGANISM: Arabidopsis thaliana

<400> SEQUENCE: 15

Glu Gly Cys Leu Ser
 1               5

<210> SEQ ID NO 16
<211> LENGTH: 6
<212> TYPE: PRT
<213> ORGANISM: Arabidopsis thaliana
<220> FEATURE:
<221> NAME/KEY: MOD_RES

```
-continued

<222> LOCATION: (4)..(5)
<223> OTHER INFORMATION: variable residue

<400> SEQUENCE: 16

Gln His Glu Xaa Xaa His
  1               5
```

US 7,445,923 B2

CRYSTALLIZATION AND STRUCTURE OF A PLANT PEPTIDE DEFORMYLASE

CROSS REFERENCE TO RELATED APPLICATIONS

This application claims priority to U.S. Provisional Application Ser. No. 60/835,823 filed Aug. 4, 2006, the disclosure of which is incorporated herein by reference.

STATEMENTS REGARDING FEDERALLY SPONSORED RESEARCH

The invention was funded in part by Grant No. MCB-MCB-0240165 awarded by the National Science Foundation (NSF). The government may have certain rights in the invention.

TECHNICAL FIELD

This invention relates to the crystallization and structure of plant peptide deformylase and methods of using the structure.

BACKGROUND

Peptide deformylase (DEF; EC 3.5.1.88) is a metallopeptidase that catalyzes the removal of an N-formyl group from N-formyl methionine, which is the initiating amino acid residue for prokaryotically translated proteins. DEF is an essential enzyme and mutations, deletions, or insertions in the DEF gene, or inhibition of enzymatic activity, are lethal to prokaryotic organisms. For decades DEF was believed to be exclusively restricted to prokaryotes because protein translation in eukaryotic organisms initiates with an unformylated methionine residue. The restriction to prokaryotic organisms and the essentiality of DEF have made this enzyme the molecular target of many research efforts directed towards the development of broad-spectrum antibiotics, which would have little or no mammalian toxicity. In 2000 the existence of DEF in the chloroplasts of higher plants was reported, and it was also discovered that actinonin, a potent inhibitor of DEF, was phytotoxic to all plant species. The lethality of actinonin to a wide range of plants, including many agriculturally significant weed species, suggests that DEF is an essential and highly conserved enzyme in plants, and inhibitors targeting this enzyme could potentially serve as a new class of broad-spectrum herbicides as well as selectable markers.

Accordingly, plant peptide deformylase (DEF) polypeptides provide an attractive target for crystallization and structural studies which can lead to the identification and synthesis of new broad-spectrum herbicides and selectable markers with high specificity towards plant DEF.

SUMMARY

Provided herein are crystalline forms of a peptide deformylase, and atomic coordinates derived therefrom, useful for designing and identifying compounds that modulate the activity of the peptide deformylase. Accordingly, in one embodiment, a crystalline form of a polypeptide comprising the amino acid residues of SEQ ID NO:1, is provided. In some aspects, the crystalline form includes a structure characterized by tetragonal space group symmetry $P4_12_12$ and unit cell of dimensions a, b, and c. In some aspects, a is about 40 Å to about 60 Å, b is about 40 Å to about 60 Å, and c is about 120 Å to about 160 Å. In other aspects, $\alpha=\beta=\gamma=90°$. In some aspects, the polypeptide is a peptide deformylase isolated from Arabidopsis thaliana.

In some embodiments, the crystalline form includes a coordinated metal ion selected from the group of consisting of Fe, Zn, and Ni, and any combination thereof. In one aspect, the metal ion is coordinated by amino acid residues Cys171, His213, and His217 of SEQ ID NO:1.

In another embodiment, a crystalline form of a polypeptide including a structure defined by one or more structure coordinates of Arabidopsis thaliana peptide deformylase amino acid residues Gly121, Gly123, Leu124, Gln128, Glu169, Gly170, Cys171, Leu172, His213, Glu214, His217, and Tyr178 according to Table 1, is provided. In general, structures derived from these crystalline forms encompass structures having coordinates that differ by a root mean square deviation of less than about 1.5 Å, 0.75 Å, or 0.35 Å, or any deviation in this range, when superimposed on the non-hydrogen atom positions of the corresponding atomic coordinates of Table 1. In some aspects, amino acid residues Gly121, Gly123, Leu124, Gln128, Glu169, Gly170, Cys171, Leu172, His213, Glu214, His217, and Tyr178 include the active site of the peptide deformylase. In some aspects, the polypeptide includes an amino acid sequence having at least 75%, at least 85%, or at least 95%, or any percent in this range, amino acid sequence identity to SEQ ID NO:1.

In other embodiments, a crystalline form of a polypeptide provided herein also includes a ligand complexed with the polypeptide. In some aspects, the ligand is a small molecule.

In another embodiment, a crystalline form of a polypeptide that includes the amino acid residues of SEQ ID NO:1 and an atomic structure characterized by the coordinates of Table 1, is provided.

In yet another embodiment, a machine-readable medium embedded with information that corresponds to a three-dimensional structural representation of a crystalline form of a polypeptide as provided herein.

In one embodiment, a computer system including a database containing information on the three dimensional structure of a crystalline form of an Arabidopsis thaliana peptide deformylase polypeptide and a user interface to view the information, is provided. In some aspects, the computer system includes information related to diffraction data obtained from a crystalline form comprising SEQ ID NO:1. In other aspects, the computer system of includes information related to an electron density map of a crystal comprising SEQ ID NO:1.

In another aspect, a computer system provided herein includes information related to the structure coordinates of Table 1 or homologous structure coordinates for the amino acid residues of SEQ ID NO:1 that have a root mean square deviation of non-hydrogen atoms of less than about 1.5 Å, 0.75 Å, 0.35 Å, or any percent in this range, when superimposed on the non-hydrogen atom positions of the corresponding atomic coordinates of Table 1.

In other aspects, a computer system provided herein includes information related to the structure coordinates for one or more amino acid residues Gly121, Gly123, Leu124, Gln128, Glu169, Gly170, Cys171, Leu172, His213, Glu214, His217, and Tyr178 according to Table 1, or similar structure coordinates for the amino acids including a root mean square deviation of non-hydrogen atoms of less than about 1.5 Å, 0.75 Å, 0.35 Å, or any percent in this range, when superimposed on the non-hydrogen atom positions of the corresponding atomic coordinates of Table 1.

In another embodiment, a method of identifying a candidate compound that binds to the active site of Arabidopsis thaliana peptide deformylase polypeptide, is provided. The method includes comparing the atomic structure of the compound with a three-dimensional structure of a crystalline form of an *Arabidopsis thaliana* peptide deformylase polypeptide and computationally identifying a candidate compound for an ability to bind to the *Arabidopsis thaliana* peptide deformylase. In some aspects, the candidate compound binds to the active site of the *Arabidopsis thaliana* peptide deformylase. In other aspects, comparing the atomic structure of the compound with a three-dimensional structure of a crystalline form of an *Arabidopsis thaliana* peptide deformylase polypeptide includes employing a computational means to perform a fitting operation between the compound and at least one binding site of the peptide deformylase.

In some embodiments, the candidate compound identified by a computational method provided herein can be synthesized and screened for the ability to bind a plant peptide deformylase in vitro or in vivo. In some aspects, the compound is an herbicide.

In another embodiment, a method of identifying a candidate compound that binds to the active site of *Arabidopsis thaliana* peptide deformylase polypeptide, is provided. The method includes comparing the atomic structure of the compound with a three-dimensional structural representation of a crystalline form provided herein and computationally identifying a candidate compound for an ability to bind to the active site of *Arabidopsis thaliana* peptide deformylase.

In yet another embodiment, a method of computationally designing a candidate compound that binds to *Arabidopsis thaliana* peptide deformylase polypeptide, is provided. The method includes comparing the atomic structure of chemical entities, or fragments thereof, with a three-dimensional structural representation of a crystalline form of a polypeptide provided herein; identifying chemical entities capable of associating with the three-dimensional structural representation of a crystalline form of a polypeptide; and assembling the chemical entities, or fragments thereof, into a single molecule to provide the structure of the candidate compound. In some aspects, the candidate compound binds to the active site of *Arabidopsis thaliana* peptide deformylase.

In another embodiment, a method of identifying a region of *Arabidopsis thaliana* peptide deformylase polypeptide that contacts a compound, is provided. The method includes obtaining X-ray diffraction data for a crystal of *Arabidopsis thaliana* peptide deformylase; obtaining X-ray diffraction data for a complex of a *Arabidopsis thaliana* peptide deformylase and the compound; subtracting the X-ray diffraction data from the peptide deformylase with the X-ray diffraction data obtained from the complex to obtain the difference in the X-ray diffraction data; obtaining phases that correspond to X-ray diffraction data obtained for the peptide deformylase; correlating the data to generate a difference Fourier image of the compound; and locating the region of *Arabidopsis thaliana* peptide deformylase contacted by the compound. In some aspects, the compound is actinonin.

In another embodiment, a method of modifying an inhibitor of *Arabidopsis thaliana* peptide deformylase activity, is provided. The method includes obtaining a crystal including an *Arabidopsis thaliana* peptide deformylase polypeptide and an inhibitor; obtaining the atomic coordinates of the crystal; correlating the atomic coordinate data with one or more molecular modeling techniques; identifying at least one modification predicted to effect the interaction of the inhibitor with the polypeptide; and modifying the inhibitor based on the prediction. In one aspect, the modification is a computer generated modification. In other aspects, the modification is a physical modification made to the structure of the inhibitor. In one aspect, the crystal comprises the amino acid residues of SEQ ID NO:1.

In other aspects, the one or more molecular modeling techniques are selected from the group consisting of graphic molecular modeling and computational chemistry. In another aspect, obtaining the atomic coordinates of the crystal includes detecting the interaction of the inhibitor to one or more amino acid residues Gly121, Gly123, Leu124, Gln128, Glu169, Gly170, Cys171, Leu172, His213, Glu214, His217, and Tyr178 of SEQ ID NO:1.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

FIG. 6 depicts a phylogenetic analyses comparing Motif 1 (SEQ ID NO: 6), Motif 2 (SEQ ID NO: 7) and Motif 3 (SEQ ID NO: 8) of plant AtDEF1 peptide deformylase with the amino acid sequence of other peptide deformylase sequences.

FIG. 7 depicts a phylogenetic analyses comparing Motif 1 (SEQ ID NO: 9), Motif 2 (SEQ ID NO: 10) and Motif 3 (SEQ ID NO: 11) of plant AtDEF2 peptide deformylase with the amino acid sequence of other peptide deformylase sequences.

FIG. 8 depicts a phylogenetic analyses comparing Motif 1 (SEQ ID NO: 12), Motif 2 (SEQ ID NO: 13) and Motif 3 (SEQ ID NO: 14) of various peptide deformylase amino acid sequences.

Like reference symbols in the various drawings indicate like elements.

DETAILED DESCRIPTION

Figures 1A, 1B:
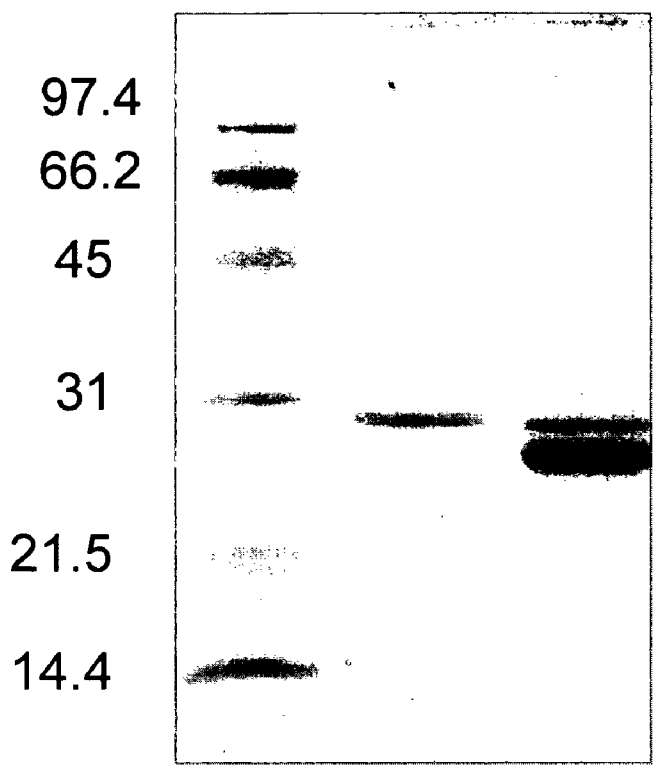
FIG. 1A depicts a polyacrylamide gel showing that limited trypsinolysis creates a core protein that retained activity and remained soluble in the absence of high salt concentrations.
FIG. 1B depicts the amino acid sequence of the AtDEF peptide (SEQ ID NO: 1).

Provided herein are novel crystalline forms of peptide deformylase polypeptides and atomic coordinate information related to such crystals. Also provided are methods of using such information to identify, design and/or modify compounds that modulate the activity of a peptide deformylase. In addition, computer systems that include such information are provided. The crystal structures and information derived therefrom are suitable for designing and identifying, for example, broad spectrum herbicides. Such herbicides can be used, for example, to inhibit or prevent the growth of undesirable vegetation.

The crystal structure is based, at least in part, on the discovery of a plant nuclear gene that encodes a chloroplast targeted peptide deformylase polypeptide. The gene has substantial homology to bacterial peptide deformylase. The deduced translation of this nucleic acid sequence reveals the presence of three conserved protein motifs associated with prokaryotic peptide deformylase (see e.g., FIGS. 6, 7, and 8). Nucleic acid and amino acid sequences for plant peptide deformylases are disclosed in U.S. Pat. No. 6,730,634, issued May 4, 2004, and U.S. Patent Application Publication No. 20040088755, the contents of which are incorporated herein by reference.

It is to be understood that the crystalline form of a plant peptide deformylase from which the atomic structure coordinates of the invention can be obtained is not limited to wild-type *Arabidopsis thaliana* peptide deformylase polypeptide, or a truncated form of the polypeptide (see e.g., SEQ ID NO:1) as provided herein. Indeed, the crystals may comprise mutants of wild-type *Arabidopsis thaliana* peptide deformylase or the sequence of amino acids set forth in SEQ ID NO:1. Mutants can be obtained by replacing at least one amino acid residue in the sequence of the wild-type *Arabidopsis thaliana* peptide deformylase or the sequence of amino acids set forth in SEQ ID NO:1 with a different amino acid residue, or by adding or deleting one or more amino acid residues within the wild-type sequence and/or at the N- and/or C-terminus of the wild-type *Arabidopsis thaliana* peptide deformylase or the sequence of amino acids set forth in SEQ ID NO:1. Preferably, such mutants will crystallize under crystallization conditions that are substantially similar to those used to crystallize the wild-type *Arabidopsis thaliana* peptide deformylase or the sequence of amino acids set forth in SEQ ID NO:1.

The types of mutants contemplated by this invention include conservative mutants, non-conservative mutants, deletion mutants, truncated mutants, extended mutants, methionine mutants, selenomethionine mutants, cysteine mutants and selenocysteine mutants. A mutant may have, but need not have, *Arabidopsis thaliana* peptide deformylase activity. Preferably, a mutant displays biological activity that is substantially similar to that of the wild-type polypeptide or that of SEQ ID NO:1.

It will be recognized by one of skill in the art that the types of mutants contemplated herein are not mutually exclusive; that is, for example, a polypeptide having a conservative mutation in one amino acid may in addition have a truncation of residues at the N-terminus.

In addition, conservative or non-conservative amino acid substitutions can be made to amino acids of wild-type *Arabidopsis thaliana* peptide deformylase or the sequence of amino acids set forth in SEQ ID NO:1 that are implicated in the active site of the polypeptide (e.g., amino acid residues Gly121, Gly123, Leu124, Gln128, Glu169, Gly170, Cys171, Leu172, His213, Glu214, His217, and Tyr178 of SEQ ID NO:1). Such conservative or non-conservative substitutions can affect, e.g., the affinity with which wild-type *Arabidopsis thaliana* peptide deformylase or the sequence of amino acids set forth in SEQ ID NO:1 binds to a substrate. In certain embodiments, the conservative or non-conservative amino acid substitutions can increase the affinity with which wild-type *Arabidopsis thaliana* peptide deformylase or the sequence of amino acids set forth in SEQ ID NO:1 binds to a substrate.

Conservative amino acid substitutions are well-known in the art, and include substitutions made on the basis of a similarity in polarity, charge, solubility, hydrophobicity and/or the hydrophilicity of the amino acid residues involved. Typical conservative substitutions are those in which the amino acid is substituted with a different amino acid that is a member of the same class or category, as those classes are defined herein. Thus, typical conservative substitutions include aromatic to aromatic, apolar to apolar, aliphatic to aliphatic, acidic to acidic, basic to basic, polar to polar, etc. Other conservative amino acid substitutions are well known in the art. It will be recognized by those of skill in the art that generally, a total of about 20% or fewer, typically about 10% or fewer, most usually about 5% or fewer, of the amino acids in the wild-type polypeptide sequence can be conservatively substituted with other amino acids without deleteriously affecting the biological activity and/or three-dimensional structure of the molecule, provided that such substitutions do not involve residues that are critical for activity. The following abbreviations are used for amino acids throughout this disclosure: A=Ala=Alanine, T=Thr=Threonine, V=Val=Valine, C=Cys=Cysteine, L=Leu=Leucine, Y=Tyr=Tyrosine, I=Ile=Isoleucine, N=Asn=Asparagine, P=Pro=Proline, Q=Gln=Glutamine, F=Phe=Phenylalanine, D=Asp=Aspartic Acid, W=Trp=Tryptophan, E=Glu=Glutamic Acid, M=Met=Methionine, K=Lys=Lysine, G=Gly=Glycine, R=Arg=Arginine, S=Ser=Serine, H=His=Histidine.

In some embodiments, it may be desirable to make mutations in the active site of a polypeptide, e.g., to reduce or completely eliminate deformylase activity. Mutations that will reduce or completely eliminate the activity of a particular protein will be apparent to those of skill in the art. For example, the amino acids identified in Table 1 could be mutated in order to reduce or eliminate the binding activity of wild-type *Arabidopsis thaliana* peptide deformylase or the sequence of amino acids set forth in SEQ ID NO:1.

The amino acid residue Cys (C) is unusual in that it can form disulfide bridges with other Cys (C) residues or other sulfhydryl-containing amino acids ("cysteine-like amino acids"). The ability of Cys (C) residues and other cysteine-like amino acids to exist in a polypeptide in either the reduced free —SH or oxidized disulfide-bridged form affects whether Cys (C) residues contribute net hydrophobic or hydrophilic character to a polypeptide.

While in most instances the amino acids of wild-type *Arabidopsis thaliana* peptide deformylase or the sequence of amino acids set forth in SEQ ID NO:1 will be substituted with genetically-encoded amino acids, in certain circumstances mutants may include genetically non-encoded amino acids. Alternatively, in instances where the mutant will be prepared in whole or in part by chemical synthesis, virtually any non-encoded amino acids may be used, ranging from D-isomers of the genetically encoded amino acids to non-encoded naturally-occurring natural and synthetic amino acids.

Conservative amino acid substitutions for many of the commonly known non-genetically encoded amino acids are well known in the art. Conservative substitutions for other non-encoded amino acids can be determined based on their physical properties as compared to the properties of the genetically encoded amino acids.

In some instances, it may be particularly advantageous or convenient to substitute, delete from and/or add amino acid residues to wild-type *Arabidopsis thaliana* peptide deformylase or the sequence of amino acids set forth in SEQ ID NO:1 in order to provide convenient cloning sites in cDNA encoding the polypeptide, to aid in purification of the polypeptide, etc. Such substitutions, deletions and/or additions that do not substantially alter the three dimensional structure of the native *Arabidopsis thaliana* peptide deformylase or the sequence of amino acids set forth in SEQ ID NO:1 will be apparent to those having skills in the art. These substitutions, deletions and/or additions include, but are not limited to, His tags, BirA tags, intein-containing self-cleaving tags, maltose binding protein fusions, glutathione S-transferase protein fusions, antibody fusions, green fluorescent protein fusions, signal peptide fusions, biotin accepting peptide fusions, and the like.

Mutations may also be introduced into a polypeptide sequence where there are residues, e.g., cysteine residues, that interfere with crystallization. Such cysteine residues can be substituted with an appropriate amino acid that does not readily form covalent bonds with other amino acid residues under crystallization conditions; e.g., by substituting the cysteine with Ala, Ser or Gly. Any cysteine located in a non-helical or non-beta-stranded segment, based on secondary structure assignments, are good candidates for replacement.

It should be noted that the mutants contemplated herein need not exhibit deformylase activity. Indeed, amino acid substitutions, additions or deletions that interfere with the binding activity of wild-type *Arabidopsis thaliana* peptide deformylase or the sequence of amino acids set forth in SEQ ID NO:1 are specifically contemplated by the invention. Such crystalline polypeptides, or the atomic structure coordinates obtained therefrom, can be used to provide phase information to aid the determination of the three-dimensional X-ray structures of other related or non-related crystalline polypeptides.

Also contemplated are homologs of the *Arabidopsis thaliana* peptide deformylase. The present invention provides a computer-assisted method for homology modeling an *Arabidopsis thaliana* peptide deformylase homolog including: aligning the amino acid sequence of an *Arabidopsis thaliana* peptide deformylase homolog with the amino acid sequence of *Arabidopsis thaliana* peptide deformylase SEQ ID NO:1 and incorporating the sequence of the *Arabidopsis thaliana* peptide deformylase homolog into a model of *Arabidopsis thaliana* peptide deformylase derived from structure coordinates set forth in Table 1 to yield a preliminary model of the *Arabidopsis thaliana* peptide deformylase homolog; subjecting the preliminary model to energy minimization to yield an energy minimized model; remodeling regions of the energy minimized model where stereochemistry restraints are violated to yield a final model of the *Arabidopsis thaliana* peptide deformylase homolog.

As used herein, the term "homolog" refers to the polypeptide molecule or the nucleic acid molecule which encodes the polypeptide, or a functional domain from said polypeptide from a first source having at least about 30%, 40% or 50% sequence identity, or at least about 60%, 70% or 75% sequence identity, or at least about 80% sequence identity, or more preferably at least about 85% sequence identity, or even more preferably at least about 90% sequence identity, and most preferably at least about 95%, 97% or 99% amino acid or nucleotide sequence identity, with the polypeptide, encoding nucleic acid molecule or any functional domain thereof, from a second source. The second source may be a version of the molecule from the first source that has been genetically altered by any available means to change the primary amino acid or nucleotide sequence or may be from the same or a different species than that of the first source. Homology modeling is further discussed below.

Accordingly, provided herein are crystalline forms of a plant peptide deformylase. Referring to FIG. 1A, limited trypsinolysis creates a core protein that retained activity and remained soluble in the absence of high salt concentrations. Analysis of wild-type and proteolyzed AtDEF2 on an 8-16% gradient SDS-PAGE. Trypsinolysis produces a truncated DEF2 with a mobility shift corresponding to a 3 kDa loss in molecular mass from AtDEF2, a 24.598 kDa enzyme. The truncated DEF2, which loses its hexahistidyl sequence, was subsequently separated from undigested DEF2 by loading the digested sample onto a HiTrap® affinity column (Amersham Pharmacia) and collecting the flowthrough. Undigested DEF2 remained bound to the column. Referring to FIG. 1B, the amino acid sequence of the truncated DEF2 polypeptide is provided.

It is understood that the term "crystalline form" includes a polypeptide associated with a plant peptide deformylase can include just the polypeptide, or the polypeptide complexed with a metal, a ligand, or any other chemical entity suitable for crystallization with the polypeptide. An exemplary polypeptide includes *Arabidopsis thaliana* peptide deformylase, or fragments thereof, suitable for crystallization. Such fragments include optionally, the crystal may include a coordinated metal ion selected from the group of consisting of Fe, Zn, Ni, or combinations thereof. Thus, "crystalline form" and "crystal" refer to a composition comprising a polypeptide complex in crystalline form. The term "crystal" includes native crystals, heavy-atom derivative crystals and poly-crystals. "Native Crystal" refers to a crystal wherein the polypeptide complex is substantially pure.

Figure 2A:
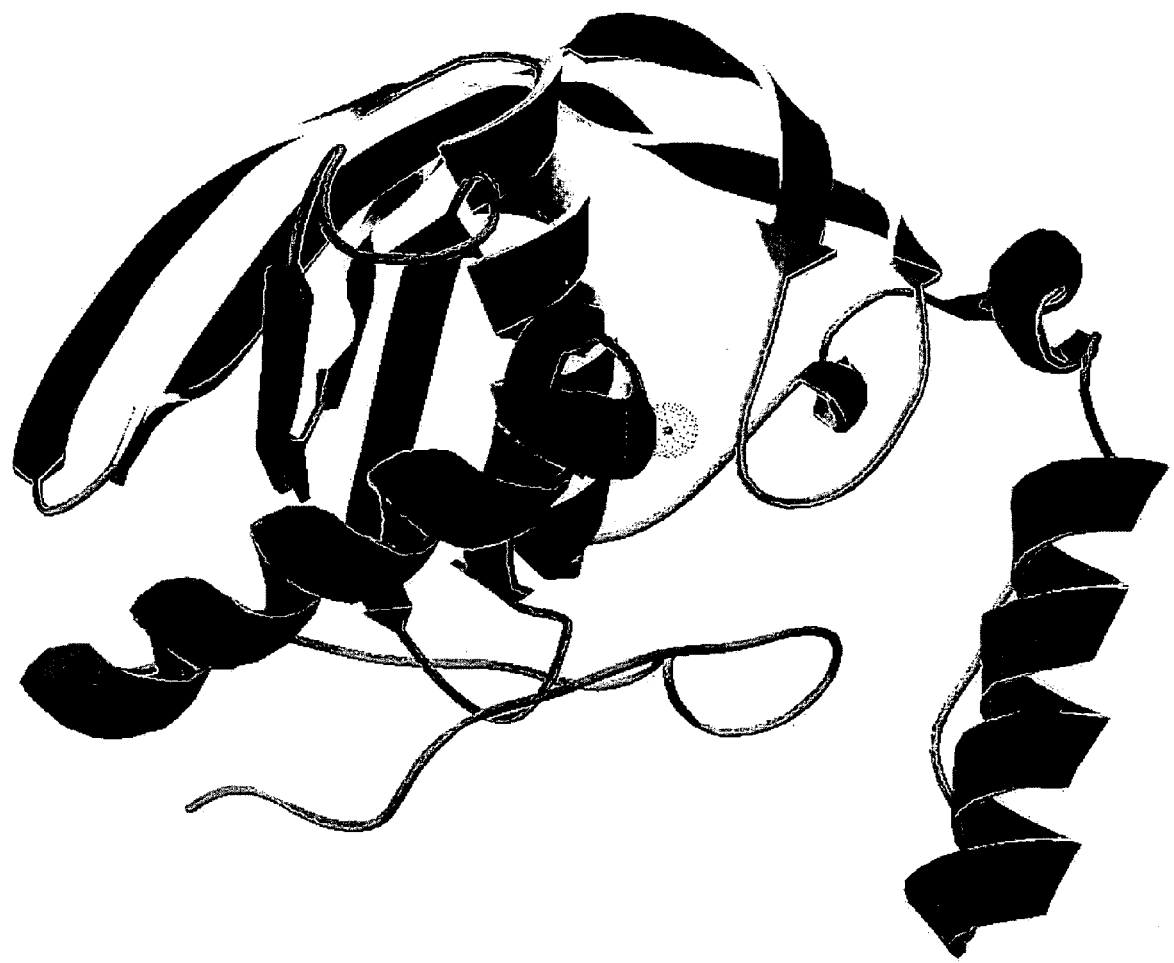
FIG. 2A depicts a ribbon representation of crystallized AtDEF2. The cylinders represent helices and the arrows represent sheets.

Referring to FIG. 2A, the crystal structure of DEF2 was determined by molecular replacement and refined to a resolution of 2.7 Å. "Molecular Replacement" refers to the method of calculating initial phases for a new crystal of a polypeptide whose structure coordinates are unknown by orienting and positioning a polypeptide whose structure coordinates are known within the unit cell of the new crystal so as to best account for the observed diffraction pattern of the new crystal. Phases are then calculated from the oriented and positioned polypeptide and combined with observed amplitudes to provide an approximate Fourier synthesis of the structure of the polypeptides comprising the new crystal (Jones et al., 1991, Acta Crystallogr. 47:753-70; Brunger et al., 1998, Acta Crystallogr. D. Biol. Crystallogr. 54:905-21).

Figure 2B:
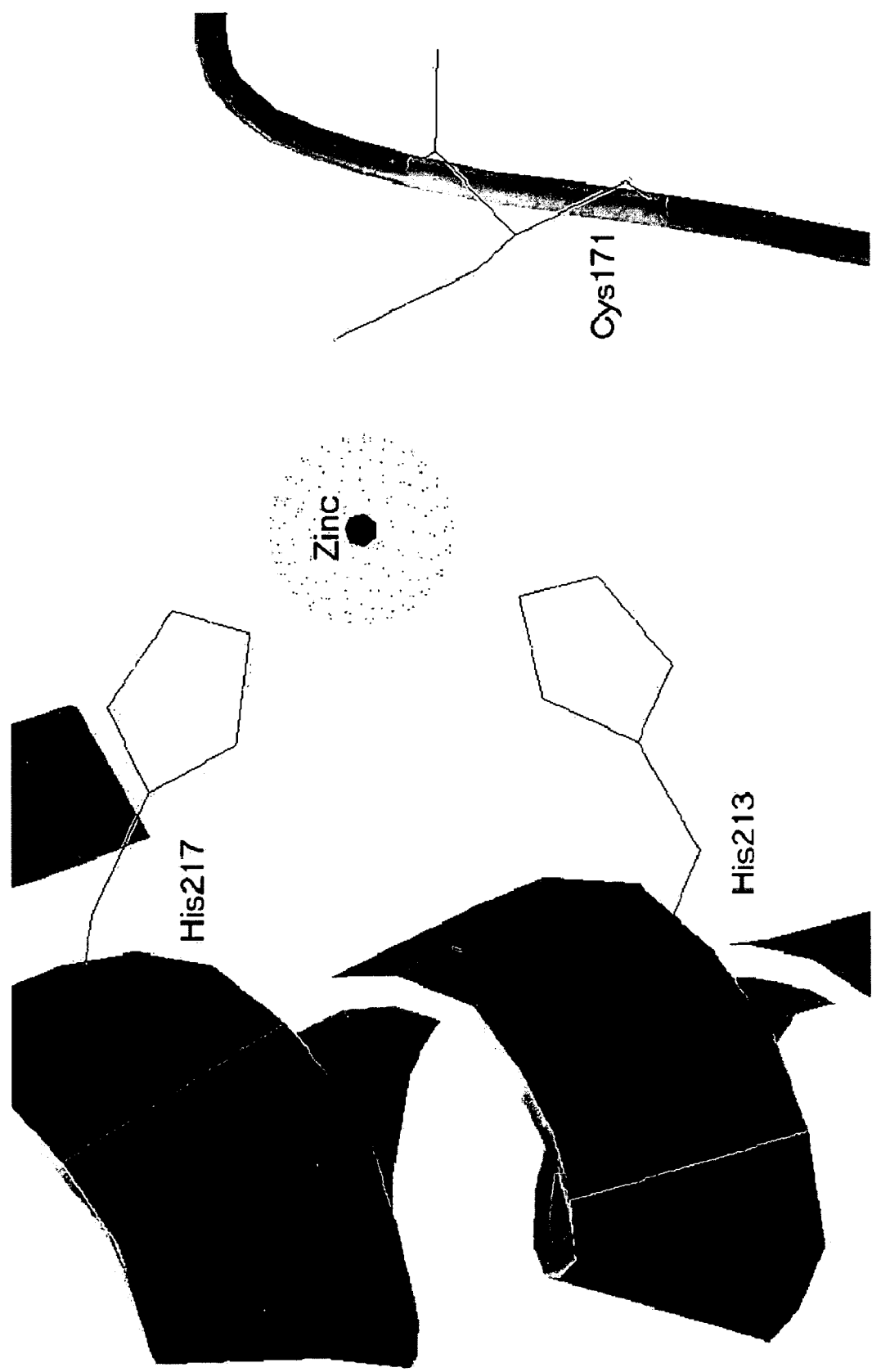
FIG. 2B depicts a slab view of the ribbon representation of trypsinolyzed AtDEF2 highlighting the active-site-metal binding ligands (1 Cys and 2 His) from motifs II and III, respectively (EGCLS and QHEXXH) (SEQ ID NOS 15-16).

The overall fold of the enzyme resembles the α+β conformation of known bacterial peptide deformylases, with an r.m.s deviation of about 1.04 Å on main chain atoms relative to the *E. coli* enzyme. The largest differences occur in the orientation of the C-terminal helix (helix 3) and the conformation of the loop between β strands 2 and 3, which form part of the five-stranded central sheet. Motif I, II and III are colored blue, green and pink, respectively. The active site metal, modeled as zinc due to the conditions of crystallization, is a space-filled sphere in the middle of the structure. Referring to FIG. 2B, a slab view of the ribbon representation of trypsinolyzed AtDEF2 highlighting the active-site-metal binding ligands (1 Cys and 2 His) from motifs II and III, respectively (EGCLS (SEQ ID NO: 2) and QHEXXH (SEQ ID NO: 3) is provided. As used herein, the term "active site" refers to regions on a protein or a structural motif of a protein that are directly involved in the function or activity of the peptide deformylase.

As used herein, the terms "binding site" or "binding pocket" refer to a region of a polypeptide or a molecular complex comprising the polypeptide that, as a result of the primary amino acid sequence of the polypeptide and/or its three-dimensional shape, favorably associates with another chemical entity or compound including ligands or inhibitors.

The crystalline form can include the tetragonal space group symmetry $P4_12_12$ and includes a unit cell having dimensions a, b, and c; wherein a is about 40 Å to about 60 Å, b is about 40 Å to about 60 Å, and c is about 120 Å to about 160 Å; and wherein alpha=beta=gamma=90 degree. In some aspects, a is about 49 Å to about 52 Å, b is about 49 Å to about 52 Å, and c is about 143 Å to about 147 Å.

"Unit Cell" refers to the smallest and simplest volume element (i.e., parallel piped-shaped block) of a crystal that is completely representative of the unit or pattern of the crystal, such that the entire crystal can be generated by translation of the unit cell. The dimensions of the unit cell are defined by six numbers: dimensions a, b and c and angles α, β and γ (Blundel et al., 1976, Protein Crystallography, Academic Press). A crystal is an efficiently packed array of many unit cells. "Tetragonal Unit Cell" refers to a unit cell in which a≠b≠c; and α=β=γ90°. "Crystal lattice" refers to the array of points defined by the vertices of packed unit cells. "Space group" refers to the set of symmetry operations of a unit cell. In a space group designation (e.g., $C_2$) the capital letter indicates the lattice type and the other symbols represent symmetry operations that can be carried out on the unit cell without changing its appearance. "Asymmetric Unit" refers to the largest aggregate of molecules in the unit cell that possesses no symmetry elements that are part of the space group symmetry, but that can be juxtaposed on other identical entities by symmetry operations.

When a crystal is placed in an X-ray beam, the incident X-rays interact with the electron cloud of the molecules that make up the crystal, resulting in X-ray scatter. The combination of X-ray scatter with the lattice of the crystal gives rise to nonuniformity of the scatter; areas of high intensity are called diffracted X-rays. The angle at which diffracted beams emerge from the crystal can be computed by treating diffraction as if it were reflection from sets of equivalent, parallel planes of atoms in a crystal (Bragg's Law). The most obvious sets of planes in a crystal lattice are those that are parallel to the faces of the unit cell. These and other sets of planes can be drawn through the lattice points. Each set of planes is identified by three indices, hkl. The h index gives the number of parts into which the a edge of the unit cell is cut, the k index gives the number of parts into which the b edge of the unit cell is cut, and the l index gives the number of parts into which the c edge of the unit cell is cut by the set of hkl planes. Thus, for example, the 235 planes cut the a edge of each unit cell into halves, the b edge of each unit cell into thirds, and the c edge of each unit cell into fifths. Planes that are parallel to the bc face of the unit cell are the 100 planes; planes that are parallel to the ac face of the unit cell are the 010 planes; and planes that are parallel to the ab face of the unit cell are the 001 planes.

When a detector is placed in the path of the diffracted X-rays, in effect cutting into the sphere of diffraction, a series of spots, or reflections, are recorded to produce a "still" diffraction pattern. Each reflection is the result of X-rays reflecting off one set of parallel planes, and is characterized by an intensity, which is related to the distribution of molecules in the unit cell, and hkl indices, which correspond to the parallel planes from which the beam producing that spot was reflected. If the crystal is rotated about an axis perpendicular to the X-ray beam, a large number of reflections is recorded on the detector, resulting in a diffraction pattern.

The unit cell dimensions and space group of a crystal can be determined from its diffraction pattern. First, the spacing of reflections is inversely proportional to the lengths of the edges of the unit cell. Therefore, if a diffraction pattern is recorded when the X-ray beam is perpendicular to a face of the unit cell, two of the unit cell dimensions may be deduced from the spacing of the reflections in the x and y directions of the detector, the crystal-to-detector distance, and the wavelength of the X-rays. Those of skill in the art will appreciate that, in order to obtain all three unit cell dimensions, the crystal can be rotated such that the X-ray beam is perpendicular to another face of the unit cell. Second, the angles of a unit cell can be determined by the angles between lines of spots on the diffraction pattern. Third, the absence of certain reflections and the repetitive nature of the diffraction pattern, which may be evident by visual inspection, indicate the internal symmetry, or space group, of the crystal. Therefore, a crystal may be characterized by its unit cell and space group, as well as by its diffraction pattern.

Once the dimensions of the unit cell are determined, the likely number of polypeptides in the asymmetric unit can be deduced from the size of the polypeptide, the density of the average protein, and the typical solvent content of a protein crystal, which is usually in the range of 30-70% of the unit cell volume (Matthews, 1968, J. Mol. Biol. 33:491-497).

The diffraction pattern of a crystal is related to the three-dimensional shape of the molecules that constitute the crystal by a Fourier transform. It has been established that diffraction patterns of a crystal can result from X-ray diffraction as well as Laue, electron or neutron diffraction. X-ray diffraction has been the most widely used methods for determining macromolecular structures. It is therefore used by way of illustration to discuss the processes of diffraction data collection and subsequent structure determination. The scope of the present invention is, however, by no means limited only to X-ray diffraction analyses of crystalline forms of polypeptides. After enough diffraction data are collected for a crystal, the process of determining the solution is in essence a re-focusing of the diffracted X-rays to produce a three-dimensional image of the molecule in the crystal. Since lenses capable of focusing X-ray radiation do not yet exist, the structure determination can be done via mathematical operations that simulate the re-focusing process.

"X-ray Diffraction" refers to a type of wave interference created when high energy X-ray radiation interacts with any obstruction in its traveling path. The obstruction is often in the form of a crystal of protein, nucleic acid, or inorganic compound. The electrons that surround the atoms in the crystal, rather than the atomic nuclei, are the entities which physically interact with the incoming X-ray photons. When X-ray radiation hits the atoms in a crystal, they make the electronic clouds of the atoms move as does any electromagnetic wave. The re-emitted X-ray radiation gives rise to constructive or destructive interferences. This phenomenon is called X-ray diffraction. In X-ray crystallography, the X-ray diffraction patterns of closely spaced lattices of atoms in the crystal are recorded and then analyzed to reveal the structural nature of the crystal. For example, the spacing between the crystal lattices can be determined using Bragg's law. X-ray diffraction is widely used in chemistry and biochemistry to determine the structures of an immense variety of molecules, including inorganic compounds, DNA and proteins. X-ray diffraction is commonly carried out using single crystals of a material, but if these are not available, microcrystalline powdered samples may also be used, although this requires different equipment. A detailed discussion on X-ray diffraction may be found in Chapter 4 in "Principles of Protein X-ray Crystallography" by Drenth, second edition 1999, Springer-Verlag Inc.

"Bragg's Law" refers to the principle that defines the diffraction conditions that give rise to constructive interferences. When the phase shift of the incident radiation is proportional to $2\pi$, the condition can be expressed as: $n\lambda=2d\sin(\theta)$, where n is an integer; λ is the wavelength of the X-ray radiation, or radiations caused by moving electrons, protons and neutrons; d is the spacing between the planes in the atomic lattice, and θ is the angle between the incident ray and the scattering planes.

"Crystallization" in the context of protein X-ray crystallography refers to the processes during which soluble proteins are transformed into their crystalline forms. Crystals of a protein can be grown out of its solution state under experimental conditions that allow controlled phase transition. Such experimental conditions include a mixture of multiple solutions that often contain an aqueous solution of the target protein, a solution of one or a mixture of precipitants, and one or more compounds that contribute to the overall pH or ionic strength of the final mixture.

Provided herein are crystalline forms of a plant peptide deformylase polyepeptide, or a deformylase complexed with other molecules or chemical entities. Analysis of such crystalline forms of a polypeptide provides data in the form of structure coordinates. Exemplary structure coordinates for *Arabidopsis thaliana* peptide deformylase polypeptide are provided in Table 1. As used herein, the term "atomic coordinates" or "structure coordinates" refers to mathematical coordinates that describe the positions of atoms in crystals of a plant peptide deformylase in Protein Data Bank (PDB) format, including X, Y, Z and B, for each atom. The diffraction data obtained from the crystals are used to calculate an electron density map of the repeating unit of the crystal. The electron density maps may be used to establish the positions (i.e., coordinates X, Y and Z) of the individual atoms within the crystal. Those of skill in the art understand that a set of structure coordinates determined by X-ray crystallography is not without standard error. For the purpose of this invention, any set of structure coordinates for a plant peptide deformylse from any source having a root mean square deviation (r.m.s.d) of non-hydrogen atoms of less than about 1.5 Å when superimposed on the non-hydrogen atom positions of the corresponding atomic coordinates of Table 1 are considered substantially identical or homologous. Moreover, any set of structure coordinates for plant peptide deformylse from any source having a root mean square deviation of non-hydrogen atoms of less than about 0.75 Å when superimposed on the non-hydrogen atom positions of the corresponding atomic coordinates of Table 1 are considered substantially identical or homologous.

The term "root mean square deviation" means the square root of the arithmetic mean of the squares of the deviations. It is a way to express the deviation or variation from a trend or object. For purposes of this invention, the "root mean square deviation" defines the variation in the backbone of a protein from the backbone of a *Arabidopsis thaliana* peptide deformylase polypeptide or an active site portion thereof, as defined by the structure coordinates described herein. "Having substantially the same three-dimensional structure" refers to a polypeptide that is characterized by a set of atomic structure coordinates that have a root mean square deviation (r.m.s.d.) of less than or equal to about 1.5 Å when superimposed onto the atomic structure coordinates of Table 1 when at least about 50% to 100% of the C α atoms of the coordinates are included in the superposition.

Slight variations in structure coordinates can be generated by mathematically manipulating the plant peptide deformylase structure coordinates provided herein. For example, the structure coordinates set forth in Table 1 could be manipulated by crystallographic permutations of the structure coordinates, fractionalization of the structure coordinates, integer additions or subtractions to sets of the structure coordinates, inversion of the structure coordinates or any combination of the above. Alternatively, modifications in the crystal structure due to mutations, additions, substitutions, and/or deletions of amino acids, or other changes in any of the components that make up the crystal, could also yield variations in structure coordinates. Such slight variations in the individual coordinates will have little effect on overall shape. If such variations are within an acceptable standard error as compared to the original coordinates, the resulting three-dimensional shape is considered to be structurally equivalent. Thus, for the purpose of the structures provided herein, any active site, binding site or binding pocket defined by a set of structure coordinates for a polypeptide or for a homolog of a polypeptide from any source having a root mean square deviation of non-hydrogen atoms of less than about 1.5 Å when superimposed on the non-hydrogen atom positions of the corresponding atomic coordinates of Table 1, are considered substantially identical or homologous.

Figure 3:
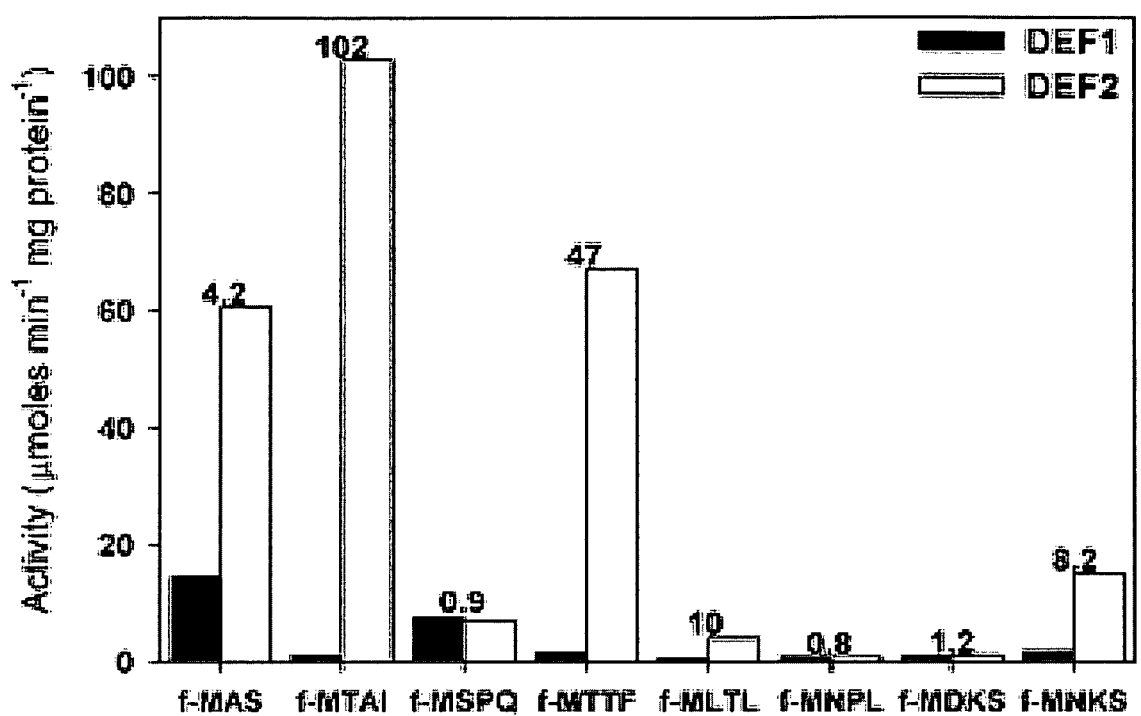
FIG. 3 depicts a graph of substrate specificity comparison of AtDEF1 and AtDEF2.

Active sites are of significant utility in the identification of compounds that specifically interact with, and modulate the activity of, a particular polypeptide. The association of natural ligands or substrates with the active sites of their corresponding receptors or enzymes is the basis of many biological mechanisms of action. Similarly, many compounds exert their biological effects through association with the active sites of receptors and enzymes. Such associations may occur with all or any parts of the active site. An understanding of such associations helps lead to the design of compounds that modulate the activity of their target. Therefore, this information is valuable in designing potential modifiers of plant peptide deformylase activity, as discussed in more detail below. For example, the structure of a substrate utilized by a particular deformylase can be used to design compounds that bind to an active site of a peptide deformylase. Referring to FIG. 3, substrate specificities for plant peptide deformylase AtDEF1 and AtDEF2 are shown. AtDEF1 and 2 activities are influenced by peptide substrate sequence. Peptide mimics of the N-termini of chloroplast-translated proteins, ribosomal protein S18 (f-MDKS), Rubisco LS (f-MSPQ), D1(f-MTAI), PSI-I (f-MTTF), PSII-I (f-MLTL), and ATPase subunit III (f-MNPL) were tested as substrates. In addition to a control substrate for the assay (f-MAS), the formate-dehydrogenase-linked assay was performed with 4 mM substrate and either 1.2 mg AtDEF1 or 0.2 mg AtDEF2. The numbers above the grouped bars represent the ratio of AtDEF2 to AtDEF1 activities. (Dirk et al., Arch Biochem Biophys 406:135-141).

The term "active site (or binding pocket)," as used herein, refers to a region of a molecule or molecular complex, that, as a result of its shape, favorably associates with another chemical entity or compound. Thus, an active site may include or consist of features such as interfaces between domains. Chemical entities or compounds that may associate with an active site include, but are not limited to, compounds, ligands, cofactors, substrates, inhibitors, agonists, antagonists, etc.

Figure 5:
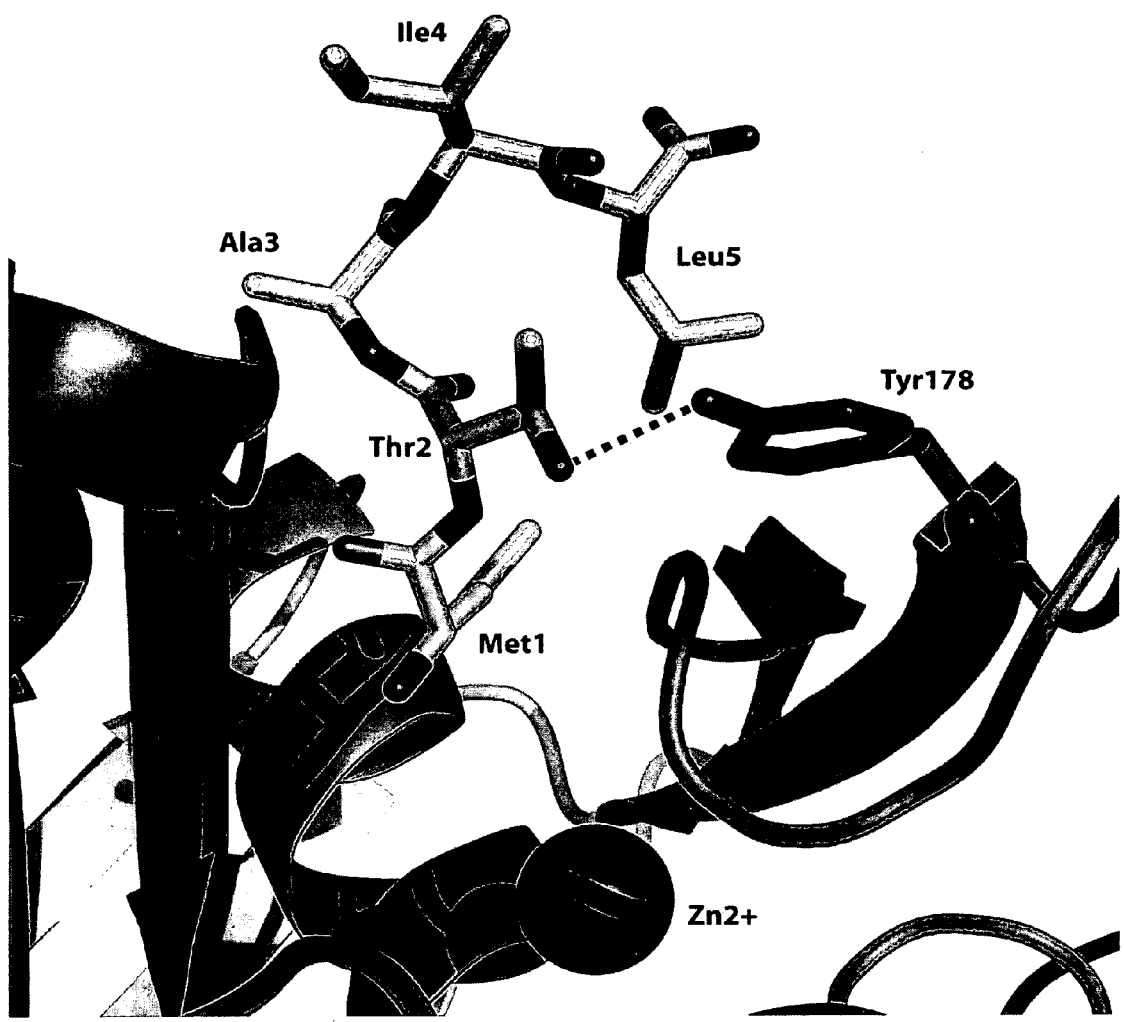
FIG. 5 depicts a molecular model of the N-terminal residues from the D1 polypeptide docked into the active site of *Arabidopsis thaliana* peptide deformylase.

An exemplary active site for a plant peptide deformylase is provided by amino acid residues Gly121, Gly123, Leu124, Gln128, Glu169, Gly170, Cys171, Leu172, His213, Glu214, His217, and Tyr178 of SEQ ID NO:1 and as shown in Table 1. Referring to FIG. 5, a model of the D1 N-terminus in AtDEF2's active site is provided. Potential H-bond highlighted between the Thr in the $P_2$ position of the polypeptide substrate and a conserved AtDEF2 Tyr178 just carboxy terminal to motif II. The model was generated by taking a snapshot from a molecular dynamics simulation using AMBER. The total length of the simulation was 1 ns, and this snapshot is at 126 ps.

In general, the exemplary active site is defined by a set of points having a root mean square deviation of less than about 0.35 Å from points representing the backbone atoms of amino acids as represented by structure coordinates listed in Table 1. As noted above, the crystalline form optionally includes additional molecules such as a coordinated metal ion selected from the group of metals consisting of Fe, Zn, Ni and combinations thereof. In some aspects, the metal ion is coordinated by the amino acids Cys171, His213, and His217.

Also provided are scalable three-dimensional configuration of points, at least a portion of said points derived from structure coordinates of at least a portion of an *Arabidopsis thaliana* peptide deformylase molecule or molecular complex listed in Table 1 and having a root mean square deviation of about 1.04 Å from said structure coordinates. Preferably, at least a portion of the points are derived from the *Arabidopsis thaliana* peptide deformylase structure coordinates derived from structure coordinates representing the locations of at least the backbone atoms of a plurality of the amino acids defining at least one *Arabidopsis thaliana* peptide deformylase or *Arabidopsis thaliana* peptide deformylase-like active site, the active site including amino acids Gly121, Gly123, Leu124, Gln128, Glu169, Gly170, Cys171, Leu172, His213, Glu214, His217, and Tyr178.

The structure coordinates generated for a plant peptide deformylase, or an active site thereof, as shown in Table 1 define a unique configuration of points in space. Those of skill in the art understand that a set of structure coordinates for a polypeptide, or a polypeptide complexed with a chemical entity, or a portion thereof, define a relative set of points that, in turn, define a configuration in three dimensions. A similar or identical configuration can be defined by an entirely different set of coordinates, provided the distances and angles between coordinates remain essentially the same. Accordingly, the coordinates provided in Table 1 provide a "scalable" configuration of points that can be modified by increasing or decreasing the distances between coordinates by a scalar factor while keeping the angles essentially the same.

The atomic structure coordinates provided herein can be used in molecular modeling and design, as described more fully below. The present invention encompasses the structure coordinates and other information, e.g., amino acid sequence, connectivity tables, vector-based representations, temperature factors, etc., used to generate the three-dimensional structure of the plant peptide deformylase polypeptide for use in the software programs described below and other software programs.

The invention encompasses machine-readable media embedded with the three-dimensional structure of the model described herein, or with portions thereof. As used herein, "machine-readable medium" refers to any medium that can be read and accessed directly by a computer or scanner. Such media include, but are not limited to: magnetic storage media, such as floppy discs, hard disc storage medium and magnetic tape; optical storage media such as optical discs or CD-ROM; electrical storage media such as RAM or ROM; and hybrids of these categories such as magnetic/optical storage media. Such media further include paper on which is recorded a representation of the atomic structure coordinates, e.g., Cartesian coordinates, that can be read by a scanning device and converted into a three-dimensional structure with an OCR.

A variety of data storage structures are available to a skilled artisan for creating a computer readable medium having recorded thereon the atomic structure coordinates of the invention or portions thereof and/or X-ray diffraction data. The choice of the data storage structure will generally be based on the means chosen to access the stored information. In addition, a variety of data processor programs and formats can be used to store the sequence and X-ray data information on a computer readable medium. Such formats include, but are not limited to, Protein Data Bank ("PDB") format (Research Collaboratory for Structural Bioinformatics; Cambridge Crystallographic Data Centre format; Structure-data ("SD") file format (MDL Information Systems, Inc.; Dalby et al., 1992, J. Chem. Inf. Comp. Sci. 32:244-255), and line-notation, e.g., as used in SMILES (Weininger, 1988, J. Chem. Inf. Comp. Sci. 28:31-36). Methods of converting between various formats read by different computer software will be readily apparent to those of skill in the art, e.g., BABEL (v. 1.06, Walters & Stahl, .COPYRGT.1992, 1993, 1994). All format representations of the polypeptide coordinates described herein, or portions thereof, are contemplated by the present invention. By providing computer readable medium having stored thereon the atomic coordinates of the invention, one of skill in the art can routinely access the atomic coordinates of the invention, or portions thereof, and related information for use in modeling and design programs, described in detail below.

While Cartesian coordinates are important and convenient representations of the three-dimensional structure of a polypeptide, those of skill in the art will readily recognize that other representations of the structure are also useful. Therefore, the three-dimensional structure of a polypeptide, as discussed herein, includes not only the Cartesian coordinate representation, but also all alternative representations of the three-dimensional distribution of atoms. For example, atomic coordinates may be represented as a Z-matrix, wherein a first atom of the protein is chosen, a second atom is placed at a defined distance from the first atom, a third atom is placed at a defined distance from the second atom so that it makes a defined angle with the first atom. Each subsequent atom is placed at a defined distance from a previously placed atom with a specified angle with respect to the third atom, and at a specified torsion angle with respect to a fourth atom. Atomic coordinates may also be represented as a Patterson function, wherein all interatomic vectors are drawn and are then placed with their tails at the origin. This representation is particularly useful for locating heavy atoms in a unit cell. In addition, atomic coordinates may be represented as a series of vectors having magnitude and direction and drawn from a chosen origin to each atom in the polypeptide structure. Furthermore, the positions of atoms in a three-dimensional structure may be represented as fractions of the unit cell (fractional coordinates), or in spherical polar coordinates.

Additional information, such as thermal parameters, which measure the motion of each atom in the structure, chain identifiers, which identify the particular chain of a multi-chain protein in which an atom is located, and connectivity information, which indicates to which atoms a particular atom is bonded, is also useful for representing a three-dimensional molecular structure.

Accordingly, also provided herein is a machine-readable data storage medium including a data storage material encoded with machine readable data which, when using a machine programmed with instructions for using the data, displays a graphical three-dimensional representation of at least one molecule or molecular complex selected from the group consisting of (i) a molecule or molecular complex including at least a portion of an *Arabidopsis thaliana* peptide deformylase or an *Arabidopsis thaliana* peptide deformylase-like active site including amino acids Gly121, Gly123, Leu124, Gln128, Glu169, Gly170, Cys171, Leu172, His213, Glu214, His217, and Tyr178 the active site being defined by a set of points having a root mean square deviation of less than about 1.5 Å from points representing the backbone atoms of the amino acids as represented by structure coordinates listed in Table 1.

Structure information, typically in the form of the atomic structure coordinates, can be used in a variety of computational or computer-based methods to, for example, design, screen for and/or identify compounds that bind the crystallized polypeptide or a portion or fragment thereof, or to intelligently design mutants that have altered biological properties, and the like. Three-dimensional modeling may be performed using the experimentally determined coordinates derived from X-ray diffraction patterns, such as those in Table 1, for example, wherein such modeling includes, but is not limited to, drawing pictures of the actual structures, building physical models of the actual structures, and determining the structures of related subunits and /ligand and subunit/ligand complexes using the coordinates. Such molecular modeling can utilize known X-ray diffraction molecular modeling algorithms or molecular modeling software to generate atomic coordinates corresponding to the three-dimensional structure of a plant peptide deformylase.

As described above, molecular modeling involves the use of computational methods, preferably computer assisted methods, to build realistic models of molecules that are identifiably related in sequence to the known crystal structure. It also involves modeling new small molecule inhibitors bound to a plant peptide deformylase starting with the structures of deformylase alone or complexed with known ligands or inhibitors. The methods utilized in ligand modeling range from molecular graphics (i.e., 3D representations) to computational chemistry (i.e., calculations of the physical and chemical properties) to make predictions about the binding of ligands or activities of ligands; to design new ligands; and to predict novel molecules, including ligands such as compounds that inhibit the activity of a plant deformylase. Such compounds may be useful as herbicides, for example.

One approach to rational design of a compound is to search for known molecular structures that might bind to an active site. Using molecular modeling, rational design programs can look at a range of different molecular structures of compounds that may fit into the active site of an enzyme or protein, and by moving them in a three-dimensional environment it can be decided which structures actually fit the site well. An alternate but related rational compound design approach starts with the known structure of a complex with a small molecule ligand and models modifications of that small molecule in an effort to make additional favorable interactions with peptide deformylase polypeptides, and/or the active site of such polypeptides.

The present invention includes the use of molecular and computer modeling techniques to design and select ligands, such as small molecule agonists or antagonists or other compounds that interact with peptide deformylase polypeptides. Such compounds include, but are not limited to, actinonin and derivatives thereof.

This invention also includes the design of compounds that act as uncompetitive inhibitors of at least one function of peptide deformylase polypeptides. These inhibitors may bind to all, or a portion of, the active sites or other regions of the polypeptide already bound to a ligand and may be more potent and less non-specific than competitive inhibitors that compete for active sites. Similarly, non-competitive inhibitors that bind to and inhibit at least one function of peptide deformylase polypeptides whether or not it is bound to another chemical entity, such as a natural ligand, for example, may be designed using the atomic coordinates of the chimeras or complexes comprising the chimeras of this invention.

The atomic coordinates of the present invention also provide the needed information to probe a crystal of a peptide deformylase polypeptide with molecules composed of a variety of different chemical features to determine optimal sites for interaction between candidate inhibitors and/or activators. For example, high resolution X-ray diffraction data collected from crystals saturated with solvent allows the determination of where each type of solvent molecule sticks. Small molecules that bind to those sites can then be designed and synthesized and tested for their inhibitory activity (Travis, J., Science 262:1374 (1993)).

The present invention also includes methods for computationally screening small molecule databases and libraries for chemical entities, agents, ligands, or compounds that can bind in whole, or in part, to peptide deformylase polypeptides. In this screening, the quality of fit of such entities or compounds to the binding site or sites may be judged either by shape complementarity or by estimated interaction energy (Meng, E. C. et al., J. Comp. Chem. 13:505-524 (1992)).

The design of compounds that bind to, promote or inhibit the functional activity of peptide deformylase polypeptides according to this invention generally involves consideration of two factors. First, the compound must be capable of physically and structurally associating with the peptide deformylase polypeptide. Non-covalent molecular interactions important in the association of the peptide deformylase polypeptide with the compound include hydrogen bonding, van der Waals and hydrophobic interactions. Second, the compound must be able to assume a conformation that allows it to associate with a peptide deformylase polypeptide. Although certain portions of the compound may not directly participate in the association with peptide deformylase polypeptide, those portions may still influence the overall conformation of the molecule. This, in turn, may have a significant impact on binding affinities and potency. Such conformational requirements include the overall three-dimensional structure and orientation of the chemical entity or compound in relation to all or a portion of the active site or other region of a peptide deformylase polypeptide, or the spacing between functional groups of a compound comprising several chemical entities that directly interact with a peptide deformylase polypeptide.

The potential, predicted, inhibitory agonist, antagonist or binding effect of a ligand or other compound on a peptide deformylase polypeptide may be analyzed prior to its actual synthesis and testing by the use of computer modeling techniques. If the theoretical structure of the given compound suggests insufficient interaction and association between it and the peptide deformylase polypeptide, synthesis and testing of the compound may be obviated. However, if computer modeling indicates a strong interaction, the molecule may then be synthesized and tested for its ability to interact with a peptide deformylase polypeptide. In this manner, synthesis of inoperative compounds may be avoided. In some cases, inactive compounds are synthesized predicted on modeling and then tested to develop a SAR (structure-activity relationship) for compounds interacting with a specific region of a peptide deformylase polypeptide.

One skilled in the art may use one of several methods to screen chemical entities fragments, compounds, or agents for their ability to associate with a peptide deformylase polypeptide and more particularly with the individual binding pockets or active sites of the peptide deformylase polypeptide. This process may begin by visual inspection of, for example, the active site based on the atomic coordinates of the polypeptide or the polypeptide complexed with a ligand. Selected chemical entities, compounds, or agents may then be positioned in a variety of orientations, or docked within an individual binding pocket of the peptide deformylase polypeptide. Docking may be accomplished using software-such as Quanta and Sybyl, followed by energy minimization and molecular dynamics with standard molecular mechanics forcefields, such as CHARMM and AMBER.

Specialized computer programs may also assist in the process of selecting chemical entities. These include but are not limited to: GRID (Goodford, P. J., "A Computational Procedure for Determining Energetically Favorable Binding Sites on Biologically Important Macromolecules," J. Med. Chem.

28:849-857 (1985), available from Oxford University, Oxford, UK); MCSS (Miranker, A. and M. Karplus, "Functionality Maps of Binding Sites: A Multiple Copy Simultaneous Search Method." Proteins: Structure, Function and Genetics 11: 29-34 (1991), available from Molecular Simulations, Burlington, Mass.); AUTODOCK (Goodsell, D. S. and A. J. Olsen, "Automated Docking of Substrates to Proteins by Simulated Annealing" Proteins: Structure. Function, and Genetics 8:195-202 (1990), available from Scripps Research Institute, La Jolla, Calif.); DOCK (Kuntz, I. D. et al., "A Geometric Approach to Macromolecule-Ligand Interactions," J. Mol. Biol. 161:269-288 (1982), available from University of California, San Francisco, Calif.); Gold (Jones, G. et al., "Development and validation of a genetic algorithm for flexible docking." J. Mol. Biol. 267: 727-748 (1997)); Glide (Halgren, T. A. et al., "Glide: a new approach for rapid, accurate docking and scoring. 2. Enrichment factors in database screening." J Med Chem, 47:1750-1759 (2004), Friesner, R. A. et al., "Glide: a new approach for rapid, accurate docking and scoring. 1. Method and assessment of docking accuracy." J Med Chem, 47:1739-1749 (2004)); FlexX (Rarey, M. et al., "A fast flexible docking method using an incremental construction algorithm." J. Mol. Biol. 261: 470-489 (1996)); and ICM (Abagyan, R. A. and Totrov, M. M., J. Mol. Biol. 235: 983-1002 (1994)).

The use of software such as GRID, a program that determines probable interaction sites between probes with various functional group characteristics and the macromolecular surface, is used to analyze the surface sites to determine structures of similar inhibiting proteins or compounds. The GRID calculations, with suitable inhibiting groups on molecules (e.g., protonated primary amines) as the probe, are used to identify potential hotspots around accessible positions at suitable energy contour levels. The program DOCK may be used to analyze an active site or ligand binding site and suggest ligands with complementary steric properties. See also, See, also, Kellenberger, P. N et al., "Recovering the true targets of specific ligands by virtual screening of the protein data bank," Proteins 54(4):671-80 (2004); Oldfield, T., "Applications for macromolecular map interpretation: X-AUTOFIT, X-POWERFIT, X-BUILD, X-LIGAND, and X-SOLVATE," Methods Enzymol. 374:271-300 (2003); Richardson, J. S. et al., "New tools and data for improving structures, using all-atom contacts," Methods Enzymol. 374: 385-412 (2003); Terwilliger, T. C., "Improving macromolecular atomic models at moderate resolution by automated iterative model building, statistical density modification and refinement," Acta Crystallogr D Biol Crystallogr. 59(Pt 7): 1174-82 (2003); Toerger, T. C. and Sacchettini, J. C., "TEXTAL system: artificial intelligence techniques for automated protein model building," Methods Enzymol. 374:244-70 (2003); von Grotthuss, M. et al., "Predicting protein structures accurately," Science 304 (5677):1597-9 (2004); Rajakiannan, V. et al., "The use of ACORN in solving a 39.5 kDa macromolecule with 1.9 Å resolution laboratory source data," J Synchrotron Radiat. 11(Pt 4):358-62 (2004); Claude, J. B. et al., "CaspR: a web server for automated molecular replacement using homology modeling," Nucleic Acids Res. 32(Web Server issue): W606-9 (2004); Suhre, K. and Sanejouand, Y. H., "ElNemo: a normal mode web server for protein movement analysis and the generation of templates for molecular replacement," Nucleic Acids Res. 32(Web Server issue):W610-4 (2004).

Once suitable chemical entities, compounds, or agents have been selected, they can be assembled into a single ligand or compound or inhibitor or activator. Assembly may proceed by visual inspection of the relationship of the fragments to each other on the three-dimensional image. This may be followed by manual model building using software such as Quanta or Sybyl.

Useful programs to aid in connecting the individual chemical entities, compounds, or agents include but are not limited to: CAVEAT (Bartlett, P. A. et al., "CAVEAT: A Program to Facilitate the Structure-Derived Design of Biologically Active Molecules." In Molecular Recognition in Chemical and Biological, Problems, Special Pub., Royal Chem. Soc., 78, pp. 82-196 (1989)); 3D Database systems such as MACCS-3D (MDL Information Systems, San Leandro, C A and Martin, Y. C., "3D Database Searching in Drug Design," J. Med. Chem. 35: 2145-2154 (1992); and HOOK (available from Molecular Simulations, Burlington, Mass.).

Several methodologies for searching three-dimensional databases to test hypotheses and select compounds for screening are available. These include the program CAVEAT (Bacon et al., J. Mol. Biol. 225:849-858 (1992)). For instance, CAVEAT uses databases of cyclic compounds which can act as "spacers" to connect any number of chemical fragments already positioned in the active site. This allows one skilled in the art to quickly generate hundreds of possible ways to connect the fragments already known or suspected to be necessary for tight binding.

Instead of proceeding to build an inhibitor activator, agonist or antagonist of a peptide deformylase polypeptide in a step-wise fashion one chemical entity at a time as described above, such compounds may be designed as a whole or "de novo" using either an empty active site or optionally including some portion(s) of a known molecules. These methods include: LUDI (Bohm, H.-J., "The Computer Program LUDI: A New Method for the De Novo Design of Enzyme Inhibitors", J. Comp. Aid. Molec. Design, 6, pp. 61-78 (1992), available from Biosym Technologies, San Diego, Calif.); LEGEND (Nishibata, Y. and A. Itai, Tetrahedron 47:8985 (1991), available from Molecular Simulations, Burlington, Mass.); and LeapFrog (available from Tripos Associates, St. Louis, Mo.).

For instance, the program LUDI can determine a list of interaction sites into which to place both hydrogen bonding and hydrophobic fragments. LUDI then uses a library of linkers to connect up to four different interaction sites into fragments. Then smaller "bridging" groups such as —CH2— and —COO— are used to connect these fragments.

Once a compound has been designed or selected by the above methods, the affinity with which that compound may bind or associate with a peptide deformylase polypeptide may be tested and optimized by computational evaluation and/or by testing biological activity after synthesizing the compound. Inhibitors or compounds may interact with the deformylase in more than one conformation that is similar in overall binding energy. In those cases, the deformation energy of binding is taken to be the difference between the energy of the free compound and the average energy of the conformations observed when the compound binds to a peptide deformylase polypeptide.

A compound designed or selected as binding or associating with a plant peptide deformylase may be further computationally optimized so that in its bound state it would preferably lack repulsive electrostatic interaction with the protein. Such non-complementary (e.g., electrostatic) interactions include repulsive charge-charge, dipole-dipole and charge-dipole interactions. Specifically, the sum of all electrostatic interactions between the inhibitor and the chimera when the inhibitor is bound, preferably make a neutral or favorable contribution to the enthalpy of binding. Weak binding compounds will also be designed by these methods so as to determine SAR.

Specific computer software is available in the art to evaluate compound deformation energy and electrostatic interaction. Examples of programs designed for such uses include: Gaussian 92, revision C (M. J. Frisch, Gaussian, Inc., Pittsburgh, Pa., COPYRGT 1992); AMBER, version 4.0 (P. A. Kollman, University of California at San Francisco, COPYRGT 1994); QUANTA/CHARMM (Molecular Simulations, Inc., Burlington, Mass. COPYRGT 1994); Insight II/Discover (Biosysm Technologies Inc., San Diego, Calif. COPYRGT. 1994); and Delphi (A. Nicholls and B. Honig "A rapid finite difference algorithm, utilizing successive over-relaxation to solve the Poisson-Boltzman equation" J. Comp. Chem. 12: 435-445 (1991), M. K. Gilson and B. Honig. "Calculation of the total electrostatic energy of a macromolecular system: Solvation energies, binding energies and conformation analysis" Proteins 4: 7-18 (1988), M. K. Gilson et al., "Calculating the electrostatic potential of molecules in solution: Method and error assessment" J Comp. Chem 9: 327-335 (1987)). Other hardware systems and software packages will be known to those skilled in the art.

Once a compound that associates with the peptide deformylase polypeptide has been optimally selected or designed, as described above, substitutions may then be made in some of its atoms or side groups in order to improve or modify its binding properties. Generally, initial substitutions are conservative, i.e., the replacement group will have approximately the same size, shape, hydrophobicity and charge as the original group. It should, of course, be understood that components known in the art to alter conformation may be avoided. Such substituted chemical compounds may then be analyzed for efficiency of fit to a peptide deformylase polypeptide by the same computer methods described in detail, above.

Accordingly, as described above the present invention provides a computer-assisted method for obtaining structural information about a molecule or a molecular complex of unknown structure including: crystallizing the molecule or molecular complex; generating an x-ray diffraction pattern from the crystallized molecule or molecular complex; applying at least a portion of the structure coordinates set forth in Table 1 to the x-ray diffraction pattern to generate a three-dimensional electron density map of at least a portion of the molecule or molecular complex whose structure is unknown.

In another aspect, the present invention provides a computer-assisted method for homology modeling an *Arabidopsis thaliana* peptide deformylase homolog including: aligning the amino acid sequence of an *Arabidopsis thaliana* peptide deformylase homolog with the amino acid sequence of *Arabidopsis thaliana* peptide deformylase SEQ ID NO:1 and incorporating the sequence of the *Arabidopsis thaliana* peptide deformylase homolog into a model of *Arabidopsis thaliana* peptide deformylase derived from structure coordinates set forth in Table 1 to yield a preliminary model of the *Arabidopsis thaliana* peptide deformylase homolog; subjecting the preliminary model to energy minimization to yield an energy minimized model; remodeling regions of the energy minimized model where stereochemistry restraints are violated to yield a final model of the *Arabidopsis thaliana* peptide deformylase homolog.

Figure 4:
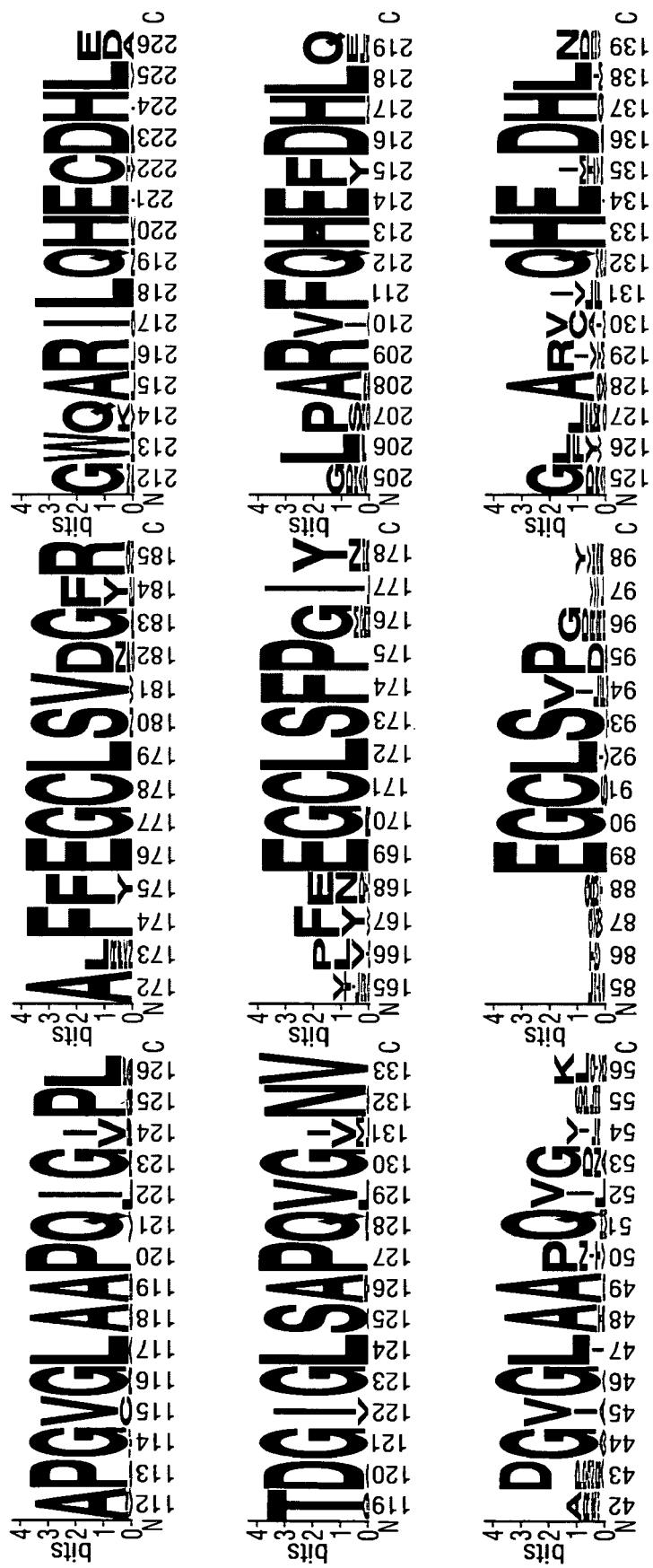
FIG. 4 depicts a comparison of amino acid sequence conservation of the three motifs in AtDEF1 and 2 and bacterial DEFs (SEQ ID NOS 2-5).

Domains of peptide deformylase polypeptides retain sequence and structural conservation. Accordingly, these conserved regions can be used to model deformylase homologs. Referring to FIG. 4, conservation of the three motifs in AtDEF1 and 2 and bacterial DEFs are shown. AtDEF1- and 2-like sequences were identified with a tblastn (BLAST) search of plant EST databases, aligned around the indicated motifs, and submitted for analysis by WebLogo. For the bacterial DEF alignment, the first 100 bacterial sequences from a blastp using the SwissProt database with Q2VP16 (*E. coli*) as query were used for the similarity analyses. Sequence conservation is represented by WebLogo images by the overall height of the stack and relative frequency of the amino acid at the position within the sequence is represented by the height of its symbol (Crooks et al., Genome Res. 14:1188-1190; Schneider and Stephens, Nucl. Acids Res. 18:6097-6100).

Due to the nature of the sequences used for the plant DEFs, different numbers of sequences were used for each motif in the generation of FIG. 4. For motif I, there were 34, 42 and 100 sequences for 1, 2 and bacterial DEFs, respectively; whereas, there were 36, 40, and 100 for motif II and 40, 32, and 100 for motif II.

In addition, referring to FIGS. 6, 7 and 8, a phylogenetic analyses of the distribution of amino acid substitutions throughout the available collection of peptide deformylase sequences from plants compared with bacterial deformylase is provided. The results are presented as a comparison of both the number and percentage of substitutions found at any location within the sequence of peptide deformylase 1 & 2 from plants as well as *E. coli*. There are a number of residue changes which suggest selection pressure in the evolution of peptide deformylase specifically adapted to plants. Thus, these changes are indicative of specific sites where residue changes are likely to affect peptide deformylase activity and/or specificity without adversely affecting enzyme stability and are useful as targets for mutational changes.

Thus, the structure coordinates set forth in Table 1 can be used to aid in obtaining structural information about another crystallized molecule or molecular complex. A "molecular complex" means a protein in covalent or non-covalent association with a chemical entity or compound. The method of the invention allows determination of at least a portion of the three-dimensional structure of molecules or molecular complexes which contain one or more structural features that are similar to structural features of *Arabidopsis thaliana* peptide deformylase. These molecules are referred to herein as "structurally homologous" to *Arabidopsis thaliana* peptide deformylase. Similar structural features can include, for example, regions of amino acid identity, conserved active site or binding site motifs, and similarly arranged secondary structural elements (e.g., α helices and β sheets). Optionally, structural homology is determined by aligning the residues of the two amino acid sequences to optimize the number of identical amino acids along the lengths of their sequences; gaps in either or both sequences are permitted in making the alignment in order to optimize the number of identical amino acids, although the amino acids in each sequence must nonetheless remain in their proper order. Preferably, two amino acid sequences are compared using the Blastp program, version 2.0.9, of the BLAST 2 search algorithm, as described by Tatusova et al., FEMS Microbiol Lett., 174:247-50 (1999). Preferably, the default values for all BLAST 2 search parameters are used, including matrix=BLOSUM62; open gap penalty=11, extension gap penalty=1, gap x_dropoff=50, expect=10, wordsize=3, and filter on. In the comparison of two amino acid sequences using the BLAST search algorithm, structural similarity is referred to as "identity." Preferably, a structurally homologous molecule is a protein that has an amino acid sequence sharing at least 65% identity with the amino acid sequence of *Arabidopsis thaliana* peptide deformylase. Methods for generating structural information about the structurally homologous molecule or molecular complex are well-known and include, for example, molecular replacement techniques. By using molecular replacement, all or part of the structure coordinates of *Arabidopsis thaliana* peptide deformylase (and set forth in Table 1) can be used to determine the structure of a crystallized molecule or molecular complex whose structure is unknown more quickly and efficiently than attempting to determine such information ab initio.

Molecular replacement provides an accurate estimation of the phases for an unknown structure. Phases are a factor in equations used to solve crystal structures that cannot be determined directly obtaining accurate values for the phases, by methods other than molecular replacement, is a time-consuming process that involves iterative cycles of approximations and refinements and greatly hinders the solution of crystal structures. However, when the crystal structure of a protein containing at least a structurally homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of *Arabidopsis thaliana* peptide deformylase according to Table 1 within the unit cell of the crystal of the unknown molecule or molecular complex so as best to account for the observed x-ray diffraction pattern of the crystal of the molecule or molecular complex whose structure is unknown. Phases can then be calculated from this model and combined with the observed x-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (E. Lattman, "Use of the Rotation and Translation Functions," in Meth. Enzymol., 115:55-77 (1985); M. G. Rossman, ed., "The Molecular Replacement Method," Int. Sci. Rev. Ser., No. 13, Gordon & Breach, New York (1972)).

Structural information about a portion of any crystallized molecule or molecular complex that is sufficiently structurally homologous to a portion of *Arabidopsis thaliana* peptide deformylase can be resolved by this method. In addition to a molecule that shares one or more structural features with *Arabidopsis thaliana* peptide deformylase as described above, a molecule that has similar bioactivity, such as the same catalytic activity, substrate specificity or ligand binding activity as *Arabidopsis thaliana* peptide deformylase, may also be sufficiently structurally homologous to *Arabidopsis thaliana* peptide deformylase to permit use of the structure coordinates of *Arabidopsis thaliana* peptide deformylase to solve its crystal structure.

In addition, using homology modeling, a computer model of an *Arabidopsis thaliana* peptide deformylase homolog can be built or refined without crystallizing the homolog. First, a preliminary model of the *Arabidopsis thaliana* peptide deformylase homolog is created by sequence alignment with *Arabidopsis thaliana* peptide deformylase, secondary structure prediction, the screening of structural libraries, or any combination of those techniques. Computational software may be used to carry out the sequence alignments and the secondary structure predictions. Structural incoherences, e.g., structural fragments around insertions and deletions, can be modeled by screening a structural library for peptides of the desired length and with a suitable conformation. For prediction of the side chain conformation, a side chain rotamer library may be employed. Where the *Arabidopsis thaliana* peptide deformylase homolog has been crystallized, the final homology model can be used to solve the crystal structure of the homolog by molecular replacement, as described above. Next, the preliminary model is subjected to energy minimization to yield an energy minimized model. The energy minimized model may contain regions where stereochemistry restraints are violated, in which case such regions are remodeled to obtain a final homology model. The homology model is positioned according to the results of molecular replacement, and subjected to further refinement including molecular dynamics calculations.

In another aspect, the present invention provides a computer-assisted method for designing a potential modifier of *Arabidopsis thaliana* peptide deformylase activity including: supplying a computer modeling application with a set of structure coordinates of a molecule or molecular complex, the molecule or molecular complex including at least a portion of at least one *Arabidopsis thaliana* peptide deformylase or *Arabidopsis thaliana* peptide deformylase-like active site, the active site including amino acids Gly121, Gly123, Leu124, Gln128, Glu169, Gly170, Cys171, Leu172, His213, Glu214, His217, and Tyr178; supplying the computer modeling application with a set of structure coordinates for a chemical entity; evaluating the potential binding interactions between the chemical entity and active site of the molecule or molecular complex; structurally modifying the chemical entity to yield a set of structure coordinates for a modified chemical entity; and determining whether the modified chemical entity is expected to bind to the molecule or molecular complex, wherein binding to the molecule or molecular complex is indicative of potential modification of *Arabidopsis thaliana* peptide deformylase activity.

The present invention also provides a computer-assisted method for designing a potential modifier of *Arabidopsis thaliana* peptide deformylase activity de novo including: supplying a computer modeling application with a set of structure coordinates of a molecule or molecular complex, the molecule or molecular complex including at least a portion of at least one *Arabidopsis thaliana* peptide deformylase or *Arabidopsis thaliana* peptide deformylase like active site, wherein the active site includes amino acids Gly121, Gly123, Leu124, Gln128, Glu169, Gly170, Cys171, Leu172, His213, Glu214, His217, and Tyr178; forming a chemical entity represented by set of structure coordinates; and determining whether the chemical entity is expected to bind to the molecule or molecular complex, wherein binding to the molecule or molecular complex is indicative of potential modification of *Arabidopsis thaliana* peptide deformylase activity.

In another aspect, the present invention provides a method for making a potential modifier of *Arabidopsis thaliana* peptide deformylase activity, the method including chemically or enzymatically synthesizing a chemical entity to yield a potential modifier of *Arabidopsis thaliana* peptide deformylase activity, the chemical entity having been identified during a computer-assisted process including supplying a computer modeling application with a set of structure coordinates of a molecule or molecular complex, the molecule or molecular complex including at least a portion of a *Arabidopsis thaliana* peptide deformylase or *Arabidopsis thaliana* peptide deformylase-like active site; supplying the computer modeling application with a set of structure coordinates of a chemical entity; and determining whether the chemical entity is expected to bind to the molecule or molecular complex at the active site, wherein binding to the molecule or molecular complex is indicative of potential modification of *Arabidopsis thaliana* peptide deformylase activity.

In another aspect, the present invention provides a method for making a potential modifier of *Arabidopsis thaliana* peptide deformylase activity, the method including chemically or enzymatically synthesizing a chemical entity to yield a potential modifier of *Arabidopsis thaliana* peptide deformylase activity, the chemical entity having been designed during a computer-assisted process including supplying a computer modeling application with a set of structure coordinates of a molecule or molecular complex, the molecule or molecular complex including at least a portion of a *Arabidopsis thaliana* peptide deformylase or *Arabidopsis thaliana* peptide deformylase-like active site; supplying the computer modeling application with a set of structure coordinates for a chemical entity; evaluating the potential binding interactions between the chemical entity and the active site of the molecule or molecular complex; structurally modifying the chemical entity to yield a set of structure coordinates for a modified chemical entity; and determining whether the chemical entity is expected to bind to the molecule or molecular complex at the active site, wherein binding to the molecule or molecular complex is indicative of potential modification of *Arabidopsis thaliana* peptide deformylase activity.

In general, methods for making a potential modifier of a plant peptide deformylase activity are provided herein. Such methods include chemically or enzymatically synthesizing a chemical entity to yield a potential modifier of plant peptide deformylase activity. Those skilled in the art of crystallography will understand that the atomic coordinates provided herein can be used to design a chemical entity during a computer-assisted process that includes supplying a computer modeling application with a set of structure coordinates of a molecule or molecular complex, the molecule or molecular complex including at least a portion of a plant peptide deformylase or *Arabidopsis thaliana* peptide deformylase-like active site; forming a chemical entity represented by set of structure coordinates; and determining whether the chemical entity is expected to bind to the molecule or molecular complex at the active site. Binding to the molecule or molecular complex is indicative of potential modification of *Arabidopsis thaliana* peptide deformylase activity.

FIGS. 6-8 contain phylogenetic analyses of the distribution of amino acid substitutions throughout the available collection of peptide deformylase sequences from plants compared with bacteria. The results are presented as a comparison of both the number and percentage of substitutions found at any location within the sequence of peptide deformylase 1 & 2 from plants as well as *E. coli*. There are a number of residue changes which suggest selection pressure in the evolution of peptide deformylase specifically adapted to plants. Thus, these changes are indicative of specific sites where residue changes are likely to affect peptide deformylase activity and/or specificity without adversely affecting enzyme stability and are useful as targets for mutational changes.

AtDEF2 is an essential plant enzyme responsible for the co-translational processing of chloroplast translated proteins. Although biochemically characterized, no structure exists for AtDEF2 in part because of a requirement for 0.5 M NaCl for solubility. The dependency on sodium chloride for solubility was removed by limited tryptic proteolysis and crystals of AtDEF2 were obtained. The structure was determined by molecular replacement and refined to a resolution of 2.7 Å. The overall fold of the enzyme closely resembles the alpha+beta conformation of known bacterial peptide deformylases, with an r.m.s deviation of 1.04 Å on main chain atoms relative to the *E. coli* enzyme. The largest differences occur in the orientation of the C-terminal helix (helix 3) and the conformation of the loop between beta strands 2 and 3, which form part of the five-stranded central sheet. Modeling the preferred substrate for AtDEF2 (the N-termini of the D1 polypeptide from photosystem II), in both chloroplast protein structures can be used to elucidate the mechanism underlying the 102-fold greater activity of AtDEF2 on this sequence (see FIG. 3). Structural comparison can also be accomplished with the known eubacterial peptide deformylase structures to determine approaches for designing specific inhibitors against the chloroplast enzyme. Specific AtDEF2 inhibitors could potentially be used as broad-spectrum herbicides without impact on soil microorganisms.

The *Arabidopsis thaliana* DEF2 protein was over-expressed and purified from *E. coli*. Limited tryptic proteolysis yielded a form of *Arabidopsis thaliana* DEF2 (see FIG. 1B, SEQ ID NO:1) which readily crystallized. The useful crystals all belong to the tetragonal space group. The unit cell parameters were a, b, and c; wherein a is about 40 Å to about 60 Å, b is about 40 Å to about 60 Å, and c is about 120 Å to about 160 Å.

Crystals of the truncated peptide deformylase construct are grown by hanging drop vapor diffusion in 24 well plates with well solutions containing 15-18% peg monomethyl ester 550, 28-70 mM $ZnSO_4$, and 70 mM MES pH 6.5. Protein solution at approximately 5 mg/ml is mixed 1:1 with well solution to a final volume of 2-5 microliters for the crystallization drops. Crystals form in several days to several weeks. To prepare the crystals for data collection, they were briefly placed into a solution containing the same components as the well solution in addition to 20% glycerol, mounted in nylon or mylar loops, and flash-cooled by plunging into liquid nitrogen.

Table 1 lists the atomic structure coordinates for the *Arabidopsis thaliana* peptide deformylase (*A. thaliana* DEF2) molecule as derived by x-ray diffraction from a crystal of the protein. The following abbreviations are used in Table 1. "Atom type" refers to the element whose coordinates are measured. The first letter in the column defines the element. "X, Y, Z" crystallographically define the atomic position of the element measured. "B" is a thermal factor that measures movement of the atom around its atomic center. "Occ" is an occupancy factor that refers to the fraction of the molecules in which each atom occupies the position specified by the coordinates. A value of "1" indicates that each atom has the same conformation, i.e., the same position, in all molecules of the crystal.

Table 1 is provided below:

REMARK coordinates from simulated annealing refinement
REMARK refinement resolution: 500.0–2.4 A
REMARK starting r = 0.2407 free__r = 0.2946
REMARK final r = 0.2352 free__r = 0.2983
REMARK rmsd bonds = 0.007053 rmsd angles = 1.33915
REMARK wa__initial = 2.77981 wa__dynamics = 3.30373 wa__final = 2.90342
REMARK target = mlf md-method = torsion annealing schedule = slowcool
REMARK starting temperature = 2500 total md steps = 100 * 6

-continued

```
REMARK   sg = P4(1)2(1)2 a = 50.902 b = 50.902 c = 144.783 alpha = 90 beta = 90 gamma = 90
REMARK   parameter file 1  :  CNS_TOPPAR:protein_rep_cis.param
REMARK   parameter file 2  :  CNS_TOPPAR:ion.param
REMARK   parameter file 3  :  CNS_TOPPAR:water_rep.param
REMARK   molecular structure file: generate_r8h.mtf
REMARK   input coordinates: generate_r8h.pdb
REMARK   reflection file = pepdef1_p41212_cv.cns
REMARK   ncs = none
REMARK   B-correction resolution: 6.0–2.4
REMARK   initial B-factor correction applied to fobs:
REMARK   B11 =      1.447 B22 =      1.447 B33 =     −2.893
REMARK   B12 =      0.000 B13 =      0.000 B23 =      0.000
REMARK   B-factor correction applied to coordinate array B:     1.092
REMARK   bulk solvent: density level = 0.398841 e/A^3, B-factor = 39.902 A^2
REMARK   reflections with |Fobs|/sigma_F < 0.0 rejected
REMARK   reflections with |Fobs| > 10000 * rms(Fobs) rejected
REMARK   theoretical total number of refl. in resol. range:      8021 (   100.0%)
REMARK   number of unobserved reflections (no entry or |F| = 0):     5 (     0.1%)
REMARK   number of reflections rejected:                             0 (     0.0%)
REMARK   total number of reflections used:                        8016 (    99.9%)
REMARK   number of reflections in working set:                    7166 (    89.3%)
REMARK   number of reflections in test set:                        850 (    10.6%)
CRYST1   50.902   50.902  144.783  90.00  90.00  90.00   P 41 21 2
REMARK   FILENAME = "anneal_pepdef1_r8h_1.pdb"
REMARK   DATE: 28-Apr-05 13:49:32
REMARK   VERSION: 1.0
ATOM      1  CB   ASP  A   74      39.005   −3.139  −26.015  1.00  40.08  A
ATOM      2  CG   ASP  A   74      37.793   −3.950  −25.591  1.00  39.52  A
ATOM      3  OD1  ASP  A   74      37.991   −5.048  −25.026  1.00  39.78  A
ATOM      4  OD2  ASP  A   74      36.651   −3.487  −25.804  1.00  37.24  A
ATOM      5  C    ASP  A   74      39.677   −4.292  −28.136  1.00  39.44  A
ATOM      6  O    ASP  A   74      38.789   −5.104  −28.382  1.00  40.59  A
ATOM      7  N    ASP  A   74      41.403   −3.315  −26.608  1.00  40.71  A
ATOM      8  CA   ASP  A   74      40.079   −3.996  −26.689  1.00  40.00  A
ATOM      9  N    VAL  A   75      40.329   −3.631  −29.089  1.00  36.98  A
ATOM     10  CA   VAL  A   75      40.043   −3.850  −30.503  1.00  34.57  A
ATOM     11  CB   VAL  A   75      38.952   −2.881  −31.027  1.00  35.15  A
ATOM     12  CG1  VAL  A   75      37.610   −3.228  −30.407  1.00  35.82  A
ATOM     13  CG2  VAL  A   75      39.323   −1.440  −30.706  1.00  35.83  A
ATOM     14  C    VAL  A   75      41.294   −3.686  −31.367  1.00  33.70  A
ATOM     15  O    VAL  A   75      41.849   −2.591  −31.473  1.00  31.73  A
ATOM     16  N    GLN  A   76      41.744   −4.785  −31.968  1.00  32.36  A
ATOM     17  CA   GLN  A   76      42.917   −4.752  −32.834  1.00  31.43  A
ATOM     18  CB   GLN  A   76      43.809   −5.977  −32.597  1.00  30.15  A
ATOM     19  CG   GLN  A   76      43.948   −6.377  −31.146  1.00  32.55  A
ATOM     20  CD   GLN  A   76      45.062   −7.391  −30.900  1.00  33.57  A
ATOM     21  OE1  GLN  A   76      45.222   −8.363  −31.647  1.00  30.76  A
ATOM     22  NE2  GLN  A   76      45.832   −7.169  −29.835  1.00  32.62  A
ATOM     23  C    GLN  A   76      42.442   −4.747  −34.284  1.00  30.41  A
ATOM     24  O    GLN  A   76      41.713   −5.642  −34.714  1.00  32.15  A
ATOM     25  N    PHE  A   77      42.843   −3.737  −35.042  1.00  29.07  A
ATOM     26  CA   PHE  A   77      42.442   −3.672  −36.437  1.00  29.03  A
ATOM     27  CB   PHE  A   77      41.147   −2.871  −36.582  1.00  26.50  A
ATOM     28  CG   PHE  A   77      41.287   −1.426  −36.198  1.00  25.67  A
ATOM     29  CD1  PHE  A   77      41.416   −0.442  −37.172  1.00  25.19  A
ATOM     30  CD2  PHE  A   77      41.317   −1.050  −34.858  1.00  24.82  A
ATOM     31  CE1  PHE  A   77      41.572    0.895  −36.818  1.00  23.61  A
ATOM     32  CE2  PHE  A   77      41.473    0.283  −34.497  1.00  24.11  A
ATOM     33  CZ   PHE  A   77      41.600    1.258  −35.483  1.00  23.48  A
ATOM     34  C    PHE  A   77      43.523   −3.035  −37.287  1.00  30.55  A
ATOM     35  O    PHE  A   77      44.372   −2.293  −36.789  1.00  28.47  A
ATOM     36  N    GLU  A   78      43.487   −3.355  −38.576  1.00  33.02  A
ATOM     37  CA   GLU  A   78      44.418   −2.797  −39.542  1.00  34.82  A
ATOM     38  CB   GLU  A   78      44.965   −3.876  −40.491  1.00  35.56  A
ATOM     39  CG   GLU  A   78      45.913   −4.906  −39.860  1.00  35.90  A
ATOM     40  CD   GLU  A   78      45.187   −5.934  −39.001  1.00  37.85  A
ATOM     41  OE1  GLU  A   78      44.210   −6.534  −39.493  1.00  39.60  A
ATOM     42  OE2  GLU  A   78      45.590   −6.152  −37.841  1.00  37.63  A
ATOM     43  C    GLU  A   78      43.580   −1.814  −40.339  1.00  35.67  A
ATOM     44  O    GLU  A   78      42.386   −2.030  −40.543  1.00  34.84  A
ATOM     45  N    THR  A   79      44.184   −0.713  −40.755  1.00  36.81  A
ATOM     46  CA   THR  A   79      43.448    0.241  −41.556  1.00  37.92  A
ATOM     47  CB   THR  A   79      43.983    1.662  −41.389  1.00  39.37  A
ATOM     48  OG1  THR  A   79      45.378    1.684  −41.710  1.00  42.97  A
ATOM     49  CG2  THR  A   79      43.770    2.143  −39.953  1.00  41.38  A
ATOM     50  C    THR  A   79      43.700   −0.247  −42.965  1.00  37.15  A
ATOM     51  O    THR  A   79      44.299   −1.298  −43.159  1.00  40.94  A
ATOM     52  N    CPR  A   80      43.288    0.520  −43.969  1.00  34.90  A
ATOM     53  CD   CPR  A   80      44.233    0.907  −45.032  1.00  33.68  A
```

-continued

| | | | | | | | | | | |
|---|---|---|---|---|---|---|---|---|---|---|
| ATOM | 54 | CA | CPR | A | 80 | 41.941 | 0.367 | −44.515 | 1.00 | 31.75 A |
| ATOM | 55 | CB | CPR | A | 80 | 42.189 | 0.321 | −46.016 | 1.00 | 32.26 A |
| ATOM | 56 | CG | CPR | A | 80 | 43.316 | 1.267 | −46.177 | 1.00 | 34.32 A |
| ATOM | 57 | C | CPR | A | 80 | 41.207 | −0.880 | −44.023 | 1.00 | 29.73 A |
| ATOM | 58 | O | CPR | A | 80 | 41.726 | −1.994 | −44.105 | 1.00 | 28.01 A |
| ATOM | 59 | N | LEU | A | 81 | 40.000 | −0.684 | −43.504 | 1.00 | 26.29 A |
| ATOM | 60 | CA | LEU | A | 81 | 39.187 | −1.805 | −43.067 | 1.00 | 24.35 A |
| ATOM | 61 | CB | LEU | A | 81 | 38.007 | −1.326 | −42.218 | 1.00 | 20.43 A |
| ATOM | 62 | CG | LEU | A | 81 | 38.345 | −0.696 | −40.868 | 1.00 | 18.48 A |
| ATOM | 63 | CD1 | LEU | A | 81 | 37.074 | −0.120 | −40.242 | 1.00 | 10.91 A |
| ATOM | 64 | CD2 | LEU | A | 81 | 39.000 | −1.749 | −39.969 | 1.00 | 15.22 A |
| ATOM | 65 | C | LEU | A | 81 | 38.660 | −2.430 | −44.352 | 1.00 | 24.72 A |
| ATOM | 66 | O | LEU | A | 81 | 38.610 | −1.772 | −45.392 | 1.00 | 22.96 A |
| ATOM | 67 | N | LYS | A | 82 | 38.276 | −3.698 | −44.281 | 1.00 | 26.20 A |
| ATOM | 68 | CA | LYS | A | 82 | 37.738 | −4.402 | −45.441 | 1.00 | 26.69 A |
| ATOM | 69 | CB | LYS | A | 82 | 38.682 | −5.540 | −45.852 | 1.00 | 28.51 A |
| ATOM | 70 | CG | LYS | A | 82 | 38.188 | −6.384 | −47.022 | 1.00 | 34.36 A |
| ATOM | 71 | CD | LYS | A | 82 | 39.217 | −7.445 | −47.429 | 1.00 | 37.34 A |
| ATOM | 72 | CE | LYS | A | 82 | 38.722 | −8.278 | −48.609 | 1.00 | 39.22 A |
| ATOM | 73 | NZ | LYS | A | 82 | 39.762 | −9.208 | −49.129 | 1.00 | 41.01 A |
| ATOM | 74 | C | LYS | A | 82 | 36.366 | −4.955 | −45.059 | 1.00 | 25.07 A |
| ATOM | 75 | O | LYS | A | 82 | 36.169 | −5.422 | −43.940 | 1.00 | 25.23 A |
| ATOM | 76 | N | ILE | A | 83 | 35.417 | −4.896 | −45.986 | 1.00 | 22.76 A |
| ATOM | 77 | CA | ILE | A | 83 | 34.074 | −5.387 | −45.713 | 1.00 | 20.03 A |
| ATOM | 78 | CB | ILE | A | 83 | 33.061 | −4.820 | −46.717 | 1.00 | 17.56 A |
| ATOM | 79 | CG2 | ILE | A | 83 | 31.687 | −5.395 | −46.443 | 1.00 | 14.23 A |
| ATOM | 80 | CG1 | ILE | A | 83 | 33.050 | −3.292 | −46.642 | 1.00 | 14.83 A |
| ATOM | 81 | CD1 | ILE | A | 83 | 32.504 | −2.738 | −45.351 | 1.00 | 18.36 A |
| ATOM | 82 | C | ILE | A | 83 | 34.007 | −6.905 | −45.770 | 1.00 | 19.27 A |
| ATOM | 83 | O | ILE | A | 83 | 34.519 | −7.520 | −46.697 | 1.00 | 20.95 A |
| ATOM | 84 | N | VAL | A | 84 | 33.369 | −7.498 | −44.770 | 1.00 | 18.88 A |
| ATOM | 85 | CA | VAL | A | 84 | 33.209 | −8.943 | −44.689 | 1.00 | 18.55 A |
| ATOM | 86 | CB | VAL | A | 84 | 33.199 | −9.409 | −43.220 | 1.00 | 18.38 A |
| ATOM | 87 | CG1 | VAL | A | 84 | 32.826 | −10.874 | −43.136 | 1.00 | 17.47 A |
| ATOM | 88 | CG2 | VAL | A | 84 | 34.566 | −9.166 | −42.593 | 1.00 | 16.32 A |
| ATOM | 89 | C | VAL | A | 84 | 31.877 | −9.299 | −45.343 | 1.00 | 19.91 A |
| ATOM | 90 | O | VAL | A | 84 | 30.832 | −8.759 | −44.972 | 1.00 | 21.19 A |
| ATOM | 91 | N | GLU | A | 85 | 31.912 | −10.210 | −46.311 | 1.00 | 19.07 A |
| ATOM | 92 | CA | GLU | A | 85 | 30.700 | −10.597 | −47.022 | 1.00 | 18.15 A |
| ATOM | 93 | CB | GLU | A | 85 | 30.957 | −10.620 | −48.535 | 1.00 | 19.75 A |
| ATOM | 94 | CG | GLU | A | 85 | 31.242 | −9.268 | −49.179 | 1.00 | 20.83 A |
| ATOM | 95 | CD | GLU | A | 85 | 31.658 | −9.413 | −50.642 | 1.00 | 24.60 A |
| ATOM | 96 | OE1 | GLU | A | 85 | 31.043 | −10.251 | −51.350 | 1.00 | 24.61 A |
| ATOM | 97 | OE2 | GLU | A | 85 | 32.587 | −8.691 | −51.086 | 1.00 | 23.72 A |
| ATOM | 98 | C | GLU | A | 85 | 30.144 | −11.948 | −46.615 | 1.00 | 16.54 A |
| ATOM | 99 | O | GLU | A | 85 | 30.891 | −12.871 | −46.289 | 1.00 | 15.61 A |
| ATOM | 100 | N | TYR | A | 86 | 28.816 | −12.040 | −46.642 | 1.00 | 14.81 A |
| ATOM | 101 | CA | TYR | A | 86 | 28.086 | −13.273 | −46.342 | 1.00 | 13.38 A |
| ATOM | 102 | CB | TYR | A | 86 | 26.585 | −13.045 | −46.614 | 1.00 | 13.37 A |
| ATOM | 103 | CG | TYR | A | 86 | 25.740 | −14.294 | −46.671 | 1.00 | 11.64 A |
| ATOM | 104 | CD1 | TYR | A | 86 | 25.387 | −14.988 | −45.508 | 1.00 | 12.48 A |
| ATOM | 105 | CE1 | TYR | A | 86 | 24.653 | −16.180 | −45.576 | 1.00 | 9.76 A |
| ATOM | 106 | CD2 | TYR | A | 86 | 25.330 | −14.815 | −47.900 | 1.00 | 10.58 A |
| ATOM | 107 | CE2 | TYR | A | 86 | 24.602 | −15.993 | −47.979 | 1.00 | 7.91 A |
| ATOM | 108 | CZ | TYR | A | 86 | 24.271 | −16.676 | −46.821 | 1.00 | 9.19 A |
| ATOM | 109 | OH | TYR | A | 86 | 23.624 | −17.891 | −46.923 | 1.00 | 9.80 A |
| ATOM | 110 | C | TYR | A | 86 | 28.660 | −14.288 | −47.326 | 1.00 | 11.79 A |
| ATOM | 111 | O | TYR | A | 86 | 29.028 | −13.922 | −48.443 | 1.00 | 9.00 A |
| ATOM | 112 | N | PRO | A | 87 | 28.737 | −15.571 | −46.940 | 1.00 | 13.07 A |
| ATOM | 113 | CD | PRO | A | 87 | 29.187 | −16.597 | −47.904 | 1.00 | 12.32 A |
| ATOM | 114 | CA | PRO | A | 87 | 28.335 | −16.193 | −45.672 | 1.00 | 14.67 A |
| ATOM | 115 | CB | PRO | A | 87 | 27.876 | −17.563 | −46.122 | 1.00 | 13.93 A |
| ATOM | 116 | CG | PRO | A | 87 | 28.972 | −17.908 | −47.144 | 1.00 | 13.84 A |
| ATOM | 117 | C | PRO | A | 87 | 29.449 | −16.289 | −44.612 | 1.00 | 16.37 A |
| ATOM | 118 | O | PRO | A | 87 | 29.415 | −17.176 | −43.751 | 1.00 | 16.16 A |
| ATOM | 119 | N | ASP | A | 88 | 30.433 | −15.396 | −44.676 | 1.00 | 14.88 A |
| ATOM | 120 | CA | ASP | A | 88 | 31.529 | −15.427 | −43.708 | 1.00 | 16.94 A |
| ATOM | 121 | CB | ASP | A | 88 | 32.374 | −14.155 | −43.811 | 1.00 | 17.27 A |
| ATOM | 122 | CG | ASP | A | 88 | 33.647 | −14.237 | −42.991 | 1.00 | 20.01 A |
| ATOM | 123 | OD1 | ASP | A | 88 | 33.564 | −14.530 | −41.779 | 1.00 | 22.56 A |
| ATOM | 124 | OD2 | ASP | A | 88 | 34.734 | −14.005 | −43.559 | 1.00 | 22.48 A |
| ATOM | 125 | C | ASP | A | 88 | 30.964 | −15.563 | −42.286 | 1.00 | 17.02 A |
| ATOM | 126 | O | ASP | A | 88 | 30.111 | −14.771 | −41.864 | 1.00 | 14.24 A |
| ATOM | 127 | N | PRO | A | 89 | 31.454 | −16.562 | −41.528 | 1.00 | 17.30 A |
| ATOM | 128 | CD | PRO | A | 89 | 32.572 | −17.414 | −41.972 | 1.00 | 17.85 A |
| ATOM | 129 | CA | PRO | A | 89 | 31.063 | −16.896 | −40.148 | 1.00 | 16.77 A |
| ATOM | 130 | CB | PRO | A | 89 | 32.039 | −18.014 | −39.769 | 1.00 | 17.99 A |
| ATOM | 131 | CG | PRO | A | 89 | 32.412 | −18.623 | −41.091 | 1.00 | 19.05 A |
| ATOM | 132 | C | PRO | A | 89 | 31.102 | −15.742 | −39.141 | 1.00 | 17.05 A |

| | | | | | | | | | | |
|---|---|---|---|---|---|---|---|---|---|---|
| | | | -continued | | | | | | | |
| ATOM | 133 | O | PRO | A | 89 | 30.343 | −15.737 | −38.167 | 1.00 | 14.98 A |
| ATOM | 134 | N | ILE | A | 90 | 31.997 | −14.781 | −39.371 | 1.00 | 16.08 A |
| ATOM | 135 | CA | ILE | A | 90 | 32.138 | −13.624 | −38.489 | 1.00 | 15.58 A |
| ATOM | 136 | CB | ILE | A | 90 | 33.228 | −12.657 | −39.019 | 1.00 | 14.80 A |
| ATOM | 137 | CG2 | ILE | A | 90 | 33.261 | −11.394 | −38.178 | 1.00 | 12.19 A |
| ATOM | 138 | CG1 | ILE | A | 90 | 34.596 | −13.344 | −38.983 | 1.00 | 15.77 A |
| ATOM | 139 | CD1 | ILE | A | 90 | 35.729 | −12.544 | −39.637 | 1.00 | 14.96 A |
| ATOM | 140 | C | ILE | A | 90 | 30.823 | −12.853 | −38.332 | 1.00 | 15.25 A |
| ATOM | 141 | O | ILE | A | 90 | 30.595 | −12.190 | −37.318 | 1.00 | 13.85 A |
| ATOM | 142 | N | LEU | A | 91 | 29.951 | −12.960 | −39.329 | 1.00 | 13.85 A |
| ATOM | 143 | CA | LEU | A | 91 | 28.679 | −12.262 | −39.295 | 1.00 | 12.86 A |
| ATOM | 144 | CB | LEU | A | 91 | 28.124 | −12.129 | −40.709 | 1.00 | 8.77 A |
| ATOM | 145 | CG | LEU | A | 91 | 29.118 | −11.425 | −41.639 | 1.00 | 8.91 A |
| ATOM | 146 | CD1 | LEU | A | 91 | 28.533 | −11.337 | −43.034 | 1.00 | 9.63 A |
| ATOM | 147 | CD2 | LEU | A | 91 | 29.460 | −10.035 | −41.096 | 1.00 | 7.28 A |
| ATOM | 148 | C | LEU | A | 91 | 27.666 | −12.934 | −38.383 | 1.00 | 14.00 A |
| ATOM | 149 | O | LEU | A | 91 | 26.585 | −12.392 | −38.147 | 1.00 | 15.75 A |
| ATOM | 150 | N | ARG | A | 92 | 28.024 | −14.102 | −37.856 | 1.00 | 14.41 A |
| ATOM | 151 | CA | ARG | A | 92 | 27.142 | −14.841 | −36.946 | 1.00 | 16.37 A |
| ATOM | 152 | CB | ARG | A | 92 | 26.771 | −16.202 | −37.541 | 1.00 | 17.16 A |
| ATOM | 153 | CG | ARG | A | 92 | 26.132 | −16.163 | −38.904 | 1.00 | 17.07 A |
| ATOM | 154 | CD | ARG | A | 92 | 24.720 | −15.650 | −38.825 | 1.00 | 17.49 A |
| ATOM | 155 | NE | ARG | A | 92 | 23.973 | −15.900 | −40.058 | 1.00 | 16.77 A |
| ATOM | 156 | CZ | ARG | A | 92 | 22.704 | −15.549 | −40.237 | 1.00 | 15.33 A |
| ATOM | 157 | NH1 | ARG | A | 92 | 22.042 | −14.928 | −39.263 | 1.00 | 15.95 A |
| ATOM | 158 | NH2 | ARG | A | 92 | 22.093 | −15.828 | −41.378 | 1.00 | 15.85 A |
| ATOM | 159 | C | ARG | A | 92 | 27.832 | −15.099 | −35.609 | 1.00 | 16.73 A |
| ATOM | 160 | O | ARG | A | 92 | 27.185 | −15.475 | −34.636 | 1.00 | 16.22 A |
| ATOM | 161 | N | ALA | A | 93 | 29.142 | −14.874 | −35.582 | 1.00 | 18.23 A |
| ATOM | 162 | CA | ALA | A | 93 | 30.006 | −15.132 | −34.425 | 1.00 | 22.48 A |
| ATOM | 163 | CB | ALA | A | 93 | 31.457 | −14.786 | −34.797 | 1.00 | 23.31 A |
| ATOM | 164 | C | ALA | A | 93 | 29.726 | −14.602 | −33.015 | 1.00 | 24.67 A |
| ATOM | 165 | O | ALA | A | 93 | 30.506 | −14.902 | −32.106 | 1.00 | 28.53 A |
| ATOM | 166 | N | LYS | A | 94 | 28.665 | −13.833 | −32.799 | 1.00 | 24.09 A |
| ATOM | 167 | CA | LYS | A | 94 | 28.384 | −13.346 | −31.439 | 1.00 | 24.96 A |
| ATOM | 168 | CB | LYS | A | 94 | 28.436 | −14.500 | −30.437 | 1.00 | 25.30 A |
| ATOM | 169 | CG | LYS | A | 94 | 28.341 | −14.049 | −29.000 | 1.00 | 29.01 A |
| ATOM | 170 | CD | LYS | A | 94 | 29.295 | −14.836 | −28.131 | 1.00 | 32.16 A |
| ATOM | 171 | CE | LYS | A | 94 | 29.502 | −14.124 | −26.805 | 1.00 | 33.93 A |
| ATOM | 172 | NZ | LYS | A | 94 | 29.929 | −12.709 | −27.033 | 1.00 | 34.32 A |
| ATOM | 173 | C | LYS | A | 94 | 29.371 | −12.256 | −31.016 | 1.00 | 22.46 A |
| ATOM | 174 | O | LYS | A | 94 | 30.581 | −12.475 | −30.959 | 1.00 | 21.86 A |
| ATOM | 175 | N | ASN | A | 95 | 28.832 | −11.093 | −30.673 | 1.00 | 21.41 A |
| ATOM | 176 | CA | ASN | A | 95 | 29.657 | −9.946 | −30.341 | 1.00 | 22.01 A |
| ATOM | 177 | CB | ASN | A | 95 | 29.187 | −8.774 | −31.208 | 1.00 | 20.42 A |
| ATOM | 178 | CG | ASN | A | 95 | 28.983 | −9.187 | −32.651 | 1.00 | 19.92 A |
| ATOM | 179 | OD1 | ASN | A | 95 | 27.859 | −9.463 | −33.085 | 1.00 | 18.30 A |
| ATOM | 180 | ND2 | ASN | A | 95 | 30.081 | −9.268 | −33.397 | 1.00 | 20.07 A |
| ATOM | 181 | C | ASN | A | 95 | 29.774 | −9.517 | −28.884 | 1.00 | 21.39 A |
| ATOM | 182 | O | ASN | A | 95 | 28.777 | −9.287 | −28.199 | 1.00 | 20.41 A |
| ATOM | 183 | N | LYS | A | 96 | 31.019 | −9.395 | −28.434 | 1.00 | 23.00 A |
| ATOM | 184 | CA | LYS | A | 96 | 31.334 | −8.989 | −27.071 | 1.00 | 23.73 A |
| ATOM | 185 | CB | LYS | A | 96 | 32.779 | −9.351 | −26.732 | 1.00 | 25.32 A |
| ATOM | 186 | CG | LYS | A | 96 | 33.051 | −10.845 | −26.646 | 1.00 | 26.59 A |
| ATOM | 187 | CD | LYS | A | 96 | 34.537 | −11.110 | −26.428 | 1.00 | 30.79 A |
| ATOM | 188 | CE | LYS | A | 96 | 34.831 | −12.599 | −26.255 | 1.00 | 32.28 A |
| ATOM | 189 | NZ | LYS | A | 96 | 36.296 | −12.888 | −26.289 | 1.00 | 32.84 A |
| ATOM | 190 | C | LYS | A | 96 | 31.135 | −7.492 | −26.874 | 1.00 | 25.90 A |
| ATOM | 191 | O | LYS | A | 96 | 31.421 | −6.686 | −27.769 | 1.00 | 25.26 A |
| ATOM | 192 | N | ARG | A | 97 | 30.642 | −7.134 | −25.692 | 1.00 | 26.74 A |
| ATOM | 193 | CA | ARG | A | 97 | 30.402 | −5.743 | −25.336 | 1.00 | 27.69 A |
| ATOM | 194 | CB | ARG | A | 97 | 29.702 | −5.662 | −23.979 | 1.00 | 28.92 A |
| ATOM | 195 | CG | ARG | A | 97 | 28.317 | −6.287 | −23.952 | 1.00 | 33.87 A |
| ATOM | 196 | CD | ARG | A | 97 | 27.813 | −6.493 | −22.525 | 1.00 | 37.61 A |
| ATOM | 197 | NE | ARG | A | 97 | 28.062 | −5.314 | −21.706 | 1.00 | 39.27 A |
| ATOM | 198 | CZ | ARG | A | 97 | 29.170 | −5.119 | −20.999 | 1.00 | 40.73 A |
| ATOM | 199 | NH1 | ARG | A | 97 | 30.132 | −6.035 | −20.995 | 1.00 | 41.21 A |
| ATOM | 200 | NH2 | ARG | A | 97 | 29.334 | −3.987 | −20.330 | 1.00 | 40.81 A |
| ATOM | 201 | C | ARG | A | 97 | 31.730 | −5.009 | −25.262 | 1.00 | 27.45 A |
| ATOM | 202 | O | ARG | A | 97 | 32.773 | −5.619 | −25.014 | 1.00 | 27.82 A |
| ATOM | 203 | N | ILE | A | 98 | 31.689 | −3.702 | −25.487 | 1.00 | 25.11 A |
| ATOM | 204 | CA | ILE | A | 98 | 32.889 | −2.888 | −25.426 | 1.00 | 24.66 A |
| ATOM | 205 | CB | ILE | A | 98 | 32.866 | −1.803 | −26.529 | 1.00 | 24.88 A |
| ATOM | 206 | CG2 | ILE | A | 98 | 33.965 | −0.767 | −26.301 | 1.00 | 20.36 A |
| ATOM | 207 | CG1 | ILE | A | 98 | 33.044 | −2.485 | −27.891 | 1.00 | 24.66 A |
| ATOM | 208 | CD1 | ILE | A | 98 | 33.092 | −1.538 | −29.061 | 1.00 | 28.24 A |
| ATOM | 209 | C | ILE | A | 98 | 32.997 | −2.267 | −24.035 | 1.00 | 24.19 A |
| ATOM | 210 | O | ILE | A | 98 | 32.093 | −1.571 | −23.581 | 1.00 | 24.25 A |
| ATOM | 211 | N | ASP | A | 99 | 34.104 | −2.549 | −23.359 | 1.00 | 23.56 A |

-continued

| | | | | | | | | | | |
|---|---|---|---|---|---|---|---|---|---|---|
| ATOM | 212 | CA  | ASP | A | 99  | 34.339 | −2.053 | −22.008 | 1.00 | 23.39 A |
| ATOM | 213 | CB  | ASP | A | 99  | 34.250 | −3.214 | −21.018 | 1.00 | 23.94 A |
| ATOM | 214 | CG  | ASP | A | 99  | 35.163 | −4.366 | −21.394 | 1.00 | 24.05 A |
| ATOM | 215 | OD1 | ASP | A | 99  | 35.055 | −5.439 | −20.766 | 1.00 | 24.51 A |
| ATOM | 216 | OD2 | ASP | A | 99  | 35.991 | −4.196 | −22.318 | 1.00 | 23.12 A |
| ATOM | 217 | C   | ASP | A | 99  | 35.699 | −1.370 | −21.880 | 1.00 | 23.34 A |
| ATOM | 218 | O   | ASP | A | 99  | 36.285 | −1.317 | −20.800 | 1.00 | 21.90 A |
| ATOM | 219 | N   | ILE | A | 100 | 36.204 | −0.875 | −23.002 | 1.00 | 22.91 A |
| ATOM | 220 | CA  | ILE | A | 100 | 37.469 | −0.161 | −23.033 | 1.00 | 22.92 A |
| ATOM | 221 | CB  | ILE | A | 100 | 38.647 | −1.068 | −23.461 | 1.00 | 21.59 A |
| ATOM | 222 | CG2 | ILE | A | 100 | 39.872 | −0.209 | −23.780 | 1.00 | 21.34 A |
| ATOM | 223 | CG1 | ILE | A | 100 | 38.960 | −2.072 | −22.342 | 1.00 | 20.46 A |
| ATOM | 224 | CD1 | ILE | A | 100 | 40.247 | −2.845 | −22.530 | 1.00 | 16.61 A |
| ATOM | 225 | C   | ILE | A | 100 | 37.292 | 0.975  | −24.026 | 1.00 | 23.77 A |
| ATOM | 226 | O   | ILE | A | 100 | 37.268 | 0.767  | −25.243 | 1.00 | 22.69 A |
| ATOM | 227 | N   | PHE | A | 101 | 37.145 | 2.179  | −23.489 | 1.00 | 23.83 A |
| ATOM | 228 | CA  | PHE | A | 101 | 36.934 | 3.360  | −24.308 | 1.00 | 24.41 A |
| ATOM | 229 | CB  | PHE | A | 101 | 35.788 | 4.175  | −23.705 | 1.00 | 23.98 A |
| ATOM | 230 | CG  | PHE | A | 101 | 34.559 | 3.343  | −23.419 | 1.00 | 24.14 A |
| ATOM | 231 | CD1 | PHE | A | 101 | 34.480 | 2.567  | −22.261 | 1.00 | 25.77 A |
| ATOM | 232 | CD2 | PHE | A | 101 | 33.517 | 3.274  | −24.339 | 1.00 | 23.97 A |
| ATOM | 233 | CE1 | PHE | A | 101 | 33.379 | 1.729  | −22.025 | 1.00 | 26.25 A |
| ATOM | 234 | CE2 | PHE | A | 101 | 32.413 | 2.444  | −24.115 | 1.00 | 24.68 A |
| ATOM | 235 | CZ  | PHE | A | 101 | 32.344 | 1.669  | −22.958 | 1.00 | 24.94 A |
| ATOM | 236 | C   | PHE | A | 101 | 38.227 | 4.152  | −24.398 | 1.00 | 24.03 A |
| ATOM | 237 | O   | PHE | A | 101 | 38.514 | 5.009  | −23.565 | 1.00 | 24.43 A |
| ATOM | 238 | N   | ASP | A | 102 | 39.002 | 3.840  | −25.435 | 1.00 | 23.26 A |
| ATOM | 239 | CA  | ASP | A | 102 | 40.301 | 4.458  | −25.658 | 1.00 | 22.30 A |
| ATOM | 240 | CB  | ASP | A | 102 | 41.408 | 3.437  | −25.360 | 1.00 | 22.09 A |
| ATOM | 241 | CG  | ASP | A | 102 | 41.328 | 2.199  | −26.256 | 1.00 | 20.92 A |
| ATOM | 242 | OD1 | ASP | A | 102 | 40.445 | 2.141  | −27.143 | 1.00 | 18.72 A |
| ATOM | 243 | OD2 | ASP | A | 102 | 42.158 | 1.279  | −26.072 | 1.00 | 20.13 A |
| ATOM | 244 | C   | ASP | A | 102 | 40.495 | 4.990  | −27.066 | 1.00 | 21.70 A |
| ATOM | 245 | O   | ASP | A | 102 | 39.567 | 5.025  | −27.868 | 1.00 | 22.38 A |
| ATOM | 246 | N   | GLU | A | 103 | 41.728 | 5.398  | −27.349 | 1.00 | 22.47 A |
| ATOM | 247 | CA  | GLU | A | 103 | 42.108 | 5.927  | −28.653 | 1.00 | 21.29 A |
| ATOM | 248 | CB  | GLU | A | 103 | 43.610 | 6.188  | −28.705 | 1.00 | 19.68 A |
| ATOM | 249 | CG  | GLU | A | 103 | 43.965 | 7.635  | −28.642 | 1.00 | 21.47 A |
| ATOM | 250 | CD  | GLU | A | 103 | 43.305 | 8.423  | −29.741 | 1.00 | 21.50 A |
| ATOM | 251 | OE1 | GLU | A | 103 | 42.668 | 9.445  | −29.427 | 1.00 | 20.68 A |
| ATOM | 252 | OE2 | GLU | A | 103 | 43.427 | 8.020  | −30.914 | 1.00 | 22.92 A |
| ATOM | 253 | C   | GLU | A | 103 | 41.764 | 4.954  | −29.754 | 1.00 | 20.91 A |
| ATOM | 254 | O   | GLU | A | 103 | 41.172 | 5.331  | −30.767 | 1.00 | 19.57 A |
| ATOM | 255 | N   | ASN | A | 104 | 42.172 | 3.705  | −29.550 | 1.00 | 21.14 A |
| ATOM | 256 | CA  | ASN | A | 104 | 41.937 | 2.639  | −30.507 | 1.00 | 22.17 A |
| ATOM | 257 | CB  | ASN | A | 104 | 42.341 | 1.299  | −29.897 | 1.00 | 26.29 A |
| ATOM | 258 | CG  | ASN | A | 104 | 43.312 | 0.541  | −30.766 | 1.00 | 29.79 A |
| ATOM | 259 | OD1 | ASN | A | 104 | 43.027 | 0.261  | −31.930 | 1.00 | 33.45 A |
| ATOM | 260 | ND2 | ASN | A | 104 | 44.473 | 0.204  | −30.208 | 1.00 | 30.61 A |
| ATOM | 261 | C   | ASN | A | 104 | 40.473 | 2.593  | −30.920 | 1.00 | 22.03 A |
| ATOM | 262 | O   | ASN | A | 104 | 40.160 | 2.479  | −32.108 | 1.00 | 21.05 A |
| ATOM | 263 | N   | LEU | A | 105 | 39.581 | 2.684  | −29.934 | 1.00 | 19.85 A |
| ATOM | 264 | CA  | LEU | A | 105 | 38.150 | 2.657  | −30.199 | 1.00 | 19.86 A |
| ATOM | 265 | CB  | LEU | A | 105 | 37.358 | 2.735  | −28.886 | 1.00 | 21.38 A |
| ATOM | 266 | CG  | LEU | A | 105 | 35.919 | 2.188  | −28.821 | 1.00 | 21.48 A |
| ATOM | 267 | CD1 | LEU | A | 105 | 35.056 | 3.165  | −28.032 | 1.00 | 21.52 A |
| ATOM | 268 | CD2 | LEU | A | 105 | 35.341 | 1.980  | −30.207 | 1.00 | 21.83 A |
| ATOM | 269 | C   | LEU | A | 105 | 37.771 | 3.830  | −31.102 | 1.00 | 19.11 A |
| ATOM | 270 | O   | LEU | A | 105 | 36.987 | 3.668  | −32.036 | 1.00 | 19.29 A |
| ATOM | 271 | N   | LYS | A | 106 | 38.328 | 5.008  | −30.820 | 1.00 | 17.86 A |
| ATOM | 272 | CA  | LYS | A | 106 | 38.051 | 6.194  | −31.627 | 1.00 | 18.70 A |
| ATOM | 273 | CB  | LYS | A | 106 | 38.639 | 7.449  | −30.974 | 1.00 | 18.90 A |
| ATOM | 274 | CG  | LYS | A | 106 | 38.329 | 8.737  | −31.744 | 1.00 | 21.08 A |
| ATOM | 275 | CD  | LYS | A | 106 | 38.916 | 9.962  | −31.051 | 1.00 | 20.57 A |
| ATOM | 276 | CE  | LYS | A | 106 | 40.425 | 10.037 | −31.200 | 1.00 | 19.98 A |
| ATOM | 277 | NZ  | LYS | A | 106 | 41.013 | 11.166 | −30.404 | 1.00 | 18.10 A |
| ATOM | 278 | C   | LYS | A | 106 | 38.597 | 6.061  | −33.058 | 1.00 | 18.80 A |
| ATOM | 279 | O   | LYS | A | 106 | 37.914 | 6.413  | −34.023 | 1.00 | 18.37 A |
| ATOM | 280 | N   | ASN | A | 107 | 39.822 | 5.556  | −33.190 | 1.00 | 17.20 A |
| ATOM | 281 | CA  | ASN | A | 107 | 40.431 | 5.370  | −34.506 | 1.00 | 18.47 A |
| ATOM | 282 | CB  | ASN | A | 107 | 41.857 | 4.814  | −34.363 | 1.00 | 21.05 A |
| ATOM | 283 | CG  | ASN | A | 107 | 42.777 | 5.725  | −33.544 | 1.00 | 24.77 A |
| ATOM | 284 | OD1 | ASN | A | 107 | 43.803 | 5.275  | −33.021 | 1.00 | 26.42 A |
| ATOM | 285 | ND2 | ASN | A | 107 | 42.423 | 7.005  | −33.441 | 1.00 | 23.25 A |
| ATOM | 286 | C   | ASN | A | 107 | 39.587 | 4.394  | −35.332 | 1.00 | 17.56 A |
| ATOM | 287 | O   | ASN | A | 107 | 39.453 | 4.543  | −36.545 | 1.00 | 17.37 A |
| ATOM | 288 | N   | LEU | A | 108 | 39.008 | 3.401  | −34.659 | 1.00 | 18.87 A |
| ATOM | 289 | CA  | LEU | A | 108 | 38.182 | 2.393  | −35.315 | 1.00 | 18.66 A |
| ATOM | 290 | CB  | LEU | A | 108 | 37.754 | 1.318  | −34.310 | 1.00 | 17.82 A |

-continued

| | | | | | | | | | | |
|---|---|---|---|---|---|---|---|---|---|---|
| ATOM | 291 | CG | LEU | A | 108 | 37.452 | −0.094 | −34.834 | 1.00 | 18.20 A |
| ATOM | 292 | CD1 | LEU | A | 108 | 36.611 | −0.846 | −33.809 | 1.00 | 14.71 A |
| ATOM | 293 | CD2 | LEU | A | 108 | 36.712 | −0.033 | −36.137 | 1.00 | 16.41 A |
| ATOM | 294 | C | LEU | A | 108 | 36.938 | 3.025 | −35.936 | 1.00 | 19.55 A |
| ATOM | 295 | O | LEU | A | 108 | 36.669 | 2.851 | −37.127 | 1.00 | 20.36 A |
| ATOM | 296 | N | VAL | A | 109 | 36.183 | 3.752 | −35.117 | 1.00 | 19.78 A |
| ATOM | 297 | CA | VAL | A | 109 | 34.961 | 4.412 | −35.567 | 1.00 | 20.39 A |
| ATOM | 298 | CB | VAL | A | 109 | 34.391 | 5.350 | −34.460 | 1.00 | 20.97 A |
| ATOM | 299 | CG1 | VAL | A | 109 | 33.245 | 6.201 | −35.014 | 1.00 | 18.35 A |
| ATOM | 300 | CG2 | VAL | A | 109 | 33.908 | 4.514 | −33.282 | 1.00 | 18.10 A |
| ATOM | 301 | C | VAL | A | 109 | 35.207 | 5.218 | −36.841 | 1.00 | 21.06 A |
| ATOM | 302 | O | VAL | A | 109 | 34.448 | 5.104 | −37.815 | 1.00 | 20.21 A |
| ATOM | 303 | N | ASP | A | 110 | 36.268 | 6.021 | −36.833 | 1.00 | 19.90 A |
| ATOM | 304 | CA | ASP | A | 110 | 36.609 | 6.834 | −37.993 | 1.00 | 19.28 A |
| ATOM | 305 | CB | ASP | A | 110 | 37.787 | 7.760 | −37.665 | 1.00 | 21.34 A |
| ATOM | 306 | CG | ASP | A | 110 | 38.385 | 8.412 | −38.904 | 1.00 | 23.52 A |
| ATOM | 307 | OD1 | ASP | A | 110 | 39.280 | 7.805 | −39.525 | 1.00 | 23.06 A |
| ATOM | 308 | OD2 | ASP | A | 110 | 37.950 | 9.526 | −39.264 | 1.00 | 25.77 A |
| ATOM | 309 | C | ASP | A | 110 | 36.954 | 5.948 | −39.187 | 1.00 | 18.12 A |
| ATOM | 310 | O | ASP | A | 110 | 36.606 | 6.260 | −40.326 | 1.00 | 16.99 A |
| ATOM | 311 | N | ALA | A | 111 | 37.640 | 4.842 | −38.928 | 1.00 | 17.77 A |
| ATOM | 312 | CA | ALA | A | 111 | 38.007 | 3.934 | −40.014 | 1.00 | 18.12 A |
| ATOM | 313 | CB | ALA | A | 111 | 38.991 | 2.879 | −39.517 | 1.00 | 17.41 A |
| ATOM | 314 | C | ALA | A | 111 | 36.747 | 3.265 | −40.559 | 1.00 | 18.06 A |
| ATOM | 315 | O | ALA | A | 111 | 36.688 | 2.909 | −41.735 | 1.00 | 17.71 A |
| ATOM | 316 | N | MET | A | 112 | 35.741 | 3.093 | −39.700 | 1.00 | 16.57 A |
| ATOM | 317 | CA | MET | A | 112 | 34.493 | 2.476 | −40.131 | 1.00 | 16.68 A |
| ATOM | 318 | CB | MET | A | 112 | 33.625 | 2.094 | −38.932 | 1.00 | 16.96 A |
| ATOM | 319 | CG | MET | A | 112 | 34.095 | 0.844 | −38.224 | 1.00 | 15.01 A |
| ATOM | 320 | SD | MET | A | 112 | 33.117 | 0.488 | −36.768 | 1.00 | 19.27 A |
| ATOM | 321 | CE | MET | A | 112 | 31.718 | −0.406 | −37.514 | 1.00 | 17.01 A |
| ATOM | 322 | C | MET | A | 112 | 33.729 | 3.421 | −41.036 | 1.00 | 16.16 A |
| ATOM | 323 | O | MET | A | 112 | 33.206 | 3.009 | −42.072 | 1.00 | 16.11 A |
| ATOM | 324 | N | PHE | A | 113 | 33.661 | 4.688 | −40.643 | 1.00 | 16.28 A |
| ATOM | 325 | CA | PHE | A | 113 | 32.965 | 5.674 | −41.458 | 1.00 | 18.18 A |
| ATOM | 326 | CB | PHE | A | 113 | 32.955 | 7.054 | −40.770 | 1.00 | 16.66 A |
| ATOM | 327 | CG | PHE | A | 113 | 31.803 | 7.259 | −39.806 | 1.00 | 14.71 A |
| ATOM | 328 | CD1 | PHE | A | 113 | 30.482 | 7.154 | −40.239 | 1.00 | 14.21 A |
| ATOM | 329 | CD2 | PHE | A | 113 | 32.041 | 7.552 | −38.457 | 1.00 | 15.65 A |
| ATOM | 330 | CE1 | PHE | A | 113 | 29.406 | 7.334 | −39.341 | 1.00 | 12.91 A |
| ATOM | 331 | CE2 | PHE | A | 113 | 30.979 | 7.735 | −37.554 | 1.00 | 13.65 A |
| ATOM | 332 | CZ | PHE | A | 113 | 29.658 | 7.624 | −38.001 | 1.00 | 13.65 A |
| ATOM | 333 | C | PHE | A | 113 | 33.674 | 5.763 | −42.813 | 1.00 | 19.19 A |
| ATOM | 334 | O | PHE | A | 113 | 33.036 | 5.966 | −43.848 | 1.00 | 20.51 A |
| ATOM | 335 | N | ASP | A | 114 | 34.993 | 5.593 | −42.809 | 1.00 | 19.06 A |
| ATOM | 336 | CA | ASP | A | 114 | 35.752 | 5.671 | −44.050 | 1.00 | 19.17 A |
| ATOM | 337 | CB | ASP | A | 114 | 37.258 | 5.516 | −43.800 | 1.00 | 19.27 A |
| ATOM | 338 | CG | ASP | A | 114 | 37.847 | 6.649 | −42.972 | 1.00 | 18.16 A |
| ATOM | 339 | OD1 | ASP | A | 114 | 37.388 | 7.798 | −43.112 | 1.00 | 18.34 A |
| ATOM | 340 | OD2 | ASP | A | 114 | 38.792 | 6.383 | −42.194 | 1.00 | 16.95 A |
| ATOM | 341 | C | ASP | A | 114 | 35.328 | 4.601 | −45.047 | 1.00 | 20.74 A |
| ATOM | 342 | O | ASP | A | 114 | 34.948 | 4.905 | −46.178 | 1.00 | 22.18 A |
| ATOM | 343 | N | VAL | A | 115 | 35.402 | 3.343 | −44.635 | 1.00 | 19.76 A |
| ATOM | 344 | CA | VAL | A | 115 | 35.051 | 2.271 | −45.541 | 1.00 | 20.05 A |
| ATOM | 345 | CB | VAL | A | 115 | 35.421 | 0.882 | −44.952 | 1.00 | 18.79 A |
| ATOM | 346 | CG1 | VAL | A | 115 | 34.508 | 0.535 | −43.781 | 1.00 | 19.87 A |
| ATOM | 347 | CG2 | VAL | A | 115 | 35.348 | −0.179 | −46.047 | 1.00 | 18.66 A |
| ATOM | 348 | C | VAL | A | 115 | 33.570 | 2.319 | −45.888 | 1.00 | 20.92 A |
| ATOM | 349 | O | VAL | A | 115 | 33.172 | 1.900 | −46.976 | 1.00 | 21.72 A |
| ATOM | 350 | N | MET | A | 116 | 32.756 | 2.843 | −44.975 | 1.00 | 20.52 A |
| ATOM | 351 | CA | MET | A | 116 | 31.324 | 2.928 | −45.225 | 1.00 | 20.64 A |
| ATOM | 352 | CB | MET | A | 116 | 30.574 | 3.419 | −43.975 | 1.00 | 21.83 A |
| ATOM | 353 | CG | MET | A | 116 | 29.047 | 3.419 | −44.133 | 1.00 | 21.70 A |
| ATOM | 354 | SD | MET | A | 116 | 28.146 | 4.174 | −42.758 | 1.00 | 25.32 A |
| ATOM | 355 | CE | MET | A | 116 | 28.020 | 5.885 | −43.298 | 1.00 | 22.79 A |
| ATOM | 356 | C | MET | A | 116 | 31.107 | 3.896 | −46.387 | 1.00 | 21.10 A |
| ATOM | 357 | O | MET | A | 116 | 30.475 | 3.544 | −47.389 | 1.00 | 18.06 A |
| ATOM | 358 | N | TYR | A | 117 | 31.652 | 5.106 | −46.247 | 1.00 | 21.03 A |
| ATOM | 359 | CA | TYR | A | 117 | 31.537 | 6.135 | −47.275 | 1.00 | 20.92 A |
| ATOM | 360 | CB | TYR | A | 117 | 32.175 | 7.448 | −46.809 | 1.00 | 20.51 A |
| ATOM | 361 | CG | TYR | A | 117 | 31.419 | 8.154 | −45.709 | 1.00 | 18.43 A |
| ATOM | 362 | CD1 | TYR | A | 117 | 30.033 | 8.240 | −45.744 | 1.00 | 17.94 A |
| ATOM | 363 | CE1 | TYR | A | 117 | 29.328 | 8.917 | −44.754 | 1.00 | 18.18 A |
| ATOM | 364 | CD2 | TYR | A | 117 | 32.089 | 8.765 | −44.652 | 1.00 | 17.61 A |
| ATOM | 365 | CE2 | TYR | A | 117 | 31.391 | 9.450 | −43.655 | 1.00 | 17.47 A |
| ATOM | 366 | CZ | TYR | A | 117 | 30.011 | 9.518 | −43.719 | 1.00 | 16.23 A |
| ATOM | 367 | OH | TYR | A | 117 | 29.301 | 10.186 | −42.759 | 1.00 | 18.52 A |
| ATOM | 368 | C | TYR | A | 117 | 32.212 | 5.700 | −48.563 | 1.00 | 22.73 A |
| ATOM | 369 | O | TYR | A | 117 | 31.717 | 5.976 | −49.653 | 1.00 | 22.10 A |

-continued

| | | | | | | | | | |
|---|---|---|---|---|---|---|---|---|---|
| ATOM | 370 | N | LYS | A | 118 | 33.356 | 5.034 | −48.434 | 1.00 | 24.25 A |
| ATOM | 371 | CA | LYS | A | 118 | 34.091 | 4.576 | −49.602 | 1.00 | 25.84 A |
| ATOM | 372 | CB | LYS | A | 118 | 35.328 | 3.776 | −49.188 | 1.00 | 26.26 A |
| ATOM | 373 | CG | LYS | A | 118 | 36.230 | 3.407 | −50.364 | 1.00 | 30.30 A |
| ATOM | 374 | CD | LYS | A | 118 | 37.218 | 2.273 | −50.035 | 1.00 | 31.07 A |
| ATOM | 375 | CE | LYS | A | 118 | 36.496 | 0.934 | −49.841 | 1.00 | 32.32 A |
| ATOM | 376 | NZ | LYS | A | 118 | 37.410 | −0.253 | −49.726 | 1.00 | 29.48 A |
| ATOM | 377 | C | LYS | A | 118 | 33.189 | 3.687 | −50.446 | 1.00 | 27.75 A |
| ATOM | 378 | O | LYS | A | 118 | 33.102 | 3.836 | −51.667 | 1.00 | 27.33 A |
| ATOM | 379 | N | THR | A | 119 | 32.510 | 2.765 | −49.774 | 1.00 | 28.14 A |
| ATOM | 380 | CA | THR | A | 119 | 31.637 | 1.814 | −50.438 | 1.00 | 28.42 A |
| ATOM | 381 | CB | THR | A | 119 | 31.617 | 0.480 | −49.649 | 1.00 | 28.33 A |
| ATOM | 382 | OG1 | THR | A | 119 | 31.330 | 0.739 | −48.269 | 1.00 | 29.06 A |
| ATOM | 383 | CG2 | THR | A | 119 | 32.975 | −0.211 | −49.738 | 1.00 | 27.56 A |
| ATOM | 384 | C | THR | A | 119 | 30.223 | 2.354 | −50.631 | 1.00 | 29.80 A |
| ATOM | 385 | O | THR | A | 119 | 29.297 | 1.607 | −50.955 | 1.00 | 28.97 A |
| ATOM | 386 | N | ASP | A | 120 | 30.078 | 3.665 | −50.454 | 1.00 | 31.38 A |
| ATOM | 387 | CA | ASP | A | 120 | 28.790 | 4.333 | −50.605 | 1.00 | 32.18 A |
| ATOM | 388 | CB | ASP | A | 120 | 28.401 | 4.406 | −52.092 | 1.00 | 34.50 A |
| ATOM | 389 | CG | ASP | A | 120 | 29.104 | 5.544 | −52.828 | 1.00 | 38.27 A |
| ATOM | 390 | OD1 | ASP | A | 120 | 28.855 | 6.724 | −52.478 | 1.00 | 40.42 A |
| ATOM | 391 | OD2 | ASP | A | 120 | 29.905 | 5.266 | −53.752 | 1.00 | 38.92 A |
| ATOM | 392 | C | ASP | A | 120 | 27.724 | 3.599 | −49.800 | 1.00 | 30.66 A |
| ATOM | 393 | O | ASP | A | 120 | 26.683 | 3.199 | −50.323 | 1.00 | 31.17 A |
| ATOM | 394 | N | GLY | A | 121 | 28.012 | 3.415 | −48.517 | 1.00 | 28.44 A |
| ATOM | 395 | CA | GLY | A | 121 | 27.087 | 2.734 | −47.634 | 1.00 | 26.11 A |
| ATOM | 396 | C | GLY | A | 121 | 26.363 | 3.735 | −46.755 | 1.00 | 25.00 A |
| ATOM | 397 | O | GLY | A | 121 | 26.607 | 4.944 | −46.837 | 1.00 | 22.88 A |
| ATOM | 398 | N | ILE | A | 122 | 25.484 | 3.240 | −45.894 | 1.00 | 23.50 A |
| ATOM | 399 | CA | ILE | A | 122 | 24.730 | 4.131 | −45.032 | 1.00 | 23.79 A |
| ATOM | 400 | CB | ILE | A | 122 | 23.255 | 4.131 | −45.452 | 1.00 | 24.10 A |
| ATOM | 401 | CG2 | ILE | A | 122 | 22.460 | 3.154 | −44.612 | 1.00 | 23.83 A |
| ATOM | 402 | CG1 | ILE | A | 122 | 22.721 | 5.555 | −45.390 | 1.00 | 23.51 A |
| ATOM | 403 | CD1 | ILE | A | 122 | 23.404 | 6.457 | −46.381 | 1.00 | 22.10 A |
| ATOM | 404 | C | ILE | A | 122 | 24.852 | 3.766 | −43.568 | 1.00 | 22.35 A |
| ATOM | 405 | O | ILE | A | 122 | 24.598 | 4.585 | −42.685 | 1.00 | 21.65 A |
| ATOM | 406 | N | GLY | A | 123 | 25.240 | 2.521 | −43.329 | 1.00 | 21.64 A |
| ATOM | 407 | CA | GLY | A | 123 | 25.405 | 2.018 | −41.980 | 1.00 | 20.23 A |
| ATOM | 408 | C | GLY | A | 123 | 26.421 | 0.892 | −41.999 | 1.00 | 20.31 A |
| ATOM | 409 | O | GLY | A | 123 | 26.645 | 0.250 | −43.032 | 1.00 | 21.53 A |
| ATOM | 410 | N | LEU | A | 124 | 27.051 | 0.647 | −40.860 | 1.00 | 19.19 A |
| ATOM | 411 | CA | LEU | A | 124 | 28.049 | −0.405 | −40.784 | 1.00 | 18.26 A |
| ATOM | 412 | CB | LEU | A | 124 | 29.366 | 0.095 | −41.390 | 1.00 | 16.37 A |
| ATOM | 413 | CG | LEU | A | 124 | 30.540 | −0.878 | −41.504 | 1.00 | 18.75 A |
| ATOM | 414 | CD1 | LEU | A | 124 | 30.236 | −1.928 | −42.573 | 1.00 | 20.38 A |
| ATOM | 415 | CD2 | LEU | A | 124 | 31.803 | −0.101 | −41.868 | 1.00 | 17.41 A |
| ATOM | 416 | C | LEU | A | 124 | 28.264 | −0.824 | −39.336 | 1.00 | 17.38 A |
| ATOM | 417 | O | LEU | A | 124 | 28.340 | 0.014 | −38.440 | 1.00 | 17.30 A |
| ATOM | 418 | N | SER | A | 125 | 28.352 | −2.128 | −39.113 | 1.00 | 16.59 A |
| ATOM | 419 | CA | SER | A | 125 | 28.578 | −2.656 | −37.782 | 1.00 | 15.38 A |
| ATOM | 420 | CB | SER | A | 125 | 27.498 | −3.672 | −37.429 | 1.00 | 15.89 A |
| ATOM | 421 | OG | SER | A | 125 | 27.537 | −4.772 | −38.323 | 1.00 | 20.69 A |
| ATOM | 422 | C | SER | A | 125 | 29.949 | −3.324 | −37.790 | 1.00 | 14.95 A |
| ATOM | 423 | O | SER | A | 125 | 30.388 | −3.824 | −38.819 | 1.00 | 13.32 A |
| ATOM | 424 | N | ALA | A | 126 | 30.616 | −3.319 | −36.641 | 1.00 | 13.72 A |
| ATOM | 425 | CA | ALA | A | 126 | 31.942 | −3.903 | −36.498 | 1.00 | 14.24 A |
| ATOM | 426 | CB | ALA | A | 126 | 32.362 | −3.878 | −35.034 | 1.00 | 13.11 A |
| ATOM | 427 | C | ALA | A | 126 | 32.089 | −5.318 | −37.060 | 1.00 | 14.55 A |
| ATOM | 428 | O | ALA | A | 126 | 33.113 | −5.640 | −37.663 | 1.00 | 16.65 A |
| ATOM | 429 | N | PRO | A | 127 | 31.083 | −6.188 | −36.859 | 1.00 | 15.05 A |
| ATOM | 430 | CD | PRO | A | 127 | 29.881 | −6.062 | −36.012 | 1.00 | 13.21 A |
| ATOM | 431 | CA | PRO | A | 127 | 31.205 | −7.549 | −37.395 | 1.00 | 14.59 A |
| ATOM | 432 | CB | PRO | A | 127 | 29.837 | −8.155 | −37.104 | 1.00 | 15.34 A |
| ATOM | 433 | CG | PRO | A | 127 | 29.489 | −7.513 | −35.782 | 1.00 | 14.66 A |
| ATOM | 434 | C | PRO | A | 127 | 31.522 | −7.518 | −38.885 | 1.00 | 15.75 A |
| ATOM | 435 | O | PRO | A | 127 | 32.242 | −8.382 | −39.400 | 1.00 | 12.00 A |
| ATOM | 436 | N | GLN | A | 128 | 30.993 | −6.498 | −39.559 | 1.00 | 15.65 A |
| ATOM | 437 | CA | GLN | A | 128 | 31.191 | −6.323 | −40.993 | 1.00 | 17.40 A |
| ATOM | 438 | CB | GLN | A | 128 | 30.180 | −5.316 | −41.542 | 1.00 | 16.39 A |
| ATOM | 439 | CG | GLN | A | 128 | 28.812 | −5.917 | −41.778 | 1.00 | 18.40 A |
| ATOM | 440 | CD | GLN | A | 128 | 27.801 | −4.891 | −42.228 | 1.00 | 20.84 A |
| ATOM | 441 | OE1 | GLN | A | 128 | 27.428 | −4.002 | −41.458 | 1.00 | 22.13 A |
| ATOM | 442 | NE2 | GLN | A | 128 | 27.350 | −4.999 | −43.482 | 1.00 | 18.66 A |
| ATOM | 443 | C | GLN | A | 128 | 32.603 | −5.912 | −41.396 | 1.00 | 19.05 A |
| ATOM | 444 | O | GLN | A | 128 | 32.919 | −5.860 | −42.584 | 1.00 | 20.10 A |
| ATOM | 445 | N | VAL | A | 129 | 33.448 | −5.608 | −40.418 | 1.00 | 19.63 A |
| ATOM | 446 | CA | VAL | A | 129 | 34.828 | −5.241 | −40.712 | 1.00 | 20.04 A |
| ATOM | 447 | CB | VAL | A | 129 | 35.152 | −3.775 | −40.284 | 1.00 | 20.18 A |
| ATOM | 448 | CG1 | VAL | A | 129 | 34.404 | −2.805 | −41.161 | 1.00 | 18.05 A |

-continued

| | | | | | | | | | | |
|---|---|---|---|---|---|---|---|---|---|---|
| ATOM | 449 | CG2 | VAL | A | 129 | 34.780 | −3.546 | −38.829 | 1.00 | 19.45 A |
| ATOM | 450 | C | VAL | A | 129 | 35.773 | −6.216 | −40.002 | 1.00 | 21.14 A |
| ATOM | 451 | O | VAL | A | 129 | 36.959 | −5.944 | −39.844 | 1.00 | 21.90 A |
| ATOM | 452 | N | GLY | A | 130 | 35.228 | −7.348 | −39.561 | 1.00 | 22.19 A |
| ATOM | 453 | CA | GLY | A | 130 | 36.035 | −8.368 | −38.907 | 1.00 | 20.21 A |
| ATOM | 454 | C | GLY | A | 130 | 36.113 | −8.351 | −37.390 | 1.00 | 19.73 A |
| ATOM | 455 | O | GLY | A | 130 | 36.776 | −9.201 | −36.790 | 1.00 | 18.88 A |
| ATOM | 456 | N | LEU | A | 131 | 35.445 | −7.396 | −36.758 | 1.00 | 17.97 A |
| ATOM | 457 | CA | LEU | A | 131 | 35.488 | −7.307 | −35.305 | 1.00 | 16.71 A |
| ATOM | 458 | CB | LEU | A | 131 | 35.860 | −5.890 | −34.878 | 1.00 | 17.61 A |
| ATOM | 459 | CG | LEU | A | 131 | 37.335 | −5.519 | −35.060 | 1.00 | 19.78 A |
| ATOM | 460 | CD1 | LEU | A | 131 | 37.765 | −5.704 | −36.509 | 1.00 | 21.35 A |
| ATOM | 461 | CD2 | LEU | A | 131 | 37.539 | −4.091 | −34.629 | 1.00 | 17.99 A |
| ATOM | 462 | C | LEU | A | 131 | 34.175 | −7.717 | −34.662 | 1.00 | 16.20 A |
| ATOM | 463 | O | LEU | A | 131 | 33.110 | −7.171 | −34.979 | 1.00 | 16.20 A |
| ATOM | 464 | N | ASN | A | 132 | 34.249 | −8.687 | −33.758 | 1.00 | 15.11 A |
| ATOM | 465 | CA | ASN | A | 132 | 33.049 | −9.158 | −33.092 | 1.00 | 14.07 A |
| ATOM | 466 | CB | ASN | A | 132 | 33.109 | −10.675 | −32.904 | 1.00 | 14.53 A |
| ATOM | 467 | CG | ASN | A | 132 | 32.921 | −11.420 | −34.221 | 1.00 | 15.08 A |
| ATOM | 468 | OD1 | ASN | A | 132 | 33.885 | −11.786 | −34.882 | 1.00 | 17.92 A |
| ATOM | 469 | ND2 | ASN | A | 132 | 31.673 | −11.611 | −34.617 | 1.00 | 13.68 A |
| ATOM | 470 | C | ASN | A | 132 | 32.768 | −8.444 | −31.780 | 1.00 | 13.50 A |
| ATOM | 471 | O | ASN | A | 132 | 32.749 | −9.050 | −30.708 | 1.00 | 13.65 A |
| ATOM | 472 | N | VAL | A | 133 | 32.549 | −7.138 | −31.890 | 1.00 | 12.59 A |
| ATOM | 473 | CA | VAL | A | 133 | 32.242 | −6.307 | −30.741 | 1.00 | 13.93 A |
| ATOM | 474 | CB | VAL | A | 133 | 33.409 | −5.347 | −30.416 | 1.00 | 10.85 A |
| ATOM | 475 | CG1 | VAL | A | 133 | 34.607 | −6.149 | −29.931 | 1.00 | 10.23 A |
| ATOM | 476 | CG2 | VAL | A | 133 | 33.784 | −4.544 | −31.638 | 1.00 | 10.25 A |
| ATOM | 477 | C | VAL | A | 133 | 30.971 | −5.513 | −31.018 | 1.00 | 13.57 A |
| ATOM | 478 | O | VAL | A | 133 | 30.563 | −5.364 | −32.162 | 1.00 | 13.60 A |
| ATOM | 479 | N | GLN | A | 134 | 30.353 | −5.002 | −29.963 | 1.00 | 15.90 A |
| ATOM | 480 | CA | GLN | A | 134 | 29.111 | −4.246 | −30.100 | 1.00 | 17.13 A |
| ATOM | 481 | CB | GLN | A | 134 | 28.276 | −4.439 | −28.831 | 1.00 | 15.99 A |
| ATOM | 482 | CG | GLN | A | 134 | 27.851 | −5.906 | −28.679 | 1.00 | 17.43 A |
| ATOM | 483 | CD | GLN | A | 134 | 27.161 | −6.217 | −27.368 | 1.00 | 19.77 A |
| ATOM | 484 | OE1 | GLN | A | 134 | 26.439 | −5.386 | −26.822 | 1.00 | 23.84 A |
| ATOM | 485 | NE2 | GLN | A | 134 | 27.359 | −7.433 | −26.866 | 1.00 | 18.29 A |
| ATOM | 486 | C | GLN | A | 134 | 29.324 | −2.771 | −30.423 | 1.00 | 16.76 A |
| ATOM | 487 | O | GLN | A | 134 | 29.182 | −1.900 | −29.566 | 1.00 | 16.52 A |
| ATOM | 488 | N | LEU | A | 135 | 29.672 | −2.515 | −31.682 | 1.00 | 15.24 A |
| ATOM | 489 | CA | LEU | A | 135 | 29.928 | −1.162 | −32.172 | 1.00 | 15.82 A |
| ATOM | 490 | CB | LEU | A | 135 | 31.436 | −0.933 | −32.344 | 1.00 | 14.00 A |
| ATOM | 491 | CG | LEU | A | 135 | 31.828 | 0.460 | −32.840 | 1.00 | 15.40 A |
| ATOM | 492 | CD1 | LEU | A | 135 | 31.450 | 1.490 | −31.775 | 1.00 | 14.23 A |
| ATOM | 493 | CD2 | LEU | A | 135 | 33.322 | 0.508 | −33.163 | 1.00 | 12.52 A |
| ATOM | 494 | C | LEU | A | 135 | 29.218 | −0.931 | −33.502 | 1.00 | 14.99 A |
| ATOM | 495 | O | LEU | A | 135 | 29.251 | −1.773 | −34.400 | 1.00 | 15.49 A |
| ATOM | 496 | N | MET | A | 136 | 28.608 | 0.235 | −33.638 | 1.00 | 16.04 A |
| ATOM | 497 | CA | MET | A | 136 | 27.859 | 0.561 | −34.841 | 1.00 | 18.35 A |
| ATOM | 498 | CB | MET | A | 136 | 26.396 | 0.180 | −34.588 | 1.00 | 19.43 A |
| ATOM | 499 | CG | MET | A | 136 | 25.375 | 0.880 | −35.438 | 1.00 | 23.19 A |
| ATOM | 500 | SD | MET | A | 136 | 23.777 | 0.872 | −34.619 | 1.00 | 26.18 A |
| ATOM | 501 | CE | MET | A | 136 | 23.640 | −0.872 | −34.190 | 1.00 | 22.49 A |
| ATOM | 502 | C | MET | A | 136 | 27.967 | 2.039 | −35.255 | 1.00 | 19.14 A |
| ATOM | 503 | O | MET | A | 136 | 28.119 | 2.934 | −34.408 | 1.00 | 18.03 A |
| ATOM | 504 | N | VAL | A | 137 | 27.904 | 2.284 | −36.563 | 1.00 | 18.64 A |
| ATOM | 505 | CA | VAL | A | 137 | 27.941 | 3.643 | −37.094 | 1.00 | 19.57 A |
| ATOM | 506 | CB | VAL | A | 137 | 29.354 | 4.075 | −37.558 | 1.00 | 21.08 A |
| ATOM | 507 | CG1 | VAL | A | 137 | 30.374 | 3.826 | −36.451 | 1.00 | 20.89 A |
| ATOM | 508 | CG2 | VAL | A | 137 | 29.723 | 3.356 | −38.854 | 1.00 | 20.49 A |
| ATOM | 509 | C | VAL | A | 137 | 27.018 | 3.757 | −38.301 | 1.00 | 20.02 A |
| ATOM | 510 | O | VAL | A | 137 | 26.667 | 2.754 | −38.933 | 1.00 | 18.78 A |
| ATOM | 511 | N | PHE | A | 138 | 26.621 | 4.985 | −38.614 | 1.00 | 20.79 A |
| ATOM | 512 | CA | PHE | A | 138 | 25.771 | 5.225 | −39.762 | 1.00 | 22.08 A |
| ATOM | 513 | CB | PHE | A | 138 | 24.451 | 4.446 | −39.629 | 1.00 | 23.84 A |
| ATOM | 514 | CG | PHE | A | 138 | 23.535 | 4.947 | −38.549 | 1.00 | 22.93 A |
| ATOM | 515 | CD1 | PHE | A | 138 | 22.588 | 5.926 | −38.822 | 1.00 | 25.45 A |
| ATOM | 516 | CD2 | PHE | A | 138 | 23.584 | 4.405 | −37.268 | 1.00 | 25.82 A |
| ATOM | 517 | CE1 | PHE | A | 138 | 21.692 | 6.357 | −37.832 | 1.00 | 24.76 A |
| ATOM | 518 | CE2 | PHE | A | 138 | 22.697 | 4.829 | −36.271 | 1.00 | 25.19 A |
| ATOM | 519 | CZ | PHE | A | 138 | 21.748 | 5.807 | −36.558 | 1.00 | 24.73 A |
| ATOM | 520 | C | PHE | A | 138 | 25.511 | 6.705 | −39.982 | 1.00 | 23.31 A |
| ATOM | 521 | O | PHE | A | 138 | 25.671 | 7.530 | −39.071 | 1.00 | 21.01 A |
| ATOM | 522 | N | ASN | A | 139 | 25.137 | 7.026 | −41.216 | 1.00 | 24.83 A |
| ATOM | 523 | CA | ASN | A | 139 | 24.838 | 8.388 | −41.622 | 1.00 | 26.78 A |
| ATOM | 524 | CB | ASN | A | 139 | 26.104 | 9.080 | −42.113 | 1.00 | 28.84 A |
| ATOM | 525 | CG | ASN | A | 139 | 25.919 | 10.574 | −42.268 | 1.00 | 31.35 A |
| ATOM | 526 | OD1 | ASN | A | 139 | 24.951 | 11.031 | −42.876 | 1.00 | 29.99 A |
| ATOM | 527 | ND2 | ASN | A | 139 | 26.850 | 11.346 | −41.717 | 1.00 | 31.87 A |

-continued

| | | | | | | | | | | |
|---|---|---|---|---|---|---|---|---|---|---|
| ATOM | 528 | C | ASN | A | 139 | 23.826 | 8.305 | −42.762 | 1.00 | 27.67 A |
| ATOM | 529 | O | ASN | A | 139 | 24.147 | 7.834 | −43.850 | 1.00 | 26.38 A |
| ATOM | 530 | N | PRO | A | 140 | 22.587 | 8.762 | −42.522 | 1.00 | 28.57 A |
| ATOM | 531 | CD | PRO | A | 140 | 22.108 | 9.409 | −41.288 | 1.00 | 27.09 A |
| ATOM | 532 | CA | PRO | A | 140 | 21.525 | 8.733 | −43.531 | 1.00 | 29.40 A |
| ATOM | 533 | CB | PRO | A | 140 | 20.451 | 9.626 | −42.923 | 1.00 | 27.26 A |
| ATOM | 534 | CG | PRO | A | 140 | 20.606 | 9.366 | −41.472 | 1.00 | 28.54 A |
| ATOM | 535 | C | PRO | A | 140 | 21.976 | 9.231 | −44.892 | 1.00 | 29.84 A |
| ATOM | 536 | O | PRO | A | 140 | 21.655 | 8.635 | −45.914 | 1.00 | 30.11 A |
| ATOM | 537 | N | ALA | A | 141 | 22.716 | 10.332 | −44.897 | 1.00 | 31.08 A |
| ATOM | 538 | CA | ALA | A | 141 | 23.200 | 10.921 | −46.138 | 1.00 | 33.10 A |
| ATOM | 539 | CB | ALA | A | 141 | 23.945 | 12.207 | −45.838 | 1.00 | 32.04 A |
| ATOM | 540 | C | ALA | A | 141 | 24.095 | 9.969 | −46.928 | 1.00 | 34.75 A |
| ATOM | 541 | O | ALA | A | 141 | 23.899 | 9.777 | −48.129 | 1.00 | 34.87 A |
| ATOM | 542 | N | GLY | A | 142 | 25.079 | 9.380 | −46.253 | 1.00 | 36.61 A |
| ATOM | 543 | CA | GLY | A | 142 | 25.989 | 8.461 | −46.916 | 1.00 | 38.38 A |
| ATOM | 544 | C | GLY | A | 142 | 27.181 | 9.178 | −47.519 | 1.00 | 39.97 A |
| ATOM | 545 | O | GLY | A | 142 | 28.022 | 8.559 | −48.175 | 1.00 | 40.45 A |
| ATOM | 546 | N | GLU | A | 143 | 27.248 | 10.487 | −47.293 | 1.00 | 41.61 A |
| ATOM | 547 | CA | GLU | A | 143 | 28.327 | 11.321 | −47.808 | 1.00 | 43.02 A |
| ATOM | 548 | CB | GLU | A | 143 | 27.765 | 12.402 | −48.737 | 1.00 | 44.16 A |
| ATOM | 549 | CG | GLU | A | 143 | 26.697 | 11.917 | −49.707 | 1.00 | 47.41 A |
| ATOM | 550 | CD | GLU | A | 143 | 27.262 | 11.131 | −50.874 | 1.00 | 49.37 A |
| ATOM | 551 | OE1 | GLU | A | 143 | 28.046 | 10.183 | −50.645 | 1.00 | 50.56 A |
| ATOM | 552 | OE2 | GLU | A | 143 | 26.914 | 11.463 | −52.027 | 1.00 | 51.60 A |
| ATOM | 553 | C | GLU | A | 143 | 29.014 | 12.000 | −46.630 | 1.00 | 43.65 A |
| ATOM | 554 | O | GLU | A | 143 | 28.353 | 12.483 | −45.710 | 1.00 | 42.94 A |
| ATOM | 555 | N | PRO | A | 144 | 30.351 | 12.046 | −46.639 | 1.00 | 44.50 A |
| ATOM | 556 | CD | PRO | A | 144 | 31.298 | 11.494 | −47.620 | 1.00 | 44.64 A |
| ATOM | 557 | CA | PRO | A | 144 | 31.062 | 12.690 | −45.535 | 1.00 | 45.86 A |
| ATOM | 558 | CB | PRO | A | 144 | 32.525 | 12.567 | −45.947 | 1.00 | 44.41 A |
| ATOM | 559 | CG | PRO | A | 144 | 32.539 | 11.336 | −46.788 | 1.00 | 44.69 A |
| ATOM | 560 | C | PRO | A | 144 | 30.624 | 14.146 | −45.431 | 1.00 | 47.73 A |
| ATOM | 561 | O | PRO | A | 144 | 30.269 | 14.765 | −46.437 | 1.00 | 49.56 A |
| ATOM | 562 | N | GLY | A | 145 | 30.639 | 14.684 | −44.216 | 1.00 | 48.72 A |
| ATOM | 563 | CA | GLY | A | 145 | 30.260 | 16.070 | −44.010 | 1.00 | 50.25 A |
| ATOM | 564 | C | GLY | A | 145 | 29.010 | 16.538 | −44.735 | 1.00 | 51.98 A |
| ATOM | 565 | O | GLY | A | 145 | 28.889 | 17.719 | −45.063 | 1.00 | 51.37 A |
| ATOM | 566 | N | GLU | A | 146 | 28.074 | 15.625 | −44.986 | 1.00 | 53.56 A |
| ATOM | 567 | CA | GLU | A | 146 | 26.834 | 15.989 | −45.664 | 1.00 | 54.37 A |
| ATOM | 568 | CB | GLU | A | 146 | 26.947 | 15.734 | −47.175 | 1.00 | 56.97 A |
| ATOM | 569 | CG | GLU | A | 146 | 25.797 | 16.333 | −47.990 | 1.00 | 61.12 A |
| ATOM | 570 | CD | GLU | A | 146 | 25.915 | 16.063 | −49.483 | 1.00 | 64.36 A |
| ATOM | 571 | OE1 | GLU | A | 146 | 25.957 | 14.876 | −49.877 | 1.00 | 65.64 A |
| ATOM | 572 | OE2 | GLU | A | 146 | 25.961 | 17.040 | −50.263 | 1.00 | 66.22 A |
| ATOM | 573 | C | GLU | A | 146 | 25.640 | 15.224 | −45.099 | 1.00 | 52.66 A |
| ATOM | 574 | O | GLU | A | 146 | 24.731 | 14.850 | −45.833 | 1.00 | 53.40 A |
| ATOM | 575 | N | GLY | A | 147 | 25.646 | 14.994 | −43.790 | 1.00 | 51.08 A |
| ATOM | 576 | CA | GLY | A | 147 | 24.546 | 14.281 | −43.167 | 1.00 | 48.20 A |
| ATOM | 577 | C | GLY | A | 147 | 24.567 | 14.368 | −41.652 | 1.00 | 46.60 A |
| ATOM | 578 | O | GLY | A | 147 | 24.767 | 15.442 | −41.080 | 1.00 | 46.48 A |
| ATOM | 579 | N | LYS | A | 148 | 24.361 | 13.230 | −40.997 | 1.00 | 44.44 A |
| ATOM | 580 | CA | LYS | A | 148 | 24.353 | 13.171 | −39.541 | 1.00 | 42.17 A |
| ATOM | 581 | CB | LYS | A | 148 | 22.908 | 13.167 | −39.032 | 1.00 | 44.06 A |
| ATOM | 582 | CG | LYS | A | 148 | 22.653 | 13.989 | −37.773 | 1.00 | 44.66 A |
| ATOM | 583 | CD | LYS | A | 148 | 23.184 | 13.323 | −36.515 | 1.00 | 46.34 A |
| ATOM | 584 | CE | LYS | A | 148 | 22.674 | 14.052 | −35.271 | 1.00 | 47.35 A |
| ATOM | 585 | NZ | LYS | A | 148 | 23.051 | 13.382 | −33.995 | 1.00 | 48.38 A |
| ATOM | 586 | C | LYS | A | 148 | 25.064 | 11.889 | −39.126 | 1.00 | 40.11 A |
| ATOM | 587 | O | LYS | A | 148 | 24.509 | 10.799 | −39.251 | 1.00 | 39.43 A |
| ATOM | 588 | N | GLU | A | 149 | 26.297 | 12.020 | −38.646 | 1.00 | 37.37 A |
| ATOM | 589 | CA | GLU | A | 149 | 27.062 | 10.853 | −38.227 | 1.00 | 35.24 A |
| ATOM | 590 | CB | GLU | A | 149 | 28.559 | 11.133 | −38.288 | 1.00 | 33.46 A |
| ATOM | 591 | CG | GLU | A | 149 | 29.049 | 11.512 | −39.662 | 1.00 | 33.59 A |
| ATOM | 592 | CD | GLU | A | 149 | 30.535 | 11.306 | −39.810 | 1.00 | 32.30 A |
| ATOM | 593 | OE1 | GLU | A | 149 | 31.252 | 11.517 | −38.809 | 1.00 | 29.90 A |
| ATOM | 594 | OE2 | GLU | A | 149 | 30.982 | 10.943 | −40.923 | 1.00 | 31.18 A |
| ATOM | 595 | C | GLU | A | 149 | 26.692 | 10.414 | −36.823 | 1.00 | 33.65 A |
| ATOM | 596 | O | GLU | A | 149 | 26.843 | 11.169 | −35.863 | 1.00 | 33.30 A |
| ATOM | 597 | N | ILE | A | 150 | 26.210 | 9.180 | −36.715 | 1.00 | 31.34 A |
| ATOM | 598 | CA | ILE | A | 150 | 25.808 | 8.622 | −35.434 | 1.00 | 28.27 A |
| ATOM | 599 | CB | ILE | A | 150 | 24.303 | 8.325 | −35.411 | 1.00 | 28.74 A |
| ATOM | 600 | CG2 | ILE | A | 150 | 23.948 | 7.564 | −34.138 | 1.00 | 27.91 A |
| ATOM | 601 | CG1 | ILE | A | 150 | 23.518 | 9.634 | −35.538 | 1.00 | 29.27 A |
| ATOM | 602 | CD1 | ILE | A | 150 | 22.030 | 9.449 | −35.777 | 1.00 | 31.15 A |
| ATOM | 603 | C | ILE | A | 150 | 26.541 | 7.326 | −35.156 | 1.00 | 26.22 A |
| ATOM | 604 | O | ILE | A | 150 | 26.504 | 6.400 | −35.965 | 1.00 | 27.50 A |
| ATOM | 605 | N | VAL | A | 151 | 27.218 | 7.265 | −34.017 | 1.00 | 22.94 A |
| ATOM | 606 | CA | VAL | A | 151 | 27.931 | 6.057 | −33.629 | 1.00 | 21.78 A |

-continued

| | | | | | | | | | |
|---|---|---|---|---|---|---|---|---|---|
| ATOM | 607 | CB | VAL | A | 151 | 29.468 | 6.322 | −33.492 | 1.00 21.52 A |
| ATOM | 608 | CG1 | VAL | A | 151 | 29.748 | 7.803 | −33.617 | 1.00 20.75 A |
| ATOM | 609 | CG2 | VAL | A | 151 | 30.001 | 5.774 | −32.182 | 1.00 19.13 A |
| ATOM | 610 | C | VAL | A | 151 | 27.319 | 5.577 | −32.316 | 1.00 20.78 A |
| ATOM | 611 | O | VAL | A | 151 | 26.936 | 6.390 | −31.473 | 1.00 22.39 A |
| ATOM | 612 | N | LEU | A | 152 | 27.196 | 4.264 | −32.152 | 1.00 19.13 A |
| ATOM | 613 | CA | LEU | A | 152 | 26.600 | 3.716 | −30.938 | 1.00 19.50 A |
| ATOM | 614 | CB | LEU | A | 152 | 25.161 | 3.260 | −31.223 | 1.00 19.10 A |
| ATOM | 615 | CG | LEU | A | 152 | 24.193 | 4.305 | −31.798 | 1.00 24.16 A |
| ATOM | 616 | CD1 | LEU | A | 152 | 23.081 | 3.618 | −32.569 | 1.00 24.32 A |
| ATOM | 617 | CD2 | LEU | A | 152 | 23.618 | 5.156 | −30.677 | 1.00 24.79 A |
| ATOM | 618 | C | LEU | A | 152 | 27.392 | 2.545 | −30.353 | 1.00 17.69 A |
| ATOM | 619 | O | LEU | A | 152 | 27.678 | 1.571 | −31.049 | 1.00 16.33 A |
| ATOM | 620 | N | VAL | A | 153 | 27.742 | 2.641 | −29.073 | 1.00 15.12 A |
| ATOM | 621 | CA | VAL | A | 153 | 28.466 | 1.563 | −28.409 | 1.00 14.13 A |
| ATOM | 622 | CB | VAL | A | 153 | 29.672 | 2.096 | −27.611 | 1.00 13.29 A |
| ATOM | 623 | CG1 | VAL | A | 153 | 30.442 | 0.939 | −26.997 | 1.00 12.78 A |
| ATOM | 624 | CG2 | VAL | A | 153 | 30.578 | 2.901 | −28.514 | 1.00 14.26 A |
| ATOM | 625 | C | VAL | A | 153 | 27.498 | 0.843 | −27.457 | 1.00 15.36 A |
| ATOM | 626 | O | VAL | A | 153 | 26.748 | 1.491 | −26.719 | 1.00 12.91 A |
| ATOM | 627 | N | ASN | A | 154 | 27.530 | −0.492 | −27.480 | 1.00 15.63 A |
| ATOM | 628 | CA | ASN | A | 154 | 26.653 | −1.334 | −26.658 | 1.00 16.94 A |
| ATOM | 629 | CB | ASN | A | 154 | 27.180 | −1.448 | −25.225 | 1.00 15.99 A |
| ATOM | 630 | CG | ASN | A | 154 | 28.646 | −1.828 | −25.171 | 1.00 17.69 A |
| ATOM | 631 | OD1 | ASN | A | 154 | 29.097 | −2.698 | −25.915 | 1.00 17.61 A |
| ATOM | 632 | ND2 | ASN | A | 154 | 29.398 | −1.182 | −24.282 | 1.00 15.37 A |
| ATOM | 633 | C | ASN | A | 154 | 25.216 | −0.801 | −26.632 | 1.00 17.66 A |
| ATOM | 634 | O | ASN | A | 154 | 24.666 | −0.510 | −25.571 | 1.00 17.48 A |
| ATOM | 635 | N | PRO | A | 155 | 24.588 | −0.677 | −27.814 | 1.00 18.56 A |
| ATOM | 636 | CD | PRO | A | 155 | 25.183 | −0.907 | −29.138 | 1.00 18.26 A |
| ATOM | 637 | CA | PRO | A | 155 | 23.215 | −0.181 | −27.950 | 1.00 18.44 A |
| ATOM | 638 | CB | PRO | A | 155 | 23.056 | 0.004 | −29.459 | 1.00 17.65 A |
| ATOM | 639 | CG | PRO | A | 155 | 24.458 | 0.102 | −29.966 | 1.00 19.09 A |
| ATOM | 640 | C | PRO | A | 155 | 22.173 | −1.157 | −27.412 | 1.00 18.75 A |
| ATOM | 641 | O | PRO | A | 155 | 22.277 | −2.365 | −27.606 | 1.00 19.82 A |
| ATOM | 642 | N | LYS | A | 156 | 21.162 | −0.622 | −26.745 | 1.00 20.00 A |
| ATOM | 643 | CA | LYS | A | 156 | 20.082 | −1.441 | −26.221 | 1.00 20.87 A |
| ATOM | 644 | CB | LYS | A | 156 | 20.150 | −1.499 | −24.701 | 1.00 21.41 A |
| ATOM | 645 | CG | LYS | A | 156 | 21.482 | −1.949 | −24.167 | 1.00 26.83 A |
| ATOM | 646 | CD | LYS | A | 156 | 21.488 | −1.995 | −22.637 | 1.00 30.30 A |
| ATOM | 647 | CE | LYS | A | 156 | 21.449 | −0.601 | −22.030 | 1.00 34.64 A |
| ATOM | 648 | NZ | LYS | A | 156 | 21.678 | −0.636 | −20.551 | 1.00 36.85 A |
| ATOM | 649 | C | LYS | A | 156 | 18.751 | −0.824 | −26.653 | 1.00 21.39 A |
| ATOM | 650 | O | LYS | A | 156 | 18.532 | 0.388 | −26.514 | 1.00 19.74 A |
| ATOM | 651 | N | ILE | A | 157 | 17.869 | −1.649 | −27.198 | 1.00 22.00 A |
| ATOM | 652 | CA | ILE | A | 157 | 16.571 | −1.148 | −27.616 | 1.00 24.95 A |
| ATOM | 653 | CB | ILE | A | 157 | 15.983 | −1.978 | −28.781 | 1.00 24.61 A |
| ATOM | 654 | CG2 | ILE | A | 157 | 14.540 | −1.559 | −29.045 | 1.00 24.26 A |
| ATOM | 655 | CG1 | ILE | A | 157 | 16.834 | −1.779 | −30.038 | 1.00 24.91 A |
| ATOM | 656 | CD1 | ILE | A | 157 | 16.258 | −2.433 | −31.290 | 1.00 25.22 A |
| ATOM | 657 | C | ILE | A | 157 | 15.634 | −1.204 | −26.422 | 1.00 26.62 A |
| ATOM | 658 | O | ILE | A | 157 | 15.236 | −2.284 | −25.988 | 1.00 25.35 A |
| ATOM | 659 | N | LYS | A | 158 | 15.306 | −0.035 | −25.879 | 1.00 30.00 A |
| ATOM | 660 | CA | LYS | A | 158 | 14.411 | 0.052 | −24.732 | 1.00 32.44 A |
| ATOM | 661 | CB | LYS | A | 158 | 14.584 | 1.393 | −24.009 | 1.00 34.21 A |
| ATOM | 662 | CG | LYS | A | 158 | 15.822 | 1.460 | −23.114 | 1.00 36.80 A |
| ATOM | 663 | CD | LYS | A | 158 | 15.721 | 0.464 | −21.965 | 1.00 37.85 A |
| ATOM | 664 | CE | LYS | A | 158 | 17.089 | 0.107 | −21.389 | 1.00 40.17 A |
| ATOM | 665 | NZ | LYS | A | 158 | 17.827 | 1.271 | −20.817 | 1.00 40.51 A |
| ATOM | 666 | C | LYS | A | 158 | 12.969 | −0.119 | −25.170 | 1.00 32.94 A |
| ATOM | 667 | O | LYS | A | 158 | 12.183 | −0.765 | −24.486 | 1.00 34.80 A |
| ATOM | 668 | N | LYS | A | 159 | 12.623 | 0.456 | −26.314 | 1.00 33.25 A |
| ATOM | 669 | CA | LYS | A | 159 | 11.269 | 0.349 | −26.834 | 1.00 34.87 A |
| ATOM | 670 | CB | LYS | A | 159 | 10.367 | 1.438 | −26.235 | 1.00 37.06 A |
| ATOM | 671 | CG | LYS | A | 159 | 10.126 | 1.305 | −24.736 | 1.00 40.70 A |
| ATOM | 672 | CD | LYS | A | 159 | 9.057 | 2.265 | −24.239 | 1.00 42.38 A |
| ATOM | 673 | CE | LYS | A | 159 | 8.687 | 1.963 | −22.787 | 1.00 44.63 A |
| ATOM | 674 | NZ | LYS | A | 159 | 7.473 | 2.710 | −22.322 | 1.00 46.12 A |
| ATOM | 675 | C | LYS | A | 159 | 11.269 | 0.495 | −28.340 | 1.00 34.89 A |
| ATOM | 676 | O | LYS | A | 159 | 12.135 | 1.161 | −28.903 | 1.00 35.59 A |
| ATOM | 677 | N | TYR | A | 160 | 10.311 | −0.147 | −28.996 | 1.00 35.44 A |
| ATOM | 678 | CA | TYR | A | 160 | 10.187 | −0.025 | −30.439 | 1.00 36.62 A |
| ATOM | 679 | CB | TYR | A | 160 | 10.842 | −1.208 | −31.162 | 1.00 42.19 A |
| ATOM | 680 | CG | TYR | A | 160 | 10.445 | −2.569 | −30.673 | 1.00 47.11 A |
| ATOM | 681 | CD1 | TYR | A | 160 | 9.143 | −3.037 | −30.838 | 1.00 50.34 A |
| ATOM | 682 | CE1 | TYR | A | 160 | 8.776 | −4.314 | −30.407 | 1.00 53.27 A |
| ATOM | 683 | CD2 | TYR | A | 160 | 11.381 | −3.405 | −30.062 | 1.00 49.07 A |
| ATOM | 684 | CE2 | TYR | A | 160 | 11.030 | −4.677 | −29.626 | 1.00 52.79 A |
| ATOM | 685 | CZ | TYR | A | 160 | 9.723 | −5.129 | −29.802 | 1.00 54.17 A |

-continued

| | | | | | | | | | | |
|---|---|---|---|---|---|---|---|---|---|---|
| ATOM | 686 | OH | TYR | A | 160 | 9.363 | −6.395 | −29.381 | 1.00 | 56.97 A |
| ATOM | 687 | C | TYR | A | 160 | 8.718 | 0.129 | −30.812 | 1.00 | 33.35 A |
| ATOM | 688 | O | TYR | A | 160 | 7.833 | −0.296 | −30.077 | 1.00 | 33.80 A |
| ATOM | 689 | N | SER | A | 161 | 8.469 | 0.770 | −31.945 | 1.00 | 28.83 A |
| ATOM | 690 | CA | SER | A | 161 | 7.117 | 1.037 | −32.406 | 1.00 | 25.47 A |
| ATOM | 691 | CB | SER | A | 161 | 7.175 | 1.761 | −33.756 | 1.00 | 25.05 A |
| ATOM | 692 | OG | SER | A | 161 | 5.877 | 2.039 | −34.248 | 1.00 | 25.20 A |
| ATOM | 693 | C | SER | A | 161 | 6.227 | −0.194 | −32.525 | 1.00 | 24.00 A |
| ATOM | 694 | O | SER | A | 161 | 6.699 | −1.310 | −32.736 | 1.00 | 25.13 A |
| ATOM | 695 | N | ASP | A | 162 | 4.927 | 0.016 | −32.377 | 1.00 | 20.81 A |
| ATOM | 696 | CA | ASP | A | 162 | 3.988 | −1.078 | −32.512 | 1.00 | 18.67 A |
| ATOM | 697 | CB | ASP | A | 162 | 2.924 | −1.012 | −31.404 | 1.00 | 17.74 A |
| ATOM | 698 | CG | ASP | A | 162 | 2.043 | 0.224 | −31.491 | 1.00 | 20.48 A |
| ATOM | 699 | OD1 | ASP | A | 162 | 2.411 | 1.197 | −32.193 | 1.00 | 19.28 A |
| ATOM | 700 | OD2 | ASP | A | 162 | 0.974 | 0.216 | −30.832 | 1.00 | 20.44 A |
| ATOM | 701 | C | ASP | A | 162 | 3.361 | −1.031 | −33.917 | 1.00 | 17.19 A |
| ATOM | 702 | O | ASP | A | 162 | 2.405 | −1.748 | −34.214 | 1.00 | 16.88 A |
| ATOM | 703 | N | LYS | A | 163 | 3.922 | −0.185 | −34.778 | 1.00 | 13.19 A |
| ATOM | 704 | CA | LYS | A | 163 | 3.458 | −0.060 | −36.157 | 1.00 | 14.42 A |
| ATOM | 705 | CB | LYS | A | 163 | 3.063 | 1.392 | −36.465 | 1.00 | 17.11 A |
| ATOM | 706 | CG | LYS | A | 163 | 2.008 | 1.943 | −35.516 | 1.00 | 21.55 A |
| ATOM | 707 | CD | LYS | A | 163 | 1.511 | 3.321 | −35.933 | 1.00 | 25.69 A |
| ATOM | 708 | CE | LYS | A | 163 | 0.470 | 3.836 | −34.942 | 1.00 | 26.67 A |
| ATOM | 709 | NZ | LYS | A | 163 | −0.163 | 5.115 | −35.373 | 1.00 | 30.99 A |
| ATOM | 710 | C | LYS | A | 163 | 4.563 | −0.515 | −37.114 | 1.00 | 14.12 A |
| ATOM | 711 | O | LYS | A | 163 | 5.709 | −0.067 | −37.029 | 1.00 | 11.38 A |
| ATOM | 712 | N | LEU | A | 164 | 4.207 | −1.405 | −38.032 | 1.00 | 14.88 A |
| ATOM | 713 | CA | LEU | A | 164 | 5.167 | −1.934 | −38.987 | 1.00 | 15.75 A |
| ATOM | 714 | CB | LEU | A | 164 | 4.933 | −3.430 | −39.182 | 1.00 | 16.05 A |
| ATOM | 715 | CG | LEU | A | 164 | 5.202 | −4.299 | −37.953 | 1.00 | 17.46 A |
| ATOM | 716 | CD1 | LEU | A | 164 | 4.720 | −5.716 | −38.219 | 1.00 | 15.64 A |
| ATOM | 717 | CD2 | LEU | A | 164 | 6.696 | −4.269 | −37.617 | 1.00 | 16.61 A |
| ATOM | 718 | C | LEU | A | 164 | 5.153 | −1.251 | −40.340 | 1.00 | 17.09 A |
| ATOM | 719 | O | LEU | A | 164 | 4.097 | −0.893 | −40.865 | 1.00 | 17.75 A |
| ATOM | 720 | N | VAL | A | 165 | 6.343 | −1.066 | −40.900 | 1.00 | 17.38 A |
| ATOM | 721 | CA | VAL | A | 165 | 6.466 | −0.457 | −42.209 | 1.00 | 18.26 A |
| ATOM | 722 | CB | VAL | A | 165 | 6.899 | 1.017 | −42.118 | 1.00 | 16.51 A |
| ATOM | 723 | CG1 | VAL | A | 165 | 5.763 | 1.841 | −41.511 | 1.00 | 16.42 A |
| ATOM | 724 | CG2 | VAL | A | 165 | 8.172 | 1.145 | −41.290 | 1.00 | 17.21 A |
| ATOM | 725 | C | VAL | A | 165 | 7.469 | −1.243 | −43.045 | 1.00 | 19.14 A |
| ATOM | 726 | O | VAL | A | 165 | 8.433 | −1.808 | −42.518 | 1.00 | 20.01 A |
| ATOM | 727 | N | PRO | A | 166 | 7.234 | −1.316 | −44.362 | 1.00 | 19.02 A |
| ATOM | 728 | CD | PRO | A | 166 | 5.982 | −0.965 | −45.062 | 1.00 | 18.32 A |
| ATOM | 729 | CA | PRO | A | 166 | 8.137 | −2.047 | −45.251 | 1.00 | 20.65 A |
| ATOM | 730 | CB | PRO | A | 166 | 7.195 | −2.543 | −46.340 | 1.00 | 20.89 A |
| ATOM | 731 | CG | PRO | A | 166 | 6.284 | −1.350 | −46.503 | 1.00 | 19.48 A |
| ATOM | 732 | C | PRO | A | 166 | 9.222 | −1.132 | −45.805 | 1.00 | 21.42 A |
| ATOM | 733 | O | PRO | A | 166 | 9.073 | 0.087 | −45.803 | 1.00 | 21.01 A |
| ATOM | 734 | N | PHE | A | 167 | 10.312 | −1.728 | −46.275 | 1.00 | 23.28 A |
| ATOM | 735 | CA | PHE | A | 167 | 11.405 | −0.966 | −46.859 | 1.00 | 25.18 A |
| ATOM | 736 | CB | PHE | A | 167 | 12.141 | −0.176 | −45.779 | 1.00 | 28.27 A |
| ATOM | 737 | CG | PHE | A | 167 | 13.095 | 0.840 | −46.325 | 1.00 | 33.26 A |
| ATOM | 738 | CD1 | PHE | A | 167 | 12.637 | 2.083 | −46.751 | 1.00 | 35.31 A |
| ATOM | 739 | CD2 | PHE | A | 167 | 14.450 | 0.540 | −46.459 | 1.00 | 36.84 A |
| ATOM | 740 | CE1 | PHE | A | 167 | 13.514 | 3.022 | −47.308 | 1.00 | 37.46 A |
| ATOM | 741 | CE2 | PHE | A | 167 | 15.341 | 1.468 | −47.014 | 1.00 | 38.88 A |
| ATOM | 742 | CZ | PHE | A | 167 | 14.870 | 2.714 | −47.440 | 1.00 | 38.07 A |
| ATOM | 743 | C | PHE | A | 167 | 12.375 | −1.919 | −47.547 | 1.00 | 24.62 A |
| ATOM | 744 | O | PHE | A | 167 | 12.677 | −2.981 | −47.010 | 1.00 | 24.38 A |
| ATOM | 745 | N | ASP | A | 168 | 12.837 | −1.562 | −48.745 | 1.00 | 25.04 A |
| ATOM | 746 | CA | ASP | A | 168 | 13.791 | −2.414 | −49.456 | 1.00 | 25.00 A |
| ATOM | 747 | CB | ASP | A | 168 | 13.804 | −2.116 | −50.958 | 1.00 | 27.03 A |
| ATOM | 748 | CG | ASP | A | 168 | 12.478 | −2.418 | −51.629 | 1.00 | 28.34 A |
| ATOM | 749 | OD1 | ASP | A | 168 | 11.679 | −3.193 | −51.063 | 1.00 | 30.93 A |
| ATOM | 750 | OD2 | ASP | A | 168 | 12.239 | −1.890 | −52.736 | 1.00 | 31.05 A |
| ATOM | 751 | C | ASP | A | 168 | 15.155 | −2.113 | −48.861 | 1.00 | 24.01 A |
| ATOM | 752 | O | ASP | A | 168 | 15.679 | −1.010 | −49.002 | 1.00 | 23.88 A |
| ATOM | 753 | N | GLU | A | 169 | 15.723 | −3.095 | −48.182 | 1.00 | 23.69 A |
| ATOM | 754 | CA | GLU | A | 169 | 17.011 | −2.908 | −47.532 | 1.00 | 23.00 A |
| ATOM | 755 | CB | GLU | A | 169 | 16.997 | −3.555 | −46.149 | 1.00 | 23.01 A |
| ATOM | 756 | CG | GLU | A | 169 | 16.073 | −2.907 | −45.142 | 1.00 | 24.80 A |
| ATOM | 757 | CD | GLU | A | 169 | 16.034 | −3.679 | −43.833 | 1.00 | 25.40 A |
| ATOM | 758 | OE1 | GLU | A | 169 | 17.108 | −4.145 | −43.398 | 1.00 | 24.55 A |
| ATOM | 759 | OE2 | GLU | A | 169 | 14.940 | −3.814 | −43.240 | 1.00 | 25.14 A |
| ATOM | 760 | C | GLU | A | 169 | 18.182 | −3.478 | −48.305 | 1.00 | 21.78 A |
| ATOM | 761 | O | GLU | A | 169 | 18.068 | −4.495 | −48.979 | 1.00 | 21.39 A |
| ATOM | 762 | N | GLY | A | 170 | 19.312 | −2.797 | −48.196 | 1.00 | 20.18 A |
| ATOM | 763 | CA | GLY | A | 170 | 20.526 | −3.262 | −48.826 | 1.00 | 19.41 A |
| ATOM | 764 | C | GLY | A | 170 | 21.488 | −3.541 | −47.684 | 1.00 | 19.42 A |

-continued

| | | | | | | | | | | |
|---|---|---|---|---|---|---|---|---|---|---|
| ATOM | 765 | O | GLY | A | 170 | 21.205 | −3.179 | −46.533 | 1.00 | 18.09 A |
| ATOM | 766 | N | CYS | A | 171 | 22.609 | −4.189 | −47.983 | 1.00 | 17.85 A |
| ATOM | 767 | CA | CYS | A | 171 | 23.617 | −4.495 | −46.973 | 1.00 | 17.78 A |
| ATOM | 768 | CB | CYS | A | 171 | 23.274 | −5.793 | −46.222 | 1.00 | 17.35 A |
| ATOM | 769 | SG | CYS | A | 171 | 24.482 | −6.273 | −44.946 | 1.00 | 17.05 A |
| ATOM | 770 | C | CYS | A | 171 | 24.956 | −4.644 | −47.667 | 1.00 | 17.66 A |
| ATOM | 771 | O | CYS | A | 171 | 25.051 | −5.264 | −48.731 | 1.00 | 18.62 A |
| ATOM | 772 | N | LEU | A | 172 | 25.988 | −4.071 | −47.060 | 1.00 | 18.65 A |
| ATOM | 773 | CA | LEU | A | 172 | 27.337 | −4.120 | −47.607 | 1.00 | 17.51 A |
| ATOM | 774 | CB | LEU | A | 172 | 28.268 | −3.218 | −46.780 | 1.00 | 18.35 A |
| ATOM | 775 | CG | LEU | A | 172 | 28.433 | −1.739 | −47.177 | 1.00 | 18.16 A |
| ATOM | 776 | CD1 | LEU | A | 172 | 27.382 | −1.317 | −48.180 | 1.00 | 19.26 A |
| ATOM | 777 | CD2 | LEU | A | 172 | 28.373 | −0.875 | −45.930 | 1.00 | 17.19 A |
| ATOM | 778 | C | LEU | A | 172 | 27.895 | −5.537 | −47.672 | 1.00 | 17.16 A |
| ATOM | 779 | O | LEU | A | 172 | 28.819 | −5.811 | −48.438 | 1.00 | 19.43 A |
| ATOM | 780 | N | SER | A | 173 | 27.335 | −6.442 | −46.879 | 1.00 | 15.56 A |
| ATOM | 781 | CA | SER | A | 173 | 27.807 | −7.822 | −46.880 | 1.00 | 15.09 A |
| ATOM | 782 | CB | SER | A | 173 | 27.627 | −8.438 | −45.498 | 1.00 | 13.35 A |
| ATOM | 783 | OG | SER | A | 173 | 28.432 | −7.766 | −44.542 | 1.00 | 13.38 A |
| ATOM | 784 | C | SER | A | 173 | 27.077 | −8.668 | −47.920 | 1.00 | 16.25 A |
| ATOM | 785 | O | SER | A | 173 | 27.318 | −9.872 | −48.037 | 1.00 | 16.75 A |
| ATOM | 786 | N | PHE | A | 174 | 26.180 | −8.029 | −48.664 | 1.00 | 16.57 A |
| ATOM | 787 | CA | PHE | A | 174 | 25.396 | −8.688 | −49.709 | 1.00 | 17.10 A |
| ATOM | 788 | CB | PHE | A | 174 | 23.954 | −8.905 | −49.235 | 1.00 | 18.18 A |
| ATOM | 789 | CG | PHE | A | 174 | 23.819 | −9.875 | −48.085 | 1.00 | 17.61 A |
| ATOM | 790 | CD1 | PHE | A | 174 | 23.432 | −11.196 | −48.313 | 1.00 | 17.43 A |
| ATOM | 791 | CD2 | PHE | A | 174 | 24.047 | −9.461 | −46.775 | 1.00 | 18.73 A |
| ATOM | 792 | CE1 | PHE | A | 174 | 23.267 | −12.091 | −47.253 | 1.00 | 16.70 A |
| ATOM | 793 | CE2 | PHE | A | 174 | 23.887 | −10.352 | −45.703 | 1.00 | 19.19 A |
| ATOM | 794 | CZ | PHE | A | 174 | 23.495 | −11.670 | −45.946 | 1.00 | 18.29 A |
| ATOM | 795 | C | PHE | A | 174 | 25.413 | −7.748 | −50.916 | 1.00 | 16.80 A |
| ATOM | 796 | O | PHE | A | 174 | 24.402 | −7.142 | −51.276 | 1.00 | 16.00 A |
| ATOM | 797 | N | PRO | A | 175 | 26.576 | −7.627 | −51.562 | 1.00 | 18.42 A |
| ATOM | 798 | CD | PRO | A | 175 | 27.766 | −8.470 | −51.335 | 1.00 | 17.82 A |
| ATOM | 799 | CA | PRO | A | 175 | 26.771 | −6.762 | −52.728 | 1.00 | 19.70 A |
| ATOM | 800 | CB | PRO | A | 175 | 28.048 | −7.317 | −53.350 | 1.00 | 20.05 A |
| ATOM | 801 | CG | PRO | A | 175 | 28.826 | −7.755 | −52.138 | 1.00 | 18.23 A |
| ATOM | 802 | C | PRO | A | 175 | 25.617 | −6.700 | −53.716 | 1.00 | 20.20 A |
| ATOM | 803 | O | PRO | A | 175 | 25.240 | −7.710 | −54.312 | 1.00 | 20.33 A |
| ATOM | 804 | N | GLY | A | 176 | 25.059 | −5.497 | −53.866 | 1.00 | 21.23 A |
| ATOM | 805 | CA | GLY | A | 176 | 23.968 | −5.260 | −54.800 | 1.00 | 19.68 A |
| ATOM | 806 | C | GLY | A | 176 | 22.669 | −6.019 | −54.598 | 1.00 | 18.84 A |
| ATOM | 807 | O | GLY | A | 176 | 21.826 | −6.065 | −55.498 | 1.00 | 16.30 A |
| ATOM | 808 | N | ILE | A | 177 | 22.487 | −6.621 | −53.430 | 1.00 | 18.40 A |
| ATOM | 809 | CA | ILE | A | 177 | 21.256 | −7.355 | −53.186 | 1.00 | 19.40 A |
| ATOM | 810 | CB | ILE | A | 177 | 21.547 | −8.683 | −52.450 | 1.00 | 19.34 A |
| ATOM | 811 | CG2 | ILE | A | 177 | 20.250 | −9.372 | −52.066 | 1.00 | 20.31 A |
| ATOM | 812 | CG1 | ILE | A | 177 | 22.398 | −9.584 | −53.352 | 1.00 | 20.29 A |
| ATOM | 813 | CD1 | ILE | A | 177 | 22.776 | −10.927 | −52.735 | 1.00 | 18.41 A |
| ATOM | 814 | C | ILE | A | 177 | 20.278 | −6.498 | −52.391 | 1.00 | 19.23 A |
| ATOM | 815 | O | ILE | A | 177 | 20.642 | −5.904 | −51.378 | 1.00 | 18.56 A |
| ATOM | 816 | N | TYR | A | 178 | 19.043 | −6.408 | −52.878 | 1.00 | 20.54 A |
| ATOM | 817 | CA | TYR | A | 178 | 18.014 | −5.624 | −52.199 | 1.00 | 22.95 A |
| ATOM | 818 | CB | TYR | A | 178 | 17.813 | −4.266 | −52.879 | 1.00 | 24.10 A |
| ATOM | 819 | CG | TYR | A | 178 | 19.064 | −3.420 | −52.962 | 1.00 | 27.38 A |
| ATOM | 820 | CD1 | TYR | A | 178 | 20.069 | −3.721 | −53.888 | 1.00 | 26.85 A |
| ATOM | 821 | CE1 | TYR | A | 178 | 21.235 | −2.962 | −53.962 | 1.00 | 27.02 A |
| ATOM | 822 | CD2 | TYR | A | 178 | 19.258 | −2.330 | −52.106 | 1.00 | 26.90 A |
| ATOM | 823 | CE2 | TYR | A | 178 | 20.431 | −1.560 | −52.176 | 1.00 | 28.14 A |
| ATOM | 824 | CZ | TYR | A | 178 | 21.414 | −1.888 | −53.111 | 1.00 | 28.84 A |
| ATOM | 825 | OH | TYR | A | 178 | 22.577 | −1.147 | −53.210 | 1.00 | 30.05 A |
| ATOM | 826 | C | TYR | A | 178 | 16.680 | −6.352 | −52.154 | 1.00 | 22.69 A |
| ATOM | 827 | O | TYR | A | 178 | 16.192 | −6.839 | −53.175 | 1.00 | 23.47 A |
| ATOM | 828 | N | ALA | A | 179 | 16.095 | −6.430 | −50.965 | 1.00 | 21.13 A |
| ATOM | 829 | CA | ALA | A | 179 | 14.801 | −7.085 | −50.800 | 1.00 | 21.16 A |
| ATOM | 830 | CB | ALA | A | 179 | 14.991 | −8.557 | −50.478 | 1.00 | 20.57 A |
| ATOM | 831 | C | ALA | A | 179 | 14.021 | −6.390 | −49.697 | 1.00 | 21.14 A |
| ATOM | 832 | O | ALA | A | 179 | 14.597 | −5.699 | −48.855 | 1.00 | 21.11 A |
| ATOM | 833 | N | GLU | A | 180 | 12.706 | −6.569 | −49.706 | 1.00 | 21.61 A |
| ATOM | 834 | CA | GLU | A | 180 | 11.842 | −5.929 | −48.721 | 1.00 | 22.07 A |
| ATOM | 835 | CB | GLU | A | 180 | 10.399 | −5.943 | −49.230 | 1.00 | 24.22 A |
| ATOM | 836 | CG | GLU | A | 180 | 9.437 | −5.163 | −48.352 | 1.00 | 27.20 A |
| ATOM | 837 | CD | GLU | A | 180 | 8.021 | −5.150 | −48.893 | 1.00 | 27.70 A |
| ATOM | 838 | OE1 | GLU | A | 180 | 7.245 | −6.075 | −48.568 | 1.00 | 27.79 A |
| ATOM | 839 | OE2 | GLU | A | 180 | 7.691 | −4.210 | −49.649 | 1.00 | 27.64 A |
| ATOM | 840 | C | GLU | A | 180 | 11.880 | −6.526 | −47.306 | 1.00 | 20.52 A |
| ATOM | 841 | O | GLU | A | 180 | 11.805 | −7.736 | −47.124 | 1.00 | 20.89 A |
| ATOM | 842 | N | VAL | A | 181 | 11.993 | −5.664 | −46.304 | 1.00 | 19.74 A |
| ATOM | 843 | CA | VAL | A | 181 | 11.995 | −6.112 | −44.916 | 1.00 | 20.39 A |

-continued

| | | | | | | | | | | |
|---|---|---|---|---|---|---|---|---|---|---|
| ATOM | 844 | CB | VAL | A | 181 | 13.399 | −5.964 | −44.264 | 1.00 | 20.82 A |
| ATOM | 845 | CG1 | VAL | A | 181 | 13.372 | −6.508 | −42.840 | 1.00 | 20.17 A |
| ATOM | 846 | CG2 | VAL | A | 181 | 14.450 | −6.708 | −45.089 | 1.00 | 18.51 A |
| ATOM | 847 | C | VAL | A | 181 | 10.984 | −5.268 | −44.136 | 1.00 | 20.46 A |
| ATOM | 848 | O | VAL | A | 181 | 10.877 | −4.063 | −44.352 | 1.00 | 20.70 A |
| ATOM | 849 | N | VAL | A | 182 | 10.224 | −5.901 | −43.248 | 1.00 | 20.35 A |
| ATOM | 850 | CA | VAL | A | 182 | 9.235 | −5.183 | −42.443 | 1.00 | 19.16 A |
| ATOM | 851 | CB | VAL | A | 182 | 7.881 | −5.935 | −42.419 | 1.00 | 20.20 A |
| ATOM | 852 | CG1 | VAL | A | 182 | 6.865 | −5.168 | −41.587 | 1.00 | 19.98 A |
| ATOM | 853 | CG2 | VAL | A | 182 | 7.365 | −6.120 | −43.841 | 1.00 | 20.58 A |
| ATOM | 854 | C | VAL | A | 182 | 9.738 | −5.020 | −41.011 | 1.00 | 17.95 A |
| ATOM | 855 | O | VAL | A | 182 | 10.083 | −6.001 | −40.353 | 1.00 | 18.95 A |
| ATOM | 856 | N | ARG | A | 183 | 9.789 | −3.781 | −40.531 | 1.00 | 16.50 A |
| ATOM | 857 | CA | ARG | A | 183 | 10.257 | −3.516 | −39.169 | 1.00 | 14.82 A |
| ATOM | 858 | CB | ARG | A | 183 | 11.713 | −3.036 | −39.167 | 1.00 | 15.48 A |
| ATOM | 859 | CG | ARG | A | 183 | 12.749 | −3.901 | −39.862 | 1.00 | 12.14 A |
| ATOM | 860 | CD | ARG | A | 183 | 14.098 | −3.199 | −39.730 | 1.00 | 13.95 A |
| ATOM | 861 | NE | ARG | A | 183 | 15.172 | −3.826 | −40.492 | 1.00 | 14.27 A |
| ATOM | 862 | CZ | ARG | A | 183 | 15.907 | −4.844 | −40.062 | 1.00 | 14.82 A |
| ATOM | 863 | NH1 | ARG | A | 183 | 15.687 | −5.361 | −38.856 | 1.00 | 13.88 A |
| ATOM | 864 | NH2 | ARG | A | 183 | 16.863 | −5.342 | −40.845 | 1.00 | 10.27 A |
| ATOM | 865 | C | ARG | A | 183 | 9.436 | −2.421 | −38.502 | 1.00 | 15.01 A |
| ATOM | 866 | O | ARG | A | 183 | 8.731 | −1.658 | −39.172 | 1.00 | 13.85 A |
| ATOM | 867 | N | PRO | A | 184 | 9.512 | −2.332 | −37.161 | 1.00 | 14.58 A |
| ATOM | 868 | CD | PRO | A | 184 | 10.141 | −3.264 | −36.206 | 1.00 | 13.75 A |
| ATOM | 869 | CA | PRO | A | 184 | 8.764 | −1.285 | −36.458 | 1.00 | 14.05 A |
| ATOM | 870 | CB | PRO | A | 184 | 9.171 | −1.496 | −35.001 | 1.00 | 13.48 A |
| ATOM | 871 | CG | PRO | A | 184 | 9.379 | −2.981 | −34.926 | 1.00 | 13.61 A |
| ATOM | 872 | C | PRO | A | 184 | 9.287 | 0.035 | −37.030 | 1.00 | 13.54 A |
| ATOM | 873 | O | PRO | A | 184 | 10.463 | 0.123 | −37.394 | 1.00 | 12.47 A |
| ATOM | 874 | N | GLN | A | 185 | 8.437 | 1.052 | −37.121 | 1.00 | 14.24 A |
| ATOM | 875 | CA | GLN | A | 185 | 8.867 | 2.326 | −37.703 | 1.00 | 16.35 A |
| ATOM | 876 | CB | GLN | A | 185 | 7.647 | 3.160 | −38.144 | 1.00 | 16.49 A |
| ATOM | 877 | CG | GLN | A | 185 | 6.647 | 3.488 | −37.053 | 1.00 | 18.19 A |
| ATOM | 878 | CD | GLN | A | 185 | 5.486 | 4.339 | −37.562 | 1.00 | 20.93 A |
| ATOM | 879 | OE1 | GLN | A | 185 | 5.126 | 4.276 | −38.735 | 1.00 | 22.48 A |
| ATOM | 880 | NE2 | GLN | A | 185 | 4.886 | 5.126 | −36.672 | 1.00 | 19.77 A |
| ATOM | 881 | C | GLN | A | 185 | 9.783 | 3.191 | −36.843 | 1.00 | 16.52 A |
| ATOM | 882 | O | GLN | A | 185 | 10.467 | 4.071 | −37.358 | 1.00 | 16.86 A |
| ATOM | 883 | N | SER | A | 186 | 9.804 | 2.951 | −35.540 | 1.00 | 17.54 A |
| ATOM | 884 | CA | SER | A | 186 | 10.642 | 3.749 | −34.655 | 1.00 | 17.28 A |
| ATOM | 885 | CB | SER | A | 186 | 9.888 | 4.984 | −34.193 | 1.00 | 16.83 A |
| ATOM | 886 | OG | SER | A | 186 | 8.814 | 4.597 | −33.365 | 1.00 | 16.18 A |
| ATOM | 887 | C | SER | A | 186 | 11.087 | 2.963 | −33.433 | 1.00 | 18.56 A |
| ATOM | 888 | O | SER | A | 186 | 10.483 | 1.948 | −33.072 | 1.00 | 17.15 A |
| ATOM | 889 | N | VAL | A | 187 | 12.145 | 3.454 | −32.794 | 1.00 | 18.41 A |
| ATOM | 890 | CA | VAL | A | 187 | 12.707 | 2.812 | −31.614 | 1.00 | 17.19 A |
| ATOM | 891 | CB | VAL | A | 187 | 13.880 | 1.875 | −31.990 | 1.00 | 16.71 A |
| ATOM | 892 | CG1 | VAL | A | 187 | 13.376 | 0.651 | −32.717 | 1.00 | 14.52 A |
| ATOM | 893 | CG2 | VAL | A | 187 | 14.868 | 2.629 | −32.869 | 1.00 | 16.52 A |
| ATOM | 894 | C | VAL | A | 187 | 13.257 | 3.845 | −30.643 | 1.00 | 19.68 A |
| ATOM | 895 | O | VAL | A | 187 | 13.471 | 5.012 | −30.991 | 1.00 | 17.36 A |
| ATOM | 896 | N | LYS | A | 188 | 13.488 | 3.379 | −29.422 | 1.00 | 22.44 A |
| ATOM | 897 | CA | LYS | A | 188 | 14.041 | 4.170 | −28.333 | 1.00 | 24.50 A |
| ATOM | 898 | CB | LYS | A | 188 | 13.044 | 4.223 | −27.175 | 1.00 | 27.86 A |
| ATOM | 899 | CG | LYS | A | 188 | 13.634 | 4.704 | −25.858 | 1.00 | 32.55 A |
| ATOM | 900 | CD | LYS | A | 188 | 12.604 | 4.645 | −24.724 | 1.00 | 37.24 A |
| ATOM | 901 | CE | LYS | A | 188 | 11.438 | 5.613 | −24.952 | 1.00 | 39.23 A |
| ATOM | 902 | NZ | LYS | A | 188 | 10.474 | 5.621 | −23.803 | 1.00 | 40.21 A |
| ATOM | 903 | C | LYS | A | 188 | 15.291 | 3.399 | −27.925 | 1.00 | 24.24 A |
| ATOM | 904 | O | LYS | A | 188 | 15.202 | 2.222 | −27.574 | 1.00 | 25.34 A |
| ATOM | 905 | N | ILE | A | 189 | 16.449 | 4.049 | −27.976 | 1.00 | 25.02 A |
| ATOM | 906 | CA | ILE | A | 189 | 17.707 | 3.382 | −27.648 | 1.00 | 25.74 A |
| ATOM | 907 | CB | ILE | A | 189 | 18.677 | 3.413 | −28.853 | 1.00 | 25.43 A |
| ATOM | 908 | CG2 | ILE | A | 189 | 19.959 | 2.665 | −28.520 | 1.00 | 27.70 A |
| ATOM | 909 | CG1 | ILE | A | 189 | 18.010 | 2.801 | −30.084 | 1.00 | 25.02 A |
| ATOM | 910 | CD1 | ILE | A | 189 | 17.209 | 3.794 | −30.886 | 1.00 | 26.73 A |
| ATOM | 911 | C | ILE | A | 189 | 18.476 | 3.936 | −26.452 | 1.00 | 26.55 A |
| ATOM | 912 | O | ILE | A | 189 | 18.340 | 5.098 | −26.080 | 1.00 | 28.56 A |
| ATOM | 913 | N | ASP | A | 190 | 19.296 | 3.071 | −25.867 | 1.00 | 26.77 A |
| ATOM | 914 | CA | ASP | A | 190 | 20.167 | 3.398 | −24.745 | 1.00 | 25.30 A |
| ATOM | 915 | CB | ASP | A | 190 | 19.769 | 2.591 | −23.506 | 1.00 | 27.91 A |
| ATOM | 916 | CG | ASP | A | 190 | 19.126 | 3.447 | −22.425 | 1.00 | 29.11 A |
| ATOM | 917 | OD1 | ASP | A | 190 | 18.312 | 4.335 | −22.757 | 1.00 | 32.09 A |
| ATOM | 918 | OD2 | ASP | A | 190 | 19.428 | 3.220 | −21.235 | 1.00 | 31.65 A |
| ATOM | 919 | C | ASP | A | 190 | 21.527 | 2.930 | −25.249 | 1.00 | 23.53 A |
| ATOM | 920 | O | ASP | A | 190 | 21.631 | 1.846 | −25.814 | 1.00 | 25.23 A |
| ATOM | 921 | N | ALA | A | 191 | 22.564 | 3.735 | −25.073 | 1.00 | 20.98 A |
| ATOM | 922 | CA | ALA | A | 191 | 23.889 | 3.339 | −25.536 | 1.00 | 19.22 A |

-continued

| ATOM | 923 | CB | ALA | A | 191 | 23.975 | 3.501 | −27.052 | 1.00 | 16.43 | A |
|---|---|---|---|---|---|---|---|---|---|---|---|
| ATOM | 924 | C | ALA | A | 191 | 24.961 | 4.179 | −24.869 | 1.00 | 16.73 | A |
| ATOM | 925 | O | ALA | A | 191 | 24.659 | 5.021 | −24.031 | 1.00 | 14.46 | A |
| ATOM | 926 | N | ARG | A | 192 | 26.215 | 3.932 | −25.241 | 1.00 | 17.62 | A |
| ATOM | 927 | CA | ARG | A | 192 | 27.344 | 4.701 | −24.719 | 1.00 | 16.89 | A |
| ATOM | 928 | CB | ARG | A | 192 | 28.344 | 3.813 | −23.983 | 1.00 | 14.64 | A |
| ATOM | 929 | CG | ARG | A | 192 | 27.849 | 3.112 | −22.736 | 1.00 | 16.43 | A |
| ATOM | 930 | CD | ARG | A | 192 | 28.933 | 2.152 | −22.266 | 1.00 | 14.30 | A |
| ATOM | 931 | NE | ARG | A | 192 | 28.564 | 1.361 | −21.099 | 1.00 | 17.12 | A |
| ATOM | 932 | CZ | ARG | A | 192 | 28.434 | 1.847 | −19.868 | 1.00 | 17.79 | A |
| ATOM | 933 | NH1 | ARG | A | 192 | 28.638 | 3.137 | −19.629 | 1.00 | 18.41 | A |
| ATOM | 934 | NH2 | ARG | A | 192 | 28.116 | 1.035 | −18.869 | 1.00 | 16.93 | A |
| ATOM | 935 | C | ARG | A | 192 | 28.060 | 5.305 | −25.921 | 1.00 | 16.09 | A |
| ATOM | 936 | O | ARG | A | 192 | 27.943 | 4.800 | −27.029 | 1.00 | 14.43 | A |
| ATOM | 937 | N | ASP | A | 193 | 28.808 | 6.378 | −25.691 | 1.00 | 17.73 | A |
| ATOM | 938 | CA | ASP | A | 193 | 29.574 | 7.023 | −26.750 | 1.00 | 19.68 | A |
| ATOM | 939 | CB | ASP | A | 193 | 29.559 | 8.543 | −26.557 | 1.00 | 21.17 | A |
| ATOM | 940 | CG | ASP | A | 193 | 30.420 | 8.997 | −25.394 | 1.00 | 22.73 | A |
| ATOM | 941 | OD1 | ASP | A | 193 | 30.523 | 8.270 | −24.381 | 1.00 | 23.37 | A |
| ATOM | 942 | OD2 | ASP | A | 193 | 30.991 | 10.101 | −25.493 | 1.00 | 26.89 | A |
| ATOM | 943 | C | ASP | A | 193 | 30.997 | 6.462 | −26.634 | 1.00 | 19.97 | A |
| ATOM | 944 | O | ASP | A | 193 | 31.235 | 5.571 | −25.815 | 1.00 | 17.40 | A |
| ATOM | 945 | N | ILE | A | 194 | 31.937 | 6.971 | −27.430 | 1.00 | 20.45 | A |
| ATOM | 946 | CA | ILE | A | 194 | 33.304 | 6.451 | −27.385 | 1.00 | 21.45 | A |
| ATOM | 947 | CB | ILE | A | 194 | 34.173 | 6.962 | −28.554 | 1.00 | 21.84 | A |
| ATOM | 948 | CG2 | ILE | A | 194 | 33.679 | 6.381 | −29.862 | 1.00 | 22.88 | A |
| ATOM | 949 | CG1 | ILE | A | 194 | 34.180 | 8.488 | −28.592 | 1.00 | 22.27 | A |
| ATOM | 950 | CD1 | ILE | A | 194 | 35.136 | 9.058 | −29.644 | 1.00 | 23.29 | A |
| ATOM | 951 | C | ILE | A | 194 | 34.057 | 6.732 | −26.093 | 1.00 | 22.29 | A |
| ATOM | 952 | O | ILE | A | 194 | 35.073 | 6.098 | −25.824 | 1.00 | 23.35 | A |
| ATOM | 953 | N | THR | A | 195 | 33.574 | 7.676 | −25.292 | 1.00 | 21.53 | A |
| ATOM | 954 | CA | THR | A | 195 | 34.248 | 7.978 | −24.035 | 1.00 | 22.32 | A |
| ATOM | 955 | CB | THR | A | 195 | 34.119 | 9.478 | −23.636 | 1.00 | 21.72 | A |
| ATOM | 956 | OG1 | THR | A | 195 | 32.741 | 9.811 | −23.418 | 1.00 | 18.57 | A |
| ATOM | 957 | CG2 | THR | A | 195 | 34.694 | 10.370 | −24.723 | 1.00 | 20.26 | A |
| ATOM | 958 | C | THR | A | 195 | 33.632 | 7.118 | −22.941 | 1.00 | 22.63 | A |
| ATOM | 959 | O | THR | A | 195 | 34.074 | 7.143 | −21.791 | 1.00 | 21.86 | A |
| ATOM | 960 | N | GLY | A | 196 | 32.601 | 6.363 | −23.313 | 1.00 | 23.03 | A |
| ATOM | 961 | CA | GLY | A | 196 | 31.930 | 5.493 | −22.365 | 1.00 | 23.21 | A |
| ATOM | 962 | C | GLY | A | 196 | 30.759 | 6.147 | −21.660 | 1.00 | 24.01 | A |
| ATOM | 963 | O | GLY | A | 196 | 30.146 | 5.535 | −20.792 | 1.00 | 23.82 | A |
| ATOM | 964 | N | GLU | A | 197 | 30.445 | 7.389 | −22.019 | 1.00 | 26.36 | A |
| ATOM | 965 | CA | GLU | A | 197 | 29.325 | 8.080 | −21.391 | 1.00 | 27.87 | A |
| ATOM | 966 | CB | GLU | A | 197 | 29.437 | 9.598 | −21.558 | 1.00 | 30.06 | A |
| ATOM | 967 | CG | GLU | A | 197 | 30.667 | 10.225 | −20.908 | 1.00 | 35.75 | A |
| ATOM | 968 | CD | GLU | A | 197 | 30.787 | 9.923 | −19.420 | 1.00 | 39.16 | A |
| ATOM | 969 | OE1 | GLU | A | 197 | 31.824 | 10.299 | −18.825 | 1.00 | 42.10 | A |
| ATOM | 970 | OE2 | GLU | A | 197 | 29.857 | 9.312 | −18.844 | 1.00 | 39.72 | A |
| ATOM | 971 | C | GLU | A | 197 | 28.037 | 7.593 | −22.020 | 1.00 | 27.80 | A |
| ATOM | 972 | O | GLU | A | 197 | 27.955 | 7.420 | −23.236 | 1.00 | 28.26 | A |
| ATOM | 973 | N | ARG | A | 198 | 27.031 | 7.365 | −21.189 | 1.00 | 28.14 | A |
| ATOM | 974 | CA | ARG | A | 198 | 25.753 | 6.885 | −21.682 | 1.00 | 28.82 | A |
| ATOM | 975 | CB | ARG | A | 198 | 24.991 | 6.185 | −20.561 | 1.00 | 32.41 | A |
| ATOM | 976 | CG | ARG | A | 198 | 25.853 | 5.255 | −19.720 | 1.00 | 37.31 | A |
| ATOM | 977 | CD | ARG | A | 198 | 25.068 | 4.036 | −19.282 | 1.00 | 42.63 | A |
| ATOM | 978 | NE | ARG | A | 198 | 24.541 | 3.322 | −20.444 | 1.00 | 46.58 | A |
| ATOM | 979 | CZ | ARG | A | 198 | 24.024 | 2.100 | −20.403 | 1.00 | 48.75 | A |
| ATOM | 980 | NH1 | ARG | A | 198 | 23.964 | 1.445 | −19.247 | 1.00 | 48.98 | A |
| ATOM | 981 | NH2 | ARG | A | 198 | 23.564 | 1.535 | −21.518 | 1.00 | 48.98 | A |
| ATOM | 982 | C | ARG | A | 198 | 24.900 | 8.016 | −22.243 | 1.00 | 27.54 | A |
| ATOM | 983 | O | ARG | A | 198 | 25.071 | 9.189 | −21.891 | 1.00 | 27.87 | A |
| ATOM | 984 | N | PHE | A | 199 | 23.986 | 7.653 | −23.132 | 1.00 | 25.20 | A |
| ATOM | 985 | CA | PHE | A | 199 | 23.079 | 8.613 | −23.728 | 1.00 | 23.21 | A |
| ATOM | 986 | CB | PHE | A | 199 | 23.769 | 9.393 | −24.858 | 1.00 | 21.17 | A |
| ATOM | 987 | CG | PHE | A | 199 | 24.088 | 8.572 | −26.084 | 1.00 | 19.11 | A |
| ATOM | 988 | CD1 | PHE | A | 199 | 23.124 | 8.359 | −27.070 | 1.00 | 17.06 | A |
| ATOM | 989 | CD2 | PHE | A | 199 | 25.373 | 8.049 | −26.273 | 1.00 | 18.18 | A |
| ATOM | 990 | CE1 | PHE | A | 199 | 23.437 | 7.639 | −28.232 | 1.00 | 17.14 | A |
| ATOM | 991 | CE2 | PHE | A | 199 | 25.698 | 7.328 | −27.425 | 1.00 | 14.22 | A |
| ATOM | 992 | CZ | PHE | A | 199 | 24.731 | 7.124 | −28.407 | 1.00 | 16.27 | A |
| ATOM | 993 | C | PHE | A | 199 | 21.859 | 7.871 | −24.243 | 1.00 | 23.72 | A |
| ATOM | 994 | O | PHE | A | 199 | 21.898 | 6.659 | −24.450 | 1.00 | 21.75 | A |
| ATOM | 995 | N | SER | A | 200 | 20.769 | 8.600 | −24.431 | 1.00 | 25.35 | A |
| ATOM | 996 | CA | SER | A | 200 | 19.541 | 8.000 | −24.915 | 1.00 | 26.06 | A |
| ATOM | 997 | CB | SER | A | 200 | 18.551 | 7.844 | −23.767 | 1.00 | 26.35 | A |
| ATOM | 998 | OG | SER | A | 200 | 19.115 | 7.060 | −22.732 | 1.00 | 29.16 | A |
| ATOM | 999 | C | SER | A | 200 | 18.941 | 8.867 | −25.996 | 1.00 | 26.17 | A |
| ATOM | 1000 | O | SER | A | 200 | 18.994 | 10.092 | −25.915 | 1.00 | 27.31 | A |
| ATOM | 1001 | N | ILE | A | 201 | 18.376 | 8.226 | −27.013 | 1.00 | 26.58 | A |

-continued

| | | | | | | | | | |
|---|---|---|---|---|---|---|---|---|---|
| ATOM | 1002 | CA | ILE | A | 201 | 17.756 | 8.942 | −28.118 | 1.00 26.23 A |
| ATOM | 1003 | CB | ILE | A | 201 | 18.762 | 9.214 | −29.250 | 1.00 28.26 A |
| ATOM | 1004 | CG2 | ILE | A | 201 | 19.813 | 10.216 | −28.790 | 1.00 29.33 A |
| ATOM | 1005 | CG1 | ILE | A | 201 | 19.394 | 7.895 | −29.701 | 1.00 28.98 A |
| ATOM | 1006 | CD1 | ILE | A | 201 | 20.230 | 8.010 | −30.962 | 1.00 31.66 A |
| ATOM | 1007 | C | ILE | A | 201 | 16.593 | 8.152 | −28.709 | 1.00 25.11 A |
| ATOM | 1008 | O | ILE | A | 201 | 16.418 | 6.958 | −28.434 | 1.00 23.45 A |
| ATOM | 1009 | N | SER | A | 202 | 15.796 | 8.833 | −29.522 | 1.00 24.09 A |
| ATOM | 1010 | CA | SER | A | 202 | 14.657 | 8.209 | −30.180 | 1.00 23.76 A |
| ATOM | 1011 | CB | SER | A | 202 | 13.356 | 8.918 | −29.802 | 1.00 23.27 A |
| ATOM | 1012 | OG | SER | A | 202 | 13.018 | 8.677 | −28.447 | 1.00 26.12 A |
| ATOM | 1013 | C | SER | A | 202 | 14.864 | 8.297 | −31.676 | 1.00 22.76 A |
| ATOM | 1014 | O | SER | A | 202 | 15.181 | 9.357 | −32.205 | 1.00 20.95 A |
| ATOM | 1015 | N | LEU | A | 203 | 14.708 | 7.178 | −32.364 | 1.00 22.93 A |
| ATOM | 1016 | CA | LEU | A | 203 | 14.871 | 7.193 | −33.804 | 1.00 23.93 A |
| ATOM | 1017 | CB | LEU | A | 203 | 16.005 | 6.257 | −34.237 | 1.00 23.48 A |
| ATOM | 1018 | CG | LEU | A | 203 | 17.387 | 6.575 | −33.669 | 1.00 23.22 A |
| ATOM | 1019 | CD1 | LEU | A | 203 | 18.414 | 5.669 | −34.321 | 1.00 23.21 A |
| ATOM | 1020 | CD2 | LEU | A | 203 | 17.727 | 8.039 | −33.914 | 1.00 21.89 A |
| ATOM | 1021 | C | LEU | A | 203 | 13.585 | 6.795 | −34.498 | 1.00 23.86 A |
| ATOM | 1022 | O | LEU | A | 203 | 12.781 | 6.024 | −33.966 | 1.00 24.42 A |
| ATOM | 1023 | N | SER | A | 204 | 13.396 | 7.350 | −35.685 | 1.00 25.11 A |
| ATOM | 1024 | CA | SER | A | 204 | 12.237 | 7.060 | −36.514 | 1.00 27.28 A |
| ATOM | 1025 | CB | SER | A | 204 | 11.111 | 8.051 | −36.236 | 1.00 28.55 A |
| ATOM | 1026 | OG | SER | A | 204 | 11.482 | 9.351 | −36.658 | 1.00 30.10 A |
| ATOM | 1027 | C | SER | A | 204 | 12.741 | 7.248 | −37.934 | 1.00 27.55 A |
| ATOM | 1028 | O | SER | A | 204 | 13.933 | 7.502 | −38.137 | 1.00 27.70 A |
| ATOM | 1029 | N | ARG | A | 205 | 11.845 | 7.133 | −38.910 | 1.00 28.31 A |
| ATOM | 1030 | CA | ARG | A | 205 | 12.221 | 7.315 | −40.307 | 1.00 28.06 A |
| ATOM | 1031 | CB | ARG | A | 205 | 12.594 | 8.777 | −40.569 | 1.00 31.86 A |
| ATOM | 1032 | CG | ARG | A | 205 | 11.428 | 9.756 | −40.709 | 1.00 36.98 A |
| ATOM | 1033 | CD | ARG | A | 205 | 11.988 | 11.169 | −40.867 | 1.00 40.88 A |
| ATOM | 1034 | NE | ARG | A | 205 | 11.122 | 12.070 | −41.621 | 1.00 44.32 A |
| ATOM | 1035 | CZ | ARG | A | 205 | 11.423 | 13.343 | −41.879 | 1.00 47.87 A |
| ATOM | 1036 | NH1 | ARG | A | 205 | 12.568 | 13.861 | −41.442 | 1.00 48.05 A |
| ATOM | 1037 | NH2 | ARG | A | 205 | 10.583 | 14.107 | −42.573 | 1.00 48.10 A |
| ATOM | 1038 | C | ARG | A | 205 | 13.396 | 6.424 | −40.706 | 1.00 25.68 A |
| ATOM | 1039 | O | ARG | A | 205 | 13.523 | 5.293 | −40.235 | 1.00 24.48 A |
| ATOM | 1040 | N | LEU | A | 206 | 14.261 | 6.958 | −41.563 | 1.00 21.87 A |
| ATOM | 1041 | CA | LEU | A | 206 | 15.413 | 6.219 | −42.057 | 1.00 19.85 A |
| ATOM | 1042 | CB | LEU | A | 206 | 16.115 | 7.006 | −43.166 | 1.00 20.52 A |
| ATOM | 1043 | CG | LEU | A | 206 | 17.278 | 6.277 | −43.856 | 1.00 23.37 A |
| ATOM | 1044 | CD1 | LEU | A | 206 | 16.765 | 5.016 | −44.565 | 1.00 20.22 A |
| ATOM | 1045 | CD2 | LEU | A | 206 | 17.951 | 7.217 | −44.853 | 1.00 22.79 A |
| ATOM | 1046 | C | LEU | A | 206 | 16.420 | 5.854 | −40.974 | 1.00 18.21 A |
| ATOM | 1047 | O | LEU | A | 206 | 16.921 | 4.727 | −40.953 | 1.00 16.21 A |
| ATOM | 1048 | N | PRO | A | 207 | 16.742 | 6.799 | −40.069 | 1.00 16.71 A |
| ATOM | 1049 | CD | PRO | A | 207 | 16.439 | 8.245 | −40.087 | 1.00 17.35 A |
| ATOM | 1050 | CA | PRO | A | 207 | 17.709 | 6.487 | −39.008 | 1.00 17.46 A |
| ATOM | 1051 | CB | PRO | A | 207 | 17.795 | 7.794 | −38.217 | 1.00 16.29 A |
| ATOM | 1052 | CG | PRO | A | 207 | 17.588 | 8.828 | −39.283 | 1.00 16.84 A |
| ATOM | 1053 | C | PRO | A | 207 | 17.264 | 5.305 | −38.154 | 1.00 16.91 A |
| ATOM | 1054 | O | PRO | A | 207 | 18.084 | 4.484 | −37.747 | 1.00 18.14 A |
| ATOM | 1055 | N | ALA | A | 208 | 15.963 | 5.212 | −37.896 | 1.00 16.46 A |
| ATOM | 1056 | CA | ALA | A | 208 | 15.437 | 4.106 | −37.104 | 1.00 15.91 A |
| ATOM | 1057 | CB | ALA | A | 208 | 13.967 | 4.344 | −36.780 | 1.00 16.38 A |
| ATOM | 1058 | C | ALA | A | 208 | 15.597 | 2.800 | −37.883 | 1.00 14.15 A |
| ATOM | 1059 | O | ALA | A | 208 | 15.932 | 1.763 | −37.320 | 1.00 14.30 A |
| ATOM | 1060 | N | ARG | A | 209 | 15.357 | 2.862 | −39.187 | 1.00 14.77 A |
| ATOM | 1061 | CA | ARG | A | 209 | 15.473 | 1.686 | −40.041 | 1.00 14.78 A |
| ATOM | 1062 | CB | ARG | A | 209 | 14.910 | 1.999 | −41.434 | 1.00 16.76 A |
| ATOM | 1063 | CG | ARG | A | 209 | 14.841 | 0.804 | −42.360 | 1.00 18.33 A |
| ATOM | 1064 | CD | ARG | A | 209 | 14.418 | −0.437 | −41.596 | 1.00 22.27 A |
| ATOM | 1065 | NE | ARG | A | 209 | 13.889 | −1.463 | −42.480 | 1.00 25.66 A |
| ATOM | 1066 | CZ | ARG | A | 209 | 12.611 | −1.556 | −42.834 | 1.00 28.46 A |
| ATOM | 1067 | NH1 | ARG | A | 209 | 11.709 | −0.687 | −42.377 | 1.00 27.84 A |
| ATOM | 1068 | NH2 | ARG | A | 209 | 12.235 | −2.516 | −43.659 | 1.00 28.08 A |
| ATOM | 1069 | C | ARG | A | 209 | 16.934 | 1.210 | −40.145 | 1.00 14.81 A |
| ATOM | 1070 | O | ARG | A | 209 | 17.224 | 0.025 | −40.001 | 1.00 12.46 A |
| ATOM | 1071 | N | ILE | A | 210 | 17.854 | 2.137 | −40.389 | 1.00 13.90 A |
| ATOM | 1072 | CA | ILE | A | 210 | 19.261 | 1.774 | −40.482 | 1.00 13.38 A |
| ATOM | 1073 | CB | ILE | A | 210 | 20.138 | 3.010 | −40.830 | 1.00 14.75 A |
| ATOM | 1074 | CG2 | ILE | A | 210 | 21.620 | 2.649 | −40.768 | 1.00 13.71 A |
| ATOM | 1075 | CG1 | ILE | A | 210 | 19.775 | 3.526 | −42.229 | 1.00 12.89 A |
| ATOM | 1076 | CD1 | ILE | A | 210 | 20.449 | 4.828 | −42.600 | 1.00 11.08 A |
| ATOM | 1077 | C | ILE | A | 210 | 19.709 | 1.200 | −39.140 | 1.00 14.16 A |
| ATOM | 1078 | O | ILE | A | 210 | 20.444 | 0.210 | −39.092 | 1.00 12.22 A |
| ATOM | 1079 | N | PHE | A | 211 | 19.247 | 1.816 | −38.050 | 1.00 13.33 A |
| ATOM | 1080 | CA | PHE | A | 211 | 19.622 | 1.358 | −36.718 | 1.00 13.42 A |

-continued

| | | | | | | | | | |
|---|---|---|---|---|---|---|---|---|---|
| ATOM | 1081 | CB | PHE | A | 211 | 18.978 | 2.221 | −35.634 | 1.00 | 13.55 A |
| ATOM | 1082 | CG | PHE | A | 211 | 19.137 | 1.642 | −34.261 | 1.00 | 10.76 A |
| ATOM | 1083 | CD1 | PHE | A | 211 | 20.323 | 1.815 | −33.555 | 1.00 | 10.51 A |
| ATOM | 1084 | CD2 | PHE | A | 211 | 18.145 | 0.827 | −33.719 | 1.00 | 11.87 A |
| ATOM | 1085 | CE1 | PHE | A | 211 | 20.522 | 1.175 | −32.328 | 1.00 | 11.75 A |
| ATOM | 1086 | CE2 | PHE | A | 211 | 18.338 | 0.179 | −32.489 | 1.00 | 9.24 A |
| ATOM | 1087 | CZ | PHE | A | 211 | 19.527 | 0.355 | −31.797 | 1.00 | 8.29 A |
| ATOM | 1088 | C | PHE | A | 211 | 19.275 | −0.107 | −36.421 | 1.00 | 13.34 A |
| ATOM | 1089 | O | PHE | A | 211 | 20.108 | −0.863 | −35.901 | 1.00 | 12.59 A |
| ATOM | 1090 | N | GLN | A | 212 | 18.039 | −0.495 | −36.721 | 1.00 | 11.92 A |
| ATOM | 1091 | CA | GLN | A | 212 | 17.590 | −1.860 | −36.468 | 1.00 | 13.18 A |
| ATOM | 1092 | CB | GLN | A | 212 | 16.084 | −1.968 | −36.702 | 1.00 | 12.41 A |
| ATOM | 1093 | CG | GLN | A | 212 | 15.287 | −1.129 | −35.730 | 1.00 | 14.52 A |
| ATOM | 1094 | CD | GLN | A | 212 | 13.820 | −1.126 | −36.049 | 1.00 | 16.44 A |
| ATOM | 1095 | OE1 | GLN | A | 212 | 13.102 | −2.070 | −35.732 | 1.00 | 18.15 A |
| ATOM | 1096 | NE2 | GLN | A | 212 | 13.362 | −0.067 | −36.698 | 1.00 | 17.06 A |
| ATOM | 1097 | C | GLN | A | 212 | 18.341 | −2.887 | −37.313 | 1.00 | 13.31 A |
| ATOM | 1098 | O | GLN | A | 212 | 18.689 | −3.976 | −36.823 | 1.00 | 12.33 A |
| ATOM | 1099 | N | HIS | A | 213 | 18.584 | −2.543 | −38.574 | 1.00 | 12.02 A |
| ATOM | 1100 | CA | HIS | A | 213 | 19.326 | −3.421 | −39.470 | 1.00 | 13.70 A |
| ATOM | 1101 | CB | HIS | A | 213 | 19.485 | −2.754 | −40.845 | 1.00 | 15.78 A |
| ATOM | 1102 | CG | HIS | A | 213 | 20.385 | −3.497 | −41.785 | 1.00 | 16.70 A |
| ATOM | 1103 | CD2 | HIS | A | 213 | 21.733 | −3.494 | −41.917 | 1.00 | 18.08 A |
| ATOM | 1104 | ND1 | HIS | A | 213 | 19.914 | −4.410 | −42.704 | 1.00 | 19.47 A |
| ATOM | 1105 | CE1 | HIS | A | 213 | 20.932 | −4.939 | −43.361 | 1.00 | 18.40 A |
| ATOM | 1106 | NE2 | HIS | A | 213 | 22.047 | −4.401 | −42.901 | 1.00 | 18.23 A |
| ATOM | 1107 | C | HIS | A | 213 | 20.712 | −3.679 | −38.856 | 1.00 | 13.57 A |
| ATOM | 1108 | O | HIS | A | 213 | 21.184 | −4.822 | −38.832 | 1.00 | 13.81 A |
| ATOM | 1109 | N | GLU | A | 214 | 21.347 | −2.621 | −38.346 | 1.00 | 11.88 A |
| ATOM | 1110 | CA | GLU | A | 214 | 22.686 | −2.741 | −37.750 | 1.00 | 13.61 A |
| ATOM | 1111 | CB | GLU | A | 214 | 23.372 | −1.374 | −37.656 | 1.00 | 13.71 A |
| ATOM | 1112 | CG | GLU | A | 214 | 23.547 | −0.614 | −38.972 | 1.00 | 14.63 A |
| ATOM | 1113 | CD | GLU | A | 214 | 24.277 | −1.403 | −40.055 | 1.00 | 17.21 A |
| ATOM | 1114 | OE1 | CLU | A | 214 | 25.122 | −2.266 | −39.730 | 1.00 | 15.04 A |
| ATOM | 1115 | OE2 | GLU | A | 214 | 24.015 | −1.132 | −41.250 | 1.00 | 21.39 A |
| ATOM | 1116 | C | GLU | A | 214 | 22.671 | −3.376 | −36.361 | 1.00 | 14.65 A |
| ATOM | 1117 | O | GLU | A | 214 | 23.628 | −4.041 | −35.957 | 1.00 | 14.69 A |
| ATOM | 1118 | N | TYR | A | 215 | 21.594 | −3.155 | −35.620 | 1.00 | 16.18 A |
| ATOM | 1119 | CA | TYR | A | 215 | 21.488 | −3.742 | −34.298 | 1.00 | 15.85 A |
| ATOM | 1120 | CB | TYR | A | 215 | 20.218 | −3.261 | −33.587 | 1.00 | 17.67 A |
| ATOM | 1121 | CG | TYR | A | 215 | 20.067 | −3.844 | −32.196 | 1.00 | 21.32 A |
| ATOM | 1122 | CD1 | TYR | A | 215 | 20.887 | −3.421 | −31.148 | 1.00 | 19.48 A |
| ATOM | 1123 | CE1 | TYR | A | 215 | 20.798 | −4.003 | −29.883 | 1.00 | 20.09 A |
| ATOM | 1124 | CD2 | TYR | A | 215 | 19.143 | −4.866 | −31.940 | 1.00 | 20.98 A |
| ATOM | 1125 | CE2 | TYR | A | 215 | 19.046 | −5.452 | −30.680 | 1.00 | 20.75 A |
| ATOM | 1126 | CZ | TYR | A | 215 | 19.879 | −5.020 | −29.654 | 1.00 | 21.44 A |
| ATOM | 1127 | OH | TYR | A | 215 | 19.821 | −5.626 | −28.413 | 1.00 | 18.89 A |
| ATOM | 1128 | C | TYR | A | 215 | 21.452 | −5.260 | −34.472 | 1.00 | 14.58 A |
| ATOM | 1129 | O | TYR | A | 215 | 22.055 | −6.007 | −33.689 | 1.00 | 14.06 A |
| ATOM | 1130 | N | ASP | A | 216 | 20.750 | −5.710 | −35.506 | 1.00 | 13.46 A |
| ATOM | 1131 | CA | ASP | A | 216 | 20.657 | −7.135 | −35.787 | 1.00 | 14.06 A |
| ATOM | 1132 | CB | ASP | A | 216 | 19.780 | −7.388 | −37.008 | 1.00 | 13.61 A |
| ATOM | 1133 | CG | ASP | A | 216 | 18.308 | −7.427 | −36.671 | 1.00 | 13.64 A |
| ATOM | 1134 | OD1 | ASP | A | 216 | 17.957 | −7.402 | −35.475 | 1.00 | 12.49 A |
| ATOM | 1135 | OD2 | ASP | A | 216 | 17.495 | −7.489 | −37.611 | 1.00 | 15.97 A |
| ATOM | 1136 | C | ASP | A | 216 | 22.041 | −7.720 | −36.031 | 1.00 | 15.02 A |
| ATOM | 1137 | O | ASP | A | 216 | 22.353 | −8.823 | −35.557 | 1.00 | 16.95 A |
| ATOM | 1138 | N | HIS | A | 217 | 22.863 | −6.988 | −36.779 | 1.00 | 13.44 A |
| ATOM | 1139 | CA | HIS | A | 217 | 24.218 | −7.433 | −37.065 | 1.00 | 13.38 A |
| ATOM | 1140 | CB | HIS | A | 217 | 25.011 | −6.350 | −37.810 | 1.00 | 13.13 A |
| ATOM | 1141 | CG | HIS | A | 217 | 24.825 | −6.370 | −39.293 | 1.00 | 14.65 A |
| ATOM | 1142 | CD2 | HIS | A | 217 | 24.458 | −5.397 | −40.160 | 1.00 | 16.14 A |
| ATOM | 1143 | ND1 | HIS | A | 217 | 25.054 | −7.495 | −40.056 | 1.00 | 14.89 A |
| ATOM | 1144 | CE1 | HIS | A | 217 | 24.836 | −7.214 | −41.328 | 1.00 | 14.42 A |
| ATOM | 1145 | NE2 | HIS | A | 217 | 24.473 | −5.948 | −41.418 | 1.00 | 17.14 A |
| ATOM | 1146 | C | HIS | A | 217 | 24.906 | −7.717 | −35.736 | 1.00 | 14.40 A |
| ATOM | 1147 | O | HIS | A | 217 | 25.659 | −8.684 | −35.604 | 1.00 | 12.69 A |
| ATOM | 1148 | N | LEU | A | 218 | 24.644 | −6.864 | −34.750 | 1.00 | 14.83 A |
| ATOM | 1149 | CA | LEU | A | 218 | 25.255 | −7.037 | −33.445 | 1.00 | 14.51 A |
| ATOM | 1150 | CB | LEU | A | 218 | 25.053 | −5.766 | −32.611 | 1.00 | 12.54 A |
| ATOM | 1151 | CG | LEU | A | 218 | 25.713 | −4.539 | −33.285 | 1.00 | 17.61 A |
| ATOM | 1152 | CD1 | LEU | A | 218 | 25.643 | −3.309 | −32.390 | 1.00 | 16.94 A |
| ATOM | 1153 | CD2 | LEU | A | 218 | 27.180 | −4.856 | −33.619 | 1.00 | 14.59 A |
| ATOM | 1154 | C | LEU | A | 218 | 24.727 | −8.291 | −32.741 | 1.00 | 15.91 A |
| ATOM | 1155 | O | LEU | A | 218 | 25.375 | −8.827 | −31.846 | 1.00 | 17.34 A |
| ATOM | 1156 | N | GLU | A | 219 | 23.564 | −8.774 | −33.164 | 1.00 | 15.63 A |
| ATOM | 1157 | CA | GLU | A | 219 | 22.994 | −9.983 | −32.586 | 1.00 | 18.38 A |
| ATOM | 1158 | CB | GLU | A | 219 | 21.467 | −9.865 | −32.462 | 1.00 | 22.20 A |
| ATOM | 1159 | CG | GLU | A | 219 | 20.962 | −8.892 | −31.401 | 1.00 | 27.10 A |

-continued

| | | | | | | | | | | |
|---|---|---|---|---|---|---|---|---|---|---|
| ATOM | 1160 | CD | GLU | A | 219 | 21.262 | −9.346 | −29.987 | 1.00 | 30.86 A |
| ATOM | 1161 | OE1 | GLU | A | 219 | 21.025 | −10.535 | −29.673 | 1.00 | 33.62 A |
| ATOM | 1162 | OE2 | GLU | A | 219 | 21.723 | −8.510 | −29.183 | 1.00 | 34.35 A |
| ATOM | 1163 | C | GLU | A | 219 | 23.327 | −11.184 | −33.477 | 1.00 | 17.11 A |
| ATOM | 1164 | O | GLU | A | 219 | 22.786 | −12.272 | −33.283 | 1.00 | 17.19 A |
| ATOM | 1165 | N | GLY | A | 220 | 24.220 | −10.983 | −34.444 | 1.00 | 14.72 A |
| ATOM | 1166 | CA | GLY | A | 220 | 24.580 | −12.056 | −35.356 | 1.00 | 12.31 A |
| ATOM | 1167 | C | GLY | A | 220 | 23.423 | −12.355 | −36.302 | 1.00 | 15.10 A |
| ATOM | 1168 | O | GLY | A | 220 | 23.401 | −13.389 | −36.979 | 1.00 | 14.67 A |
| ATOM | 1169 | N | VAL | A | 221 | 22.456 | −11.437 | −36.347 | 1.00 | 14.21 A |
| ATOM | 1170 | CA | VAL | A | 221 | 21.278 | −11.581 | −37.191 | 1.00 | 14.18 A |
| ATOM | 1171 | CB | VAL | A | 221 | 20.023 | −11.047 | −36.462 | 1.00 | 17.59 A |
| ATOM | 1172 | CG1 | VAL | A | 221 | 18.802 | −11.120 | −37.377 | 1.00 | 17.23 A |
| ATOM | 1173 | CG2 | VAL | A | 221 | 19.791 | −11.844 | −35.182 | 1.00 | 15.15 A |
| ATOM | 1174 | C | VAL | A | 221 | 21.418 | −10.848 | −38.529 | 1.00 | 14.45 A |
| ATOM | 1175 | O | VAL | A | 221 | 21.732 | −9.657 | −38.568 | 1.00 | 11.29 A |
| ATOM | 1176 | N | LEU | A | 222 | 21.176 | −11.571 | −39.620 | 1.00 | 13.92 A |
| ATOM | 1177 | CA | LEU | A | 222 | 21.269 | −11.004 | −40.965 | 1.00 | 15.74 A |
| ATOM | 1178 | CB | LEU | A | 222 | 21.972 | −12.000 | −41.893 | 1.00 | 13.26 A |
| ATOM | 1179 | CG | LEU | A | 222 | 23.492 | −11.841 | −42.001 | 1.00 | 13.73 A |
| ATOM | 1180 | CD1 | LEU | A | 222 | 24.070 | −11.302 | −40.699 | 1.00 | 13.62 A |
| ATOM | 1181 | CD2 | LEU | A | 222 | 24.119 | −13.182 | −42.379 | 1.00 | 12.93 A |
| ATOM | 1182 | C | LEU | A | 222 | 19.886 | −10.639 | −41.496 | 1.00 | 15.93 A |
| ATOM | 1183 | O | LEU | A | 222 | 18.906 | −11.326 | −41.198 | 1.00 | 16.25 A |
| ATOM | 1184 | N | PHE | A | 223 | 19.811 | −9.579 | −42.302 | 1.00 | 17.16 A |
| ATOM | 1185 | CA | PHE | A | 223 | 18.529 | −9.097 | −42.815 | 1.00 | 15.87 A |
| ATOM | 1186 | CB | PHE | A | 223 | 18.722 | −7.817 | −43.661 | 1.00 | 17.74 A |
| ATOM | 1187 | CG | PHE | A | 223 | 19.229 | −8.044 | −45.073 | 1.00 | 18.05 A |
| ATOM | 1188 | CD1 | PHE | A | 223 | 20.177 | −9.023 | −45.361 | 1.00 | 19.74 A |
| ATOM | 1189 | CD2 | PHE | A | 223 | 18.803 | −7.207 | −46.109 | 1.00 | 18.79 A |
| ATOM | 1190 | CE1 | PHE | A | 223 | 20.694 | −9.161 | −46.658 | 1.00 | 17.18 A |
| ATOM | 1191 | CE2 | PHE | A | 223 | 19.312 | −7.333 | −47.407 | 1.00 | 14.65 A |
| ATOM | 1192 | CZ | PHE | A | 223 | 20.259 | −8.311 | −47.680 | 1.00 | 18.55 A |
| ATOM | 1193 | C | PHE | A | 223 | 17.635 | −10.089 | −43.539 | 1.00 | 17.30 A |
| ATOM | 1194 | O | PHE | A | 223 | 16.408 | −9.948 | −43.493 | 1.00 | 16.29 A |
| ATOM | 1195 | N | PHE | A | 224 | 18.207 | −11.103 | −44.187 | 1.00 | 16.43 A |
| ATOM | 1196 | CA | PHE | A | 224 | 17.341 | −12.058 | −44.861 | 1.00 | 15.78 A |
| ATOM | 1197 | CB | PHE | A | 224 | 18.116 | −12.898 | −45.906 | 1.00 | 14.49 A |
| ATOM | 1198 | CG | PHE | A | 224 | 19.045 | −13.945 | −45.331 | 1.00 | 12.96 A |
| ATOM | 1199 | CD1 | PHE | A | 224 | 18.548 | −15.152 | −44.854 | 1.00 | 11.77 A |
| ATOM | 1200 | CD2 | PHE | A | 224 | 20.430 | −13.742 | −45.334 | 1.00 | 12.30 A |
| ATOM | 1201 | CE1 | PHE | A | 224 | 19.421 | −16.150 | −44.392 | 1.00 | 12.19 A |
| ATOM | 1202 | CE2 | PHE | A | 224 | 21.314 | −14.720 | −44.877 | 1.00 | 7.51 A |
| ATOM | 1203 | CZ | PHE | A | 224 | 20.812 | −15.930 | −44.405 | 1.00 | 13.32 A |
| ATOM | 1204 | C | PHE | A | 224 | 16.636 | −12.923 | −43.818 | 1.00 | 17.87 A |
| ATOM | 1205 | O | PHE | A | 224 | 15.608 | −13.541 | −44.115 | 1.00 | 16.51 A |
| ATOM | 1206 | N | ASP | A | 225 | 17.175 | −12.930 | −42.592 | 1.00 | 17.97 A |
| ATOM | 1207 | CA | ASP | A | 225 | 16.586 | −13.692 | −41.484 | 1.00 | 17.66 A |
| ATOM | 1208 | CB | ASP | A | 225 | 17.426 | −13.586 | −40.186 | 1.00 | 16.43 A |
| ATOM | 1209 | CG | ASP | A | 225 | 18.781 | −14.305 | −40.260 | 1.00 | 18.04 A |
| ATOM | 1210 | OD1 | ASP | A | 225 | 18.941 | −15.266 | −41.040 | 1.00 | 16.53 A |
| ATOM | 1211 | OD2 | ASP | A | 225 | 19.697 | −13.911 | −39.504 | 1.00 | 17.05 A |
| ATOM | 1212 | C | ASP | A | 225 | 15.182 | −13.151 | −41.163 | 1.00 | 18.56 A |
| ATOM | 1213 | O | ASP | A | 225 | 14.311 | −13.894 | −40.713 | 1.00 | 18.42 A |
| ATOM | 1214 | N | ARG | A | 226 | 14.969 | −11.858 | −41.386 | 1.00 | 18.50 A |
| ATOM | 1215 | CA | ARG | A | 226 | 13.681 | −11.240 | −41.072 | 1.00 | 21.41 A |
| ATOM | 1216 | CB | ARG | A | 226 | 13.915 | −9.901 | −40.360 | 1.00 | 22.31 A |
| ATOM | 1217 | CG | ARG | A | 226 | 14.890 | −10.019 | −39.186 | 1.00 | 25.19 A |
| ATOM | 1218 | CD | ARG | A | 226 | 15.206 | −8.683 | −38.564 | 1.00 | 28.37 A |
| ATOM | 1219 | NE | ARG | A | 226 | 14.317 | −8.367 | −37.451 | 1.00 | 32.73 A |
| ATOM | 1220 | CZ | ARG | A | 226 | 14.361 | −8.965 | −36.264 | 1.00 | 35.61 A |
| ATOM | 1221 | NH1 | ARG | A | 226 | 15.258 | −9.916 | −36.031 | 1.00 | 38.22 A |
| ATOM | 1222 | NH2 | ARG | A | 226 | 13.503 | −8.621 | −35.310 | 1.00 | 35.12 A |
| ATOM | 1223 | C | ARG | A | 226 | 12.758 | −11.044 | −42.279 | 1.00 | 21.52 A |
| ATOM | 1224 | O | ARG | A | 226 | 11.689 | −10.447 | −42.165 | 1.00 | 21.42 A |
| ATOM | 1225 | N | MET | A | 227 | 13.166 | −11.559 | −43.433 | 1.00 | 20.50 A |
| ATOM | 1226 | CA | MET | A | 227 | 12.345 | −11.432 | −44.628 | 1.00 | 20.39 A |
| ATOM | 1227 | CB | MET | A | 227 | 13.202 | −11.585 | −45.884 | 1.00 | 18.95 A |
| ATOM | 1228 | CG | MET | A | 227 | 14.359 | −10.619 | −45.971 | 1.00 | 18.23 A |
| ATOM | 1229 | SD | MET | A | 227 | 15.261 | −10.828 | −47.512 | 1.00 | 16.76 A |
| ATOM | 1230 | CE | MET | A | 227 | 16.117 | −9.282 | −47.571 | 1.00 | 16.68 A |
| ATOM | 1231 | C | MET | A | 227 | 11.275 | −12.515 | −44.620 | 1.00 | 19.32 A |
| ATOM | 1232 | O | MET | A | 227 | 11.432 | −13.547 | −43.969 | 1.00 | 17.02 A |
| ATOM | 1233 | N | THR | A | 228 | 10.180 | −12.271 | −45.324 | 1.00 | 19.28 A |
| ATOM | 1234 | CA | THR | A | 228 | 9.129 | −13.269 | −45.401 | 1.00 | 23.61 A |
| ATOM | 1235 | CB | THR | A | 228 | 7.854 | −12.705 | −46.062 | 1.00 | 23.79 A |
| ATOM | 1236 | OG1 | THR | A | 228 | 8.189 | −12.120 | −47.327 | 1.00 | 22.17 A |
| ATOM | 1237 | CG2 | THR | A | 228 | 7.213 | −11.645 | −45.165 | 1.00 | 20.55 A |
| ATOM | 1238 | C | THR | A | 228 | 9.671 | −14.415 | −46.247 | 1.00 | 26.65 A |

-continued

| | | | | | | | | | | |
|---|---|---|---|---|---|---|---|---|---|---|
| ATOM | 1239 | O | THR | A | 228 | 10.715 | −14.282 | −46.899 | 1.00 | 25.82 A |
| ATOM | 1240 | N | ASP | A | 229 | 8.977 | −15.544 | −46.232 | 1.00 | 29.30 A |
| ATOM | 1241 | CA | ASP | A | 229 | 9.418 | −16.689 | −47.014 | 1.00 | 32.65 A |
| ATOM | 1242 | CB | ASP | A | 229 | 8.494 | −17.890 | −46.756 | 1.00 | 38.87 A |
| ATOM | 1243 | CG | ASP | A | 229 | 8.284 | −18.172 | −45.259 | 1.00 | 45.09 A |
| ATOM | 1244 | OD1 | ASP | A | 229 | 7.796 | −17.274 | −44.534 | 1.00 | 48.75 A |
| ATOM | 1245 | OD2 | ASP | A | 229 | 8.600 | −19.298 | −44.806 | 1.00 | 45.52 A |
| ATOM | 1246 | C | ASP | A | 229 | 9.401 | −16.310 | −48.503 | 1.00 | 32.03 A |
| ATOM | 1247 | O | ASP | A | 229 | 10.309 | −16.660 | −49.258 | 1.00 | 31.02 A |
| ATOM | 1248 | N | GLN | A | 230 | 8.374 | −15.572 | −48.913 | 1.00 | 31.00 A |
| ATOM | 1249 | CA | GLN | A | 230 | 8.238 | −15.162 | −50.305 | 1.00 | 31.22 A |
| ATOM | 1250 | CB | GLN | A | 230 | 6.884 | −14.487 | −50.533 | 1.00 | 32.85 A |
| ATOM | 1251 | CG | GLN | A | 230 | 5.709 | −15.456 | −50.531 | 1.00 | 37.00 A |
| ATOM | 1252 | CD | GLN | A | 230 | 4.364 | −14.754 | −50.639 | 1.00 | 38.18 A |
| ATOM | 1253 | OE1 | GLN | A | 230 | 4.100 | −14.024 | −51.601 | 1.00 | 38.74 A |
| ATOM | 1254 | NE2 | GLN | A | 230 | 3.502 | −14.976 | −49.650 | 1.00 | 37.86 A |
| ATOM | 1255 | C | GLN | A | 230 | 9.348 | −14.243 | −50.787 | 1.00 | 29.78 A |
| ATOM | 1256 | O | GLN | A | 230 | 9.902 | −14.453 | −51.869 | 1.00 | 29.39 A |
| ATOM | 1257 | N | VAL | A | 231 | 9.665 | −13.217 | −50.005 | 1.00 | 27.08 A |
| ATOM | 1258 | CA | VAL | A | 231 | 10.726 | −12.303 | −50.401 | 1.00 | 26.16 A |
| ATOM | 1259 | CB | VAL | A | 231 | 10.801 | −11.080 | −49.469 | 1.00 | 26.30 A |
| ATOM | 1260 | CG1 | VAL | A | 231 | 9.551 | −10.231 | −49.610 | 1.00 | 25.48 A |
| ATOM | 1261 | CG2 | VAL | A | 231 | 10.936 | −11.536 | −48.055 | 1.00 | 27.95 A |
| ATOM | 1262 | C | VAL | A | 231 | 12.050 | −13.056 | −50.371 | 1.00 | 25.45 A |
| ATOM | 1263 | O | VAL | A | 231 | 12.949 | −12.789 | −51.172 | 1.00 | 25.65 A |
| ATOM | 1264 | N | LEU | A | 232 | 12.162 | −14.014 | −49.456 | 1.00 | 24.04 A |
| ATOM | 1265 | CA | LEU | A | 232 | 13.379 | −14.804 | −49.345 | 1.00 | 22.95 A |
| ATOM | 1266 | CB | LEU | A | 232 | 13.304 | −15.753 | −48.148 | 1.00 | 23.20 A |
| ATOM | 1267 | CG | LEU | A | 232 | 14.562 | −16.605 | −47.940 | 1.00 | 24.20 A |
| ATOM | 1268 | CD1 | LEU | A | 232 | 15.782 | −15.692 | −47.782 | 1.00 | 25.17 A |
| ATOM | 1269 | CD2 | LEU | A | 232 | 14.390 | −17.490 | −46.718 | 1.00 | 25.41 A |
| ATOM | 1270 | C | LEU | A | 232 | 13.614 | −15.606 | −50.621 | 1.00 | 24.32 A |
| ATOM | 1271 | O | LEU | A | 232 | 14.745 | −15.687 | −51.113 | 1.00 | 23.37 A |
| ATOM | 1272 | N | ASP | A | 233 | 12.554 | −16.206 | −51.156 | 1.00 | 24.48 A |
| ATOM | 1273 | CA | ASP | A | 233 | 12.688 | −16.974 | −52.386 | 1.00 | 25.90 A |
| ATOM | 1274 | CB | ASP | A | 233 | 11.348 | −17.582 | −52.826 | 1.00 | 27.95 A |
| ATOM | 1275 | CG | ASP | A | 233 | 10.871 | −18.694 | −51.902 | 1.00 | 31.23 A |
| ATOM | 1276 | OD1 | ASP | A | 233 | 11.721 | −19.352 | −51.261 | 1.00 | 31.77 A |
| ATOM | 1277 | OD2 | ASP | A | 233 | 9.642 | −18.922 | −51.831 | 1.00 | 33.39 A |
| ATOM | 1278 | C | ASP | A | 233 | 13.209 | −16.065 | −53.490 | 1.00 | 24.49 A |
| ATOM | 1279 | O | ASP | A | 233 | 14.045 | −16.477 | −54.288 | 1.00 | 23.31 A |
| ATOM | 1280 | N | SER | A | 234 | 12.728 | −14.822 | −53.519 | 1.00 | 23.93 A |
| ATOM | 1281 | CA | SER | A | 234 | 13.144 | −13.867 | −54.546 | 1.00 | 24.19 A |
| ATOM | 1282 | CB | SER | A | 234 | 12.434 | −12.522 | −54.357 | 1.00 | 24.54 A |
| ATOM | 1283 | OG | SER | A | 234 | 13.044 | −11.745 | −53.341 | 1.00 | 26.38 A |
| ATOM | 1284 | C | SER | A | 234 | 14.655 | −13.624 | −54.609 | 1.00 | 24.31 A |
| ATOM | 1285 | O | SER | A | 234 | 15.154 | −13.082 | −55.591 | 1.00 | 26.53 A |
| ATOM | 1286 | N | ILE | A | 235 | 15.388 | −14.006 | −53.570 | 1.00 | 23.33 A |
| ATOM | 1287 | CA | ILE | A | 235 | 16.830 | −13.808 | −53.596 | 1.00 | 21.51 A |
| ATOM | 1288 | CB | ILE | A | 235 | 17.262 | −12.641 | −52.663 | 1.00 | 20.78 A |
| ATOM | 1289 | CG2 | ILE | A | 235 | 16.624 | −11.329 | −53.138 | 1.00 | 14.94 A |
| ATOM | 1290 | CG1 | ILE | A | 235 | 16.879 | −12.964 | −51.216 | 1.00 | 18.91 A |
| ATOM | 1291 | CD1 | ILE | A | 235 | 17.392 | −11.968 | −50.211 | 1.00 | 18.32 A |
| ATOM | 1292 | C | ILE | A | 235 | 17.616 | −15.061 | −53.215 | 1.00 | 22.26 A |
| ATOM | 1293 | O | ILE | A | 235 | 18.810 | −14.983 | −52.919 | 1.00 | 22.63 A |
| ATOM | 1294 | N | ARG | A | 236 | 16.958 | −16.217 | −53.229 | 1.00 | 22.15 A |
| ATOM | 1295 | CA | ARG | A | 236 | 17.637 | −17.459 | −52.882 | 1.00 | 23.00 A |
| ATOM | 1296 | CB | ARG | A | 236 | 16.685 | −18.648 | −53.003 | 1.00 | 24.18 A |
| ATOM | 1297 | CG | ARG | A | 236 | 15.802 | −18.852 | −51.786 | 1.00 | 28.66 A |
| ATOM | 1298 | CD | ARG | A | 236 | 14.937 | −20.104 | −51.903 | 1.00 | 30.02 A |
| ATOM | 1299 | NE | ARG | A | 236 | 14.181 | −20.349 | −50.678 | 1.00 | 31.89 A |
| ATOM | 1300 | CZ | ARG | A | 236 | 14.710 | −20.823 | −49.552 | 1.00 | 33.51 A |
| ATOM | 1301 | NH1 | ARG | A | 236 | 16.003 | −21.115 | −49.490 | 1.00 | 33.19 A |
| ATOM | 1302 | NH2 | ARG | A | 236 | 13.947 | −20.989 | −48.480 | 1.00 | 35.80 A |
| ATOM | 1303 | C | ARG | A | 236 | 18.865 | −17.704 | −53.758 | 1.00 | 24.86 A |
| ATOM | 1304 | O | ARG | A | 236 | 19.946 | −18.026 | −53.248 | 1.00 | 24.45 A |
| ATOM | 1305 | N | GLU | A | 237 | 18.698 | −17.556 | −55.073 | 1.00 | 23.40 A |
| ATOM | 1306 | CA | GLU | A | 237 | 19.802 | −17.775 | −55.996 | 1.00 | 22.38 A |
| ATOM | 1307 | CB | GLU | A | 237 | 19.339 | −17.613 | −57.450 | 1.00 | 21.86 A |
| ATOM | 1308 | CG | GLU | A | 237 | 18.187 | −18.534 | −57.832 | 1.00 | 26.01 A |
| ATOM | 1309 | CD | GLU | A | 237 | 18.347 | −19.954 | −57.284 | 1.00 | 28.79 A |
| ATOM | 1310 | OE1 | GLU | A | 237 | 19.326 | −20.640 | −57.649 | 1.00 | 31.36 A |
| ATOM | 1311 | OE2 | GLU | A | 237 | 17.487 | −20.387 | −56.479 | 1.00 | 31.54 A |
| ATOM | 1312 | C | GLU | A | 237 | 20.931 | −16.803 | −55.683 | 1.00 | 19.80 A |
| ATOM | 1313 | O | GLU | A | 237 | 22.102 | −17.174 | −55.709 | 1.00 | 18.95 A |
| ATOM | 1314 | N | GLU | A | 238 | 20.570 | −15.567 | −55.362 | 1.00 | 17.58 A |
| ATOM | 1315 | CA | GLU | A | 238 | 21.557 | −14.546 | −55.035 | 1.00 | 16.50 A |
| ATOM | 1316 | CB | GLU | A | 238 | 20.848 | −13.219 | −54.729 | 1.00 | 16.60 A |
| ATOM | 1317 | CG | GLU | A | 238 | 20.357 | −12.449 | −55.972 | 1.00 | 15.75 A |

-continued

| | | | | | | | | | | |
|---|---|---|---|---|---|---|---|---|---|---|
| ATOM | 1318 | CD | GLU | A | 238 | 19.198 | −13.120 | −56.712 | 1.00 | 16.05 A |
| ATOM | 1319 | OE1 | GLU | A | 238 | 18.860 | −12.653 | −57.817 | 1.00 | 15.84 A |
| ATOM | 1320 | OE2 | GLU | A | 238 | 18.613 | −14.097 | −56.199 | 1.00 | 19.07 A |
| ATOM | 1321 | C | GLU | A | 238 | 22.449 | −14.961 | −53.851 | 1.00 | 16.83 A |
| ATOM | 1322 | O | GLU | A | 238 | 23.677 | −14.877 | −53.925 | 1.00 | 14.90 A |
| ATOM | 1323 | N | LEU | A | 239 | 21.820 | −15.405 | −52.764 | 1.00 | 15.47 A |
| ATOM | 1324 | CA | LEU | A | 239 | 22.542 | −15.836 | −51.574 | 1.00 | 16.39 A |
| ATOM | 1325 | CB | LEU | A | 239 | 21.553 | −16.095 | −50.428 | 1.00 | 14.91 A |
| ATOM | 1326 | CG | LEU | A | 239 | 20.700 | −14.891 | −50.006 | 1.00 | 17.17 A |
| ATOM | 1327 | CD1 | LEU | A | 239 | 19.828 | −15.234 | −48.796 | 1.00 | 15.12 A |
| ATOM | 1328 | CD2 | LEU | A | 239 | 21.617 | −13.734 | −49.679 | 1.00 | 15.57 A |
| ATOM | 1329 | C | LEU | A | 239 | 23.344 | −17.100 | −51.874 | 1.00 | 16.05 A |
| ATOM | 1330 | O | LEU | A | 239 | 24.430 | −17.316 | −51.331 | 1.00 | 14.99 A |
| ATOM | 1331 | N | GLU | A | 240 | 22.800 | −17.927 | −52.756 | 1.00 | 17.95 A |
| ATOM | 1332 | CA | GLU | A | 240 | 23.444 | −19.169 | −53.149 | 1.00 | 21.35 A |
| ATOM | 1333 | CB | GLU | A | 240 | 22.492 | −19.969 | −54.037 | 1.00 | 25.83 A |
| ATOM | 1334 | CG | GLU | A | 240 | 22.635 | −21.471 | −53.966 | 1.00 | 31.74 A |
| ATOM | 1335 | CD | GLU | A | 240 | 21.535 | −22.176 | −54.753 | 1.00 | 36.90 A |
| ATOM | 1336 | OE1 | GLU | A | 240 | 20.349 | −21.810 | −54.566 | 1.00 | 37.59 A |
| ATOM | 1337 | OE2 | GLU | A | 240 | 21.853 | −23.092 | −55.549 | 1.00 | 39.47 A |
| ATOM | 1338 | C | GLU | A | 240 | 24.740 | −18.854 | −53.903 | 1.00 | 19.90 A |
| ATOM | 1339 | O | GLU | A | 240 | 25.748 | −19.548 | −53.743 | 1.00 | 20.76 A |
| ATOM | 1340 | N | ALA | A | 241 | 24.711 | −17.798 | −54.710 | 1.00 | 18.49 A |
| ATOM | 1341 | CA | ALA | A | 241 | 25.887 | −17.396 | −55.480 | 1.00 | 18.34 A |
| ATOM | 1342 | CB | ALA | A | 241 | 25.515 | −16.306 | −56.483 | 1.00 | 19.10 A |
| ATOM | 1343 | C | ALA | A | 241 | 27.007 | −16.905 | −54.566 | 1.00 | 17.84 A |
| ATOM | 1344 | O | ALA | A | 241 | 28.183 | −17.073 | −54.881 | 1.00 | 17.32 A |
| ATOM | 1345 | N | LEU | A | 242 | 26.642 | −16.289 | −53.441 | 1.00 | 17.42 A |
| ATOM | 1346 | CA | LEU | A | 242 | 27.641 | −15.794 | −52.494 | 1.00 | 17.40 A |
| ATOM | 1347 | CB | LEU | A | 242 | 27.005 | −14.800 | −51.517 | 1.00 | 14.72 A |
| ATOM | 1348 | CG | LEU | A | 242 | 26.611 | −13.447 | −52.119 | 1.00 | 13.60 A |
| ATOM | 1349 | CD1 | LEU | A | 242 | 25.823 | −12.653 | −51.105 | 1.00 | 13.80 A |
| ATOM | 1350 | CD2 | LEU | A | 242 | 27.848 | −12.675 | −52.532 | 1.00 | 10.81 A |
| ATOM | 1351 | C | LEU | A | 242 | 28.267 | −16.965 | −51.730 | 1.00 | 18.23 A |
| ATOM | 1352 | O | LEU | A | 242 | 29.445 | −16.925 | −51.375 | 1.00 | 16.99 A |
| ATOM | 1353 | N | GLU | A | 243 | 27.472 | −18.007 | −51.494 | 1.00 | 19.15 A |
| ATOM | 1354 | CA | GLU | A | 243 | 27.941 | −19.197 | −50.792 | 1.00 | 20.79 A |
| ATOM | 1355 | CB | GLU | A | 243 | 26.770 | −20.140 | −50.507 | 1.00 | 21.06 A |
| ATOM | 1356 | CG | CLU | A | 243 | 25.848 | −19.685 | −49.378 | 1.00 | 19.76 A |
| ATOM | 1357 | CD | GLU | A | 243 | 24.475 | −20.318 | −49.474 | 1.00 | 20.44 A |
| ATOM | 1358 | OE1 | GLU | A | 243 | 24.357 | −21.358 | −50.150 | 1.00 | 22.37 A |
| ATOM | 1359 | OE2 | GLU | A | 243 | 23.518 | −19.784 | −48.873 | 1.00 | 20.73 A |
| ATOM | 1360 | C | GLU | A | 243 | 28.975 | −19.912 | −51.649 | 1.00 | 22.94 A |
| ATOM | 1361 | O | GLU | A | 243 | 29.983 | −20.410 | −51.143 | 1.00 | 22.58 A |
| ATOM | 1362 | N | LYS | A | 244 | 28.717 | −19.963 | −52.951 | 1.00 | 23.02 A |
| ATOM | 1363 | CA | LYS | A | 244 | 29.637 | −20.601 | −53.879 | 1.00 | 24.52 A |
| ATOM | 1364 | CB | LYS | A | 244 | 28.966 | −20.798 | −55.242 | 1.00 | 25.82 A |
| ATOM | 1365 | CG | LYS | A | 244 | 27.699 | −21.650 | −55.171 | 1.00 | 31.89 A |
| ATOM | 1366 | CD | LYS | A | 244 | 27.998 | −23.064 | −54.652 | 1.00 | 34.68 A |
| ATOM | 1367 | CE | LYS | A | 244 | 26.751 | −23.745 | −54.097 | 1.00 | 35.93 A |
| ATOM | 1368 | NZ | LYS | A | 244 | 26.233 | −23.064 | −52.871 | 1.00 | 36.31 A |
| ATOM | 1369 | C | LYS | A | 244 | 30.884 | −19.735 | −54.024 | 1.00 | 24.80 A |
| ATOM | 1370 | O | LYS | A | 244 | 32.005 | −20.239 | −53.979 | 1.00 | 24.15 A |
| ATOM | 1371 | N | LYS | A | 245 | 30.686 | −18.431 | −54.194 | 1.00 | 23.61 A |
| ATOM | 1372 | CA | LYS | A | 245 | 31.805 | −17.503 | −54.330 | 1.00 | 23.86 A |
| ATOM | 1373 | CB | LYS | A | 245 | 31.276 | −16.075 | −54.482 | 1.00 | 24.85 A |
| ATOM | 1374 | CG | LYS | A | 245 | 32.325 | −14.977 | −54.377 | 1.00 | 27.82 A |
| ATOM | 1375 | CD | LYS | A | 245 | 33.472 | −15.174 | −55.357 | 1.00 | 30.16 A |
| ATOM | 1376 | CE | LYS | A | 245 | 33.044 | −14.966 | −56.803 | 1.00 | 32.00 A |
| ATOM | 1377 | NZ | LYS | A | 245 | 34.179 | −15.225 | −57.737 | 1.00 | 29.90 A |
| ATOM | 1378 | C | LYS | A | 245 | 32.715 | −17.609 | −53.105 | 1.00 | 23.77 A |
| ATOM | 1379 | O | LYS | A | 245 | 33.938 | −17.506 | −53.207 | 1.00 | 21.14 A |
| ATOM | 1380 | N | TYR | A | 246 | 32.098 | −17.827 | −51.949 | 1.00 | 23.97 A |
| ATOM | 1381 | CA | TYR | A | 246 | 32.823 | −17.966 | −50.694 | 1.00 | 23.96 A |
| ATOM | 1382 | CB | TYR | A | 246 | 31.845 | −18.110 | −49.531 | 1.00 | 23.71 A |
| ATOM | 1383 | CG | TYR | A | 246 | 32.520 | −18.412 | −48.219 | 1.00 | 24.55 A |
| ATOM | 1384 | CD1 | TYR | A | 246 | 33.192 | −17.415 | −47.518 | 1.00 | 23.26 A |
| ATOM | 1385 | CE1 | TYR | A | 246 | 33.847 | −17.697 | −46.323 | 1.00 | 23.72 A |
| ATOM | 1386 | CD2 | TYR | A | 246 | 32.517 | −19.705 | −47.692 | 1.00 | 25.41 A |
| ATOM | 1387 | CE2 | TYR | A | 246 | 33.172 | −19.998 | −46.497 | 1.00 | 24.58 A |
| ATOM | 1388 | CZ | TYR | A | 246 | 33.835 | −18.986 | −45.821 | 1.00 | 24.76 A |
| ATOM | 1389 | OH | TYR | A | 246 | 34.501 | −19.257 | −44.647 | 1.00 | 25.79 A |
| ATOM | 1390 | C | TYR | A | 246 | 33.688 | −19.210 | −50.751 | 1.00 | 24.29 A |
| ATOM | 1391 | O | TYR | A | 246 | 34.864 | −19.187 | −50.386 | 1.00 | 23.22 A |
| ATOM | 1392 | N | GLU | A | 247 | 33.077 | −20.302 | −51.193 | 1.00 | 24.70 A |
| ATOM | 1393 | CA | GLU | A | 247 | 33.767 | −21.569 | −51.302 | 1.00 | 26.80 A |
| ATOM | 1394 | CB | GLU | A | 247 | 32.783 | −22.658 | −51.732 | 1.00 | 25.70 A |
| ATOM | 1395 | CG | GLU | A | 247 | 31.852 | −23.115 | −50.617 | 1.00 | 26.11 A |
| ATOM | 1396 | CD | GLU | A | 247 | 30.768 | −24.069 | −51.098 | 1.00 | 26.88 A |

-continued

| ATOM | 1397 | OE1 | GLU | A | 247 | 31.094 | −25.045 | −51.804 | 1.00 | 27.71 | A |
| --- | --- | --- | --- | --- | --- | --- | --- | --- | --- | --- | --- |
| ATOM | 1398 | OE2 | GLU | A | 247 | 29.584 | −23.848 | −50.764 | 1.00 | 28.44 | A |
| ATOM | 1399 | C | GLU | A | 247 | 34.916 | −21.461 | −52.297 | 1.00 | 27.97 | A |
| ATOM | 1400 | O | GLU | A | 247 | 36.018 | −21.937 | −52.033 | 1.00 | 29.90 | A |
| ATOM | 1401 | N | GLU | A | 248 | 34.660 | −20.816 | −53.428 | 1.00 | 29.20 | A |
| ATOM | 1402 | CA | GLU | A | 248 | 35.675 | −20.654 | −54.460 | 1.00 | 31.97 | A |
| ATOM | 1403 | CB | GLU | A | 248 | 35.073 | −20.025 | −55.726 | 1.00 | 34.39 | A |
| ATOM | 1404 | CG | GLU | A | 248 | 35.868 | −20.328 | −57.004 | 1.00 | 40.86 | A |
| ATOM | 1405 | CD | GLU | A | 248 | 35.930 | −19.154 | −57.983 | 1.00 | 44.67 | A |
| ATOM | 1406 | OE1 | GLU | A | 248 | 34.864 | −18.578 | −58.313 | 1.00 | 47.37 | A |
| ATOM | 1407 | OE2 | GLU | A | 248 | 37.052 | −18.813 | −58.432 | 1.00 | 44.21 | A |
| ATOM | 1408 | C | GLU | A | 248 | 36.829 | −19.780 | −53.976 | 1.00 | 31.88 | A |
| ATOM | 1409 | O | GLU | A | 248 | 37.993 | −20.072 | −54.255 | 1.00 | 31.42 | A |
| ATOM | 1410 | N | LYS | A | 249 | 36.509 | −18.708 | −53.254 | 1.00 | 31.46 | A |
| ATOM | 1411 | CA | LYS | A | 249 | 37.546 | −17.803 | −52.769 | 1.00 | 31.64 | A |
| ATOM | 1412 | CB | LYS | A | 249 | 36.948 | −16.456 | −52.340 | 1.00 | 31.29 | A |
| ATOM | 1413 | CG | LYS | A | 249 | 37.985 | −15.524 | −51.731 | 1.00 | 33.88 | A |
| ATOM | 1414 | CD | LYS | A | 249 | 37.443 | −14.145 | −51.384 | 1.00 | 36.01 | A |
| ATOM | 1415 | CE | LYS | A | 249 | 38.546 | −13.266 | −50.777 | 1.00 | 38.28 | A |
| ATOM | 1416 | NZ | LYS | A | 249 | 38.102 | −11.882 | −50.419 | 1.00 | 39.36 | A |
| ATOM | 1417 | C | LYS | A | 249 | 38.372 | −18.371 | −51.618 | 1.00 | 31.30 | A |
| ATOM | 1418 | O | LYS | A | 249 | 39.598 | −18.353 | −51.672 | 1.00 | 31.00 | A |
| ATOM | 1419 | N | THR | A | 250 | 37.708 | −18.877 | −50.584 | 1.00 | 30.44 | A |
| ATOM | 1420 | CA | THR | A | 250 | 38.418 | −19.414 | −49.428 | 1.00 | 31.23 | A |
| ATOM | 1421 | CB | THR | A | 250 | 37.555 | −19.338 | −48.148 | 1.00 | 31.86 | A |
| ATOM | 1422 | OG1 | THR | A | 250 | 36.507 | −20.314 | −48.214 | 1.00 | 34.34 | A |
| ATOM | 1423 | CG2 | THR | A | 250 | 36.941 | −17.952 | −48.001 | 1.00 | 34.00 | A |
| ATOM | 1424 | C | THR | A | 250 | 38.892 | −20.857 | −49.586 | 1.00 | 30.95 | A |
| ATOM | 1425 | O | THR | A | 250 | 39.942 | −21.223 | −49.065 | 1.00 | 29.91 | A |
| ATOM | 1426 | N | GLY | A | 251 | 38.125 | −21.668 | −50.306 | 1.00 | 30.20 | A |
| ATOM | 1427 | CA | GLY | A | 251 | 38.491 | −23.064 | −50.475 | 1.00 | 30.06 | A |
| ATOM | 1428 | C | GLY | A | 251 | 37.843 | −23.878 | −49.365 | 1.00 | 30.74 | A |
| ATOM | 1429 | O | GLY | A | 251 | 38.060 | −25.083 | −49.238 | 1.00 | 31.77 | A |
| ATOM | 1430 | N | LEU | A | 252 | 37.030 | −23.193 | −48.564 | 1.00 | 29.90 | A |
| ATOM | 1431 | CA | LEU | A | 252 | 36.323 | −23.790 | −47.440 | 1.00 | 27.62 | A |
| ATOM | 1432 | CB | LEU | A | 252 | 36.561 | −22.942 | −46.191 | 1.00 | 27.01 | A |
| ATOM | 1433 | CG | LEU | A | 252 | 38.024 | −22.633 | −45.872 | 1.00 | 25.71 | A |
| ATOM | 1434 | CD1 | LEU | A | 252 | 38.102 | −21.489 | −44.875 | 1.00 | 25.85 | A |
| ATOM | 1435 | CD2 | LEU | A | 252 | 38.701 | −23.888 | −45.330 | 1.00 | 24.69 | A |
| ATOM | 1436 | C | LEU | A | 252 | 34.823 | −23.840 | −47.736 | 1.00 | 27.80 | A |
| ATOM | 1437 | O | LEU | A | 252 | 34.306 | −23.006 | −48.480 | 1.00 | 27.40 | A |
| ATOM | 1438 | N | PRO | A | 253 | 34.109 | −24.822 | −47.159 | 1.00 | 27.39 | A |
| ATOM | 1439 | CD | PRO | A | 253 | 34.659 | −25.921 | −46.355 | 1.00 | 27.81 | A |
| ATOM | 1440 | CA | PRO | A | 253 | 32.663 | −24.994 | −47.344 | 1.00 | 28.16 | A |
| ATOM | 1441 | CB | PRO | A | 253 | 32.399 | −26.394 | −46.784 | 1.00 | 28.26 | A |
| ATOM | 1442 | CG | PRO | A | 253 | 33.756 | −27.045 | −46.736 | 1.00 | 28.79 | A |
| ATOM | 1443 | C | PRO | A | 253 | 31.954 | −23.931 | −46.506 | 1.00 | 29.29 | A |
| ATOM | 1444 | O | PRO | A | 253 | 32.331 | −23.707 | −45.355 | 1.00 | 30.16 | A |
| ATOM | 1445 | N | SER | A | 254 | 30.931 | −23.283 | −47.054 | 1.00 | 30.59 | A |
| ATOM | 1446 | CA | SER | A | 254 | 30.231 | −22.248 | −46.286 | 1.00 | 32.13 | A |
| ATOM | 1447 | CB | SER | A | 254 | 29.629 | −21.192 | −47.219 | 1.00 | 31.94 | A |
| ATOM | 1448 | OG | SER | A | 254 | 28.478 | −21.688 | −47.880 | 1.00 | 30.37 | A |
| ATOM | 1449 | C | SER | A | 254 | 29.114 | −22.815 | −45.423 | 1.00 | 32.34 | A |
| ATOM | 1450 | O | SER | A | 254 | 28.543 | −23.851 | −45.742 | 1.00 | 30.85 | A |
| ATOM | 1451 | N | PRO | A | 255 | 28.808 | −22.150 | −44.299 | 1.00 | 34.62 | A |
| ATOM | 1452 | CD | PRO | A | 255 | 29.704 | −21.193 | −43.627 | 1.00 | 33.82 | A |
| ATOM | 1453 | CA | PRO | A | 255 | 27.736 | −22.594 | −43.393 | 1.00 | 35.62 | A |
| ATOM | 1454 | CB | PRO | A | 255 | 28.082 | −21.906 | −42.079 | 1.00 | 36.32 | A |
| ATOM | 1455 | CG | PRO | A | 255 | 29.590 | −21.635 | −42.200 | 1.00 | 35.07 | A |
| ATOM | 1456 | C | PRO | A | 255 | 26.410 | −22.096 | −43.984 | 1.00 | 38.43 | A |
| ATOM | 1457 | O | PRO | A | 255 | 25.564 | −21.528 | −43.295 | 1.00 | 37.08 | A |
| ATOM | 1458 | N | GLU | A | 256 | 26.273 | −22.334 | −45.287 | 1.00 | 42.39 | A |
| ATOM | 1459 | CA | GLU | A | 256 | 25.139 | −21.942 | −46.124 | 1.00 | 45.09 | A |
| ATOM | 1460 | CB | GLU | A | 256 | 25.419 | −22.388 | −47.564 | 1.00 | 48.71 | A |
| ATOM | 1461 | CG | GLU | A | 256 | 24.872 | −23.776 | −47.940 | 1.00 | 51.06 | A |
| ATOM | 1462 | CD | GLU | A | 256 | 25.525 | −24.911 | −47.177 | 1.00 | 54.43 | A |
| ATOM | 1463 | OE1 | GLU | A | 256 | 26.723 | −25.180 | −47.422 | 1.00 | 54.78 | A |
| ATOM | 1464 | OE2 | GLU | A | 256 | 24.840 | −25.533 | −46.334 | 1.00 | 54.37 | A |
| ATOM | 1465 | C | GLU | A | 256 | 23.721 | −22.388 | −45.759 | 1.00 | 45.88 | A |
| ATOM | 1466 | O | GLU | A | 256 | 23.420 | −22.700 | −44.607 | 1.00 | 46.95 | A |
| ATOM | 1467 | N | ARG | A | 257 | 22.875 | −22.396 | −46.795 | 1.00 | 47.40 | A |
| ATOM | 1468 | CA | ARG | A | 257 | 21.458 | −22.766 | −46.768 | 1.00 | 48.03 | A |
| ATOM | 1469 | CB | ARG | A | 257 | 21.166 | −23.841 | −45.708 | 1.00 | 49.00 | A |
| ATOM | 1470 | CG | ARG | A | 257 | 19.673 | −24.239 | −45.527 | 1.00 | 49.58 | A |
| ATOM | 1471 | CD | ARG | A | 257 | 18.926 | −24.462 | −46.845 | 1.00 | 50.25 | A |
| ATOM | 1472 | NE | ARG | A | 257 | 18.716 | −23.197 | −47.542 | 1.00 | 50.22 | A |
| ATOM | 1473 | CZ | ARG | A | 257 | 19.098 | −22.961 | −48.791 | 1.00 | 51.01 | A |
| ATOM | 1474 | NH1 | ARG | A | 257 | 19.705 | −23.913 | −49.485 | 1.00 | 51.87 | A |
| ATOM | 1475 | NH2 | ARG | A | 257 | 18.900 | −21.767 | −49.332 | 1.00 | 51.93 | A |

-continued

| | | | | | | | | | |
|---|---|---|---|---|---|---|---|---|---|
| ATOM | 1476 | C | ARG | A | 257 | 20.576 | −21.545 | −46.548 | 1.00 | 48.27 A |
| ATOM | 1477 | O | ARG | A | 257 | 19.959 | −21.445 | −45.465 | 1.00 | 48.75 A |
| ATOM | 1478 | OXT | ARG | A | 257 | 20.517 | −20.700 | −47.471 | 1.00 | 47.21 A |
| ATOM | 1479 | S | SO4 | L | 1 | 26.750 | −1.543 | −20.726 | 1.00 | 38.59 L |
| ATOM | 1480 | O1 | SO4 | L | 1 | 26.466 | −2.892 | −21.261 | 1.00 | 36.34 L |
| ATOM | 1481 | O2 | SO4 | L | 1 | 25.516 | −0.950 | −20.178 | 1.00 | 38.18 L |
| ATOM | 1482 | O3 | SO4 | L | 1 | 27.748 | −1.640 | −19.643 | 1.00 | 39.55 L |
| ATOM | 1483 | O4 | SO4 | L | 1 | 27.270 | −0.687 | −21.812 | 1.00 | 36.64 L |
| ATOM | 1484 | ZN + 2 | ZN2 | M | 1 | 24.054 | −4.948 | −43.032 | 1.00 | 17.46 M |
| ATOM | 1485 | ZN + 2 | ZN2 | M | 2 | 39.953 | 7.918 | −41.358 | 1.00 | 25.22 M |
| ATOM | 1486 | ZN + 2 | ZN2 | M | 3 | 36.946 | −5.734 | −22.999 | 1.00 | 22.38 M |
| ATOM | 1487 | ZN + 2 | ZN2 | M | 4 | 19.157 | −22.594 | −56.610 | 0.50 | 43.08 M |
| ATOM | 1488 | ZN + 2 | ZN2 | M | 5 | 21.794 | −10.556 | −27.675 | 0.40 | 29.27 M |
| ATOM | 1489 | ZN + 2 | ZN2 | M | 6 | −0.285 | 1.757 | −30.184 | 0.50 | 36.10 M |
| ATOM | 1490 | OH2 | TIP | S | 1 | 25.969 | −2.074 | −44.807 | 1.00 | 14.25 S |
| ATOM | 1491 | OH2 | TIP | S | 2 | 3.811 | 2.346 | −30.357 | 1.00 | 14.25 S |
| ATOM | 1492 | OH2 | TIP | S | 3 | −0.051 | 0.258 | −28.134 | 1.00 | 14.25 S |
| ATOM | 1493 | OH2 | TIP | S | 4 | 10.090 | −8.668 | −43.625 | 1.00 | 15.50 S |
| ATOM | 1494 | OH2 | TIP | S | 5 | 24.192 | −17.873 | −42.585 | 1.00 | 9.05 S |
| ATOM | 1495 | OH2 | TIP | S | 6 | 26.335 | −9.687 | −38.091 | 1.00 | 2.09 S |
| ATOM | 1496 | OH2 | TIP | S | 7 | 42.910 | −1.393 | −27.043 | 1.00 | 40.60 S |
| ATOM | 1497 | OH2 | TIP | S | 8 | 22.287 | −8.014 | −43.054 | 1.00 | 3.78 S |
| ATOM | 1498 | OH2 | TIP | S | 9 | 22.996 | −4.825 | −50.565 | 1.00 | 6.81 S |
| ATOM | 1499 | OH2 | TIP | S | 10 | 9.921 | −9.608 | −46.068 | 1.00 | 10.87 S |
| ATOM | 1500 | OH2 | TIP | S | 11 | 21.456 | −25.782 | −55.836 | 1.00 | 28.41 S |
| ATOM | 1501 | OH2 | TIP | S | 12 | 31.066 | 7.682 | −53.311 | 1.00 | 21.03 S |
| ATOM | 1502 | OH2 | TIP | S | 13 | 11.349 | −7.646 | −52.115 | 1.00 | 13.10 S |
| ATOM | 1503 | OH2 | TIP | S | 14 | 24.496 | −4.224 | −28.092 | 1.00 | 23.20 S |
| ATOM | 1504 | OH2 | TIP | S | 15 | 20.931 | −22.429 | −58.425 | 1.00 | 14.25 S |
| ATOM | 1505 | OH2 | TIP | S | 16 | 27.530 | −14.722 | −42.923 | 1.00 | 9.87 S |
| ATOM | 1506 | OH2 | TIP | S | 17 | 9.342 | 6.275 | −38.471 | 1.00 | 18.89 S |
| ATOM | 1507 | OH2 | TIP | S | 18 | 5.984 | −3.364 | −30.710 | 1.00 | 11.90 S |
| ATOM | 1508 | OH2 | TIP | S | 19 | 19.793 | −0.210 | −46.871 | 1.00 | 26.54 S |
| ATOM | 1509 | OH2 | TIP | S | 20 | 28.046 | −17.680 | −41.836 | 1.00 | 10.88 S |
| ATOM | 1510 | OH2 | TIP | S | 23 | 21.557 | −7.309 | −40.376 | 1.00 | 14.41 S |
| ATOM | 1511 | OH2 | TIP | S | 24 | 12.004 | 1.128 | −39.615 | 1.00 | 16.43 S |
| ATOM | 1512 | OH2 | TIP | S | 25 | 30.777 | −14.876 | −50.134 | 1.00 | 11.00 S |
| ATOM | 1513 | OH2 | TIP | S | 26 | −1.303 | −0.882 | −25.776 | 1.00 | 38.49 S |
| ATOM | 1514 | OH2 | TIP | S | 28 | 13.901 | −4.350 | −36.733 | 1.00 | 17.30 S |
| ATOM | 1515 | OH2 | TIP | S | 30 | 28.137 | −11.377 | −35.724 | 1.00 | 13.45 S |
| ATOM | 1516 | OH2 | TIP | S | 32 | 10.937 | −8.045 | −38.922 | 1.00 | 19.04 S |
| ATOM | 1517 | OH2 | TIP | S | 33 | 32.844 | −9.803 | −54.314 | 1.00 | 43.74 S |
| ATOM | 1518 | OH2 | TIP | S | 34 | 36.191 | −3.234 | −48.811 | 1.00 | 43.05 S |
| ATOM | 1519 | OH2 | TIP | S | 36 | 16.139 | −16.545 | −56.285 | 1.00 | 35.15 S |
| ATOM | 1520 | OH2 | TIP | S | 37 | 33.130 | 11.162 | −16.863 | 1.00 | 27.08 S |
| ATOM | 1521 | OH2 | TIP | S | 38 | 13.131 | −19.278 | −54.777 | 1.00 | 21.83 S |
| ATOM | 1522 | OH2 | TIP | S | 39 | 26.597 | −10.167 | −54.360 | 1.00 | 17.41 S |
| ATOM | 1523 | OH2 | TIP | S | 40 | 12.308 | −8.028 | −32.094 | 1.00 | 23.20 S |
| ATOM | 1524 | OH2 | TIP | S | 41 | 23.225 | −15.656 | −35.045 | 1.00 | 28.13 S |
| ATOM | 1525 | OH2 | TIP | S | 42 | 24.923 | −2.981 | −42.626 | 1.00 | 13.51 S |
| ATOM | 1526 | OH2 | TIP | S | 43 | 44.298 | −1.798 | −33.197 | 1.00 | 17.76 S |
| ATOM | 1527 | OH2 | TIP | S | 44 | 20.680 | −0.619 | −44.292 | 1.00 | 14.01 S |
| ATOM | 1528 | OH2 | TIP | S | 45 | 5.896 | −15.409 | −44.351 | 1.00 | 22.87 S |
| ATOM | 1529 | OH2 | TIP | S | 46 | 23.233 | −24.442 | −53.915 | 1.00 | 39.19 S |
| ATOM | 1530 | OH2 | TIP | S | 47 | 14.208 | −10.403 | −32.245 | 1.00 | 18.95 S |
| ATOM | 1531 | OH2 | TIP | S | 48 | 38.832 | −0.501 | −27.020 | 1.00 | 14.49 S |
| ATOM | 1532 | OH2 | TIP | S | 49 | 18.236 | −0.002 | −44.579 | 1.00 | 27.51 S |
| ATOM | 1533 | OH2 | TIP | S | 50 | 36.434 | 8.748 | −34.776 | 1.00 | 11.42 S |
| ATOM | 1534 | OH2 | TIP | S | 51 | 27.579 | 14.569 | −38.647 | 1.00 | 28.40 S |
| ATOM | 1535 | OH2 | TIP | S | 52 | 38.153 | 2.185 | −20.385 | 1.00 | 15.38 S |
| ATOM | 1536 | OH2 | TIP | S | 54 | 29.121 | −17.432 | −57.522 | 1.00 | 14.06 S |
| ATOM | 1537 | OH2 | TIP | S | 55 | 28.554 | −19.346 | −40.014 | 1.00 | 37.78 S |
| ATOM | 1538 | OH2 | TIP | S | 56 | 22.082 | −22.880 | −50.314 | 1.00 | 24.72 S |
| ATOM | 1539 | OH2 | TIP | S | 59 | 35.171 | −10.112 | −50.196 | 1.00 | 27.04 S |
| ATOM | 1540 | OH2 | TIP | S | 61 | 9.233 | −20.875 | −49.991 | 1.00 | 31.75 S |
| ATOM | 1541 | OH2 | TIP | S | 62 | 18.870 | −7.844 | −55.461 | 1.00 | 34.62 S |
| ATOM | 1542 | OH2 | TIP | S | 63 | 11.323 | 3.689 | −39.850 | 1.00 | 18.17 S |
| ATOM | 1543 | OH2 | TIP | S | 64 | 35.403 | 9.921 | −37.907 | 1.00 | 26.55 S |
| ATOM | 1544 | OH2 | TIP | S | 65 | 8.090 | 14.529 | −43.710 | 1.00 | 30.17 S |
| ATOM | 1545 | OH2 | TIP | S | 66 | 38.045 | −0.048 | −19.192 | 1.00 | 30.52 S |
| ATOM | 1546 | OH2 | TIP | S | 67 | 33.352 | −13.694 | −29.289 | 1.00 | 33.68 S |
| ATOM | 1547 | OH2 | TIP | S | 69 | 35.976 | −15.780 | −40.760 | 1.00 | 13.56 S |

The examples set forth above are provided to give those of ordinary skill in the art a complete disclosure and description of how to make and use the embodiments of the devices, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

In addition, it is understood that the terminology used herein is for the purpose of describing particular embodiments only, and is not intended to be limiting. As used in this specification and the appended claims, the singular forms "a," "an," and "the" include plural referents unless the content clearly dictates otherwise. Unless defined otherwise, all technical and scientific terms used herein have the same meaning as commonly understood by one of ordinary skill in the art to which the invention pertains. Although any methods and materials similar or equivalent to those described herein can be used in the practice for testing of the invention(s), specific examples of appropriate materials and methods are described herein.

A number of embodiments of the invention have been described. Nevertheless, it will be understood that various modifications may be made without departing from the spirit and scope of the invention. Accordingly, other embodiments are within the scope of the following claims.

What is claimed is:

1. A crystalline form of a polypeptide consisting of the amino acid sequence of SEQ ID NO:1 complexed with $Zn^{2+}$, wherein said crystalline form has the space group symmetry $P4_12_12$; unit cell dimensions of a=about 49 angstroms to about 52 angstroms, b=about 49 angstroms to about 52 angstroms, and c=about 143 angstroms to about 147 angstroms and alpha=beta=gamma=90 degrees.

2. The crystalline form of claim 1, wherein said crystalline form produces the structural coordinates as set forth Table 1 upon X-ray diffraction pattern analysis.

3. The crystalline form of claim 1, wherein said crystalline form diffracts X-rays to a resolution of 2.4 angstroms.

4. The crystalline form of claim 1, wherein said unit cell dimensions are a=50.902 angstroms, b=50.902 angstroms, and c=144.783 angstroms.

* * * * *